(12) United States Patent
Shaposhnik

(10) Patent No.: US 12,319,681 B2
(45) Date of Patent: Jun. 3, 2025

(54) TRIPARTITE ANDROGEN RECEPTOR ELIMINATORS, METHODS AND USES THEREOF

(71) Applicant: SPG Therapeutics, Inc., Northridge, CA (US)

(72) Inventor: Zory Shaposhnik, Northridge, CA (US)

(73) Assignee: SPG Therapeutics, Inc., Northridge, CA (US)

( * ) Notice: Subject to any disclaimer, the term of this patent is extended or adjusted under 35 U.S.C. 154(b) by 2 days.

(21) Appl. No.: 17/931,773

(22) Filed: Sep. 13, 2022

(65) Prior Publication Data

US 2023/0092979 A1 Mar. 23, 2023

Related U.S. Application Data

(62) Division of application No. 16/608,749, filed as application No. PCT/US2018/030538 on May 1, 2018, now Pat. No. 11,447,483.

(60) Provisional application No. 62/492,822, filed on May 1, 2017.

(51) Int. Cl.
| | |
|---|---|
| *C07D 417/14* | (2006.01) |
| *C07C 43/196* | (2006.01) |
| *C07C 53/138* | (2006.01) |
| *C07C 69/708* | (2006.01) |
| *C07C 233/21* | (2006.01) |
| *C07D 405/14* | (2006.01) |
| *C07D 417/12* | (2006.01) |
| *C07J 71/00* | (2006.01) |

(52) U.S. Cl.
CPC .......... *C07D 417/14* (2013.01); *C07C 43/196* (2013.01); *C07C 53/138* (2013.01); *C07C 69/708* (2013.01); *C07C 233/21* (2013.01); *C07D 405/14* (2013.01); *C07D 417/12* (2013.01); *C07J 71/0005* (2013.01)

(58) Field of Classification Search
CPC .................................................. C07D 417/14
See application file for complete search history.

(56) References Cited

U.S. PATENT DOCUMENTS

| | | | |
|---|---|---|---|
| 3,013,012 A | 12/1961 | Cella et al. | |
| 6,790,979 B2 | 9/2004 | Lee et al. | |
| 8,198,323 B2 | 6/2012 | Lee et al. | |
| 2014/0170063 A1 | 6/2014 | Govindan et al. | |
| 2014/0356322 A1* | 12/2014 | Crews | A61P 25/08 514/19.5 |
| 2015/0119435 A1 | 4/2015 | Crews et al. | |
| 2016/0214972 A1 | 7/2016 | Jin et al. | |
| 2018/0147202 A1 | 5/2018 | Crew et al. | |

FOREIGN PATENT DOCUMENTS

| | | |
|---|---|---|
| WO | 2013170147 A1 | 11/2013 |
| WO | 2016118666 A1 | 7/2016 |
| WO | 2017004144 A1 | 1/2017 |

OTHER PUBLICATIONS

Crawford et al. Journal of Urology 2018, 200, 956-966 (Year: 2018).*
Layton et al. Am. J. Clin. Dermatol. 2017, 18, 169-191 (Year: 2017).*
Diago-Meseguer et al. Synthesis 1980, 7, 547-551 (Year: 1980).*
Hon et al. Nature, 2002, 417, 975-978 (Year: 2002).*
Raina et al. PNAS 2016, 113, 7124-7129 (Year: 2016).*
Antonarakis, et al., AR-V7 and Resistance to Enzalulamide and Abiraterone in Prostate Cancer, N. Engl. J. Med. B71: 1028-1038 {2014).
EPO, Extended EP Search Report for EP Patent Application Serial No. 18794821.1, pp. 7 (mailed on Dec. 11, 2020).
Gustafton, el al., Small-Molecule-Mediated Degradation of the Androgen Receptor through Hydrophobic Tagging, Angew. Chem. Int. Ed. 54(33): 9659-9662 {2015).
Hu, et al., (1 R ,2S)-4-(2-Cyano-cydohexyl-oxy)-2-trifluoromethy 1-benzonittile, a Potent Androgen Receptor Antagonist for Stimulating Hair Growth and Reducing Sebum Production, Bioorg. Med. Chem. Lett. 17: 5683-5688, 2007).
Hu, et al., Synthesis and Biological Evaluation of Amino-Pyridines as Androgen Receptor Antagonists for Stimulating Hair Growth and Reducing Sebum Production, Bioorg. Med. Chem. Lett. 17: 5693-5697 (2007).
Kretzschmar, el al., The Androgen Receptor Antagonizes Wnt/j3-Calenin Signaling in Epidermal Stem Cells, J. Invest. Dermatol. 135: 2753-2763 (2015).
Lai, et al, Induced Protein Degradation: An Emerging Drug Discovery Paradigm, Nat. Rav. 16:101-114 (2017).
Lai, el al., The Role of Androgen and Androgen Receptor in the Skin-Related Disorders, Arch. Dermatol. Res. 304(7): 499-510 (2012).
Neklesa, et al., ARV-330: Protac Androgen Receptor Degrader for Prostate Cancer, J. Clin. Oneal. 34{2Suppl): PCF Poster 267 {2016).

(Continued)

Primary Examiner — Matthew P Coughlin
(74) Attorney, Agent, or Firm — UltimatEdge IP Law Group, P.C.; Dean G. Stathakis

(57) ABSTRACT

The present specification discloses tripartite androgen receptor eliminators (AREs), pharmaceutical compositions and medicaments comprising such AREs, methods and uses for such AREs and compositions and medicaments, and methods and uses for AREs and compositions and medicaments for treating an androgen receptor signaling-mediated condition, disease or disorder.

19 Claims, No Drawings

(56) References Cited

OTHER PUBLICATIONS

Neklesa, et al., Small-Molecule Hydrophobic Tagging Induced Degradation of Halo Tag Fusion Proteins, Nat. Chem. Biol. 7(8): 538-543 (2012).
Nelson, et al., Bad Hair Day: Testosterone and Wnts, J. Invest. Dermatol. 135(11): 2567-2569 (2015).
Toure, et al., Small-Molecule PROTACS: New Approaches to Protein Degradation, Angew. Chem. Int. Ed. 55(6): 1966-1973 (2016).
Winter, et al., Phthalimide Conjugation as a Strategy for in vivo Target Protein Degradation, Science 348(6241): 1376-1381 (2015).
WIPO, PCT Form IB 373, International Preliminary Report on Patentability for IA Serial No. PCT/US2018/030538 (Nov. 14, 2019).
WIPO, PCT Form ISA210, International Search Report for International Patent Application Serial No. PCT/US2018/030538 (Jun. 27, 2018).
WIPO, PCT Form ISA237, Written Opinion for International Patent Application Serial No. PCT/US2018/030538 (Jun. 27, 2018).

* cited by examiner

TRIPARTITE ANDROGEN RECEPTOR ELIMINATORS, METHODS AND USES THEREOF

This application is a divisional that claims the benefit of priority and is entitled to the filing date pursuant to 35 U.S.C. § 121 of U.S. Non-Provisional patent application Ser. No. 16/608,749, filed Oct. 25, 2019, a 35 U.S.C. § 371 national stage patent application of International Patent Application Serial No. PCT/US2018/030538, filed May 1, 2018, which claims the benefit of priority and the filing date pursuant to 35 U.S.C. § 119 (e) to U.S. Provisional Patent Application 62/492,822, filed May 1, 2017, the content of each of which is hereby incorporated by reference in its entirety.

Androgens are well known to control the development and functions of the reproductive system in both male and female. The major circulating androgen is testosterone. Testosterone can be metabolized by 5α-reductases into a more potent androgen, 5α-dihydrotestosterone (DHT). Both testosterone and DHT can bind to androgen receptors, but DHT has ten-fold higher affinity for androgen receptors compared to testosterone.

Dermatologists recognize many different types of skin-related conditions, diseases and disorders that affect the health of the skin and/or hair. The role of androgen receptor signaling has been implicated in skin and hair physiology and pathogenesis based on the facts that androgen receptors and many androgenic steroidogenesis enzymes are expressed in skin, and the presence of sexual dimorphism in the etiology and diseases of skin and hair. While skin is not the major source of androgen synthesis, in sebocytes, sweat glands, and dermal papilla cells of hair, circulating androgenic pro-hormones, dehydroepiandrosterone (DHEA) and androstenedione, can be converted into testosterone and DHT. These potent androgens subsequently regulate dermal physiology through intracrine or paracrine manners. It has been shown that over-activation of androgen receptor by DHT has been shown to play a critical role in hair loss (alopecia) in males excess hair growth (hirsutism) in females. In addition, androgen receptor signaling is involved in excessive sebum production and appears to promote the abnormal or excessive inflammatory responses observed in many skin diseases, such as acne and psoriasis.

The present specification discloses new compounds, pharmaceutical compositions comprising these compounds and methods and uses of targeting the androgen receptor using these compounds and compositions in order to treat an androgen receptor signal mediated skin-related condition, disease or disorder that affects the health of the skin and/or hair. Such treatments safely and effectively promote healthy skin and hair of an individual.

SUMMARY

Aspects of the present specification disclose a compound of formula I $$\text{ARA-L-EE} \tag{I}$$

wherein ARA is an androgen receptor (AR) antagonist, L is a linker molecule and EE is an AR elimination promoter or elimination enhancer element. An AR antagonist disclosed herein can be any molecule that reduces or prevents agonist-mediated responses via an AR, including an orthosteric AR antagonist, an allosteric AR antagonist, or an AR antagonist that interacts at one or more unique binding sites not normally involved in the biological regulation of AR activity. An AR antagonist disclosed herein may be reversible or irreversible. A linker disclosed herein can be of formula II

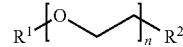

$$\tag{II}$$

wherein $R^1$ and $R^2$ are each independently H, OH, COOH, $NH_2$, $R^3OH$, $R^3COOH$, $OR^3OH$, $OR^3COOH$, $R^3NH(CO)R^4$, $R^3NH(CO)R^4OH$, $R^3NH(CO)R^4COOH$; $R^3$ and $R^4$ are each independently $C_{1-10}$ alkyl, $C_{2-10}$ alkenyl, or $C_{2-10}$ alkynyl; and n any integer from 0 to 10. An AR elimination promoter or elimination enhancer element disclosed herein can be a hydrophobic tag or an E3 ligase-recruiting moiety. A hydrophobic tag includes, without limitation, an adamantane moiety or a Boc-protected amino acid. An E3 ligase-recruiting moiety includes, without limitation, a hypoxia-inducible factor 1α (HIF-1α) moiety, a Nutlin moiety, a bestatin moiety, or a phthalimide moiety.

Other aspects of the present specification disclose a pharmaceutical composition comprising one or more compounds disclosed herein.

Other aspects of the present specification disclose a kit comprising one or more compounds disclosed herein or one or more pharmaceutical composition disclosed herein.

Other aspects of the present specification disclose a method of treating hair loss in an individual comprising the step of administering a therapeutically effective amount of a compound disclosed herein or a pharmaceutical composition disclosed herein. Aspects of the present specification also disclose a compound disclosed herein or a pharmaceutical composition disclosed herein for use in the treatment of hair loss; use of a compound disclosed herein or a pharmaceutical composition disclosed herein for the treatment of hair loss; and use of a compound disclosed herein or a pharmaceutical composition disclosed herein in the manufacture of a medicament for the treatment of hair loss.

Other aspects of the present specification disclose a method of treating hair thinning in an individual comprising the step of administering a therapeutically effective amount of a compound disclosed herein or a pharmaceutical composition disclosed herein. Aspects of the present specification also disclose a compound disclosed herein or a pharmaceutical composition disclosed herein for use in the treatment of hair thinning; use of a compound disclosed herein or a pharmaceutical composition disclosed herein for the treatment of hair thinning; and use of a compound disclosed herein or a pharmaceutical composition disclosed herein in the manufacture of a medicament for the treatment of hair thinning.

Other aspects of the present specification disclose a method of treating hair color loss in an individual comprising the step of administering a therapeutically effective amount of a compound disclosed herein or a pharmaceutical composition disclosed herein. Aspects of the present specification also disclose a compound disclosed herein or a pharmaceutical composition disclosed herein for use in the treatment of hair color loss; use of a compound disclosed herein or a pharmaceutical composition disclosed herein for the treatment of hair color loss; and use of a compound disclosed herein or a pharmaceutical composition disclosed herein in the manufacture of a medicament for the treatment of hair color loss.

Other aspects of the present specification disclose a method of treating a condition associated with a degenerative hair follicle disorder in an individual comprising the step of administering a therapeutically effective amount of a compound disclosed herein or a pharmaceutical composition disclosed herein. Aspects of the present specification also disclose a compound disclosed herein or a pharmaceutical composition disclosed herein for use in the treatment of a condition associated with a degenerative hair follicle disorder; use of a compound disclosed herein or a pharmaceutical composition disclosed herein for the treatment of a condition associated with a degenerative hair follicle disorder; and use of a compound disclosed herein or a pharmaceutical composition disclosed herein in the manufacture of a medicament for the treatment of a condition associated with a degenerative hair follicle disorder.

Other aspects of the present specification disclose a method of improving hair appearance in an individual comprising the step of administering a therapeutically effective amount of a compound disclosed herein or a pharmaceutical composition disclosed herein. Aspects of the present specification also disclose a compound disclosed herein or a pharmaceutical composition disclosed herein for use in improving hair appearance; use of a compound disclosed herein or a pharmaceutical composition disclosed herein for improving hair appearance; and use of a compound disclosed herein or a pharmaceutical composition disclosed herein in the manufacture of a medicament for improving hair appearance.

Other aspects of the present specification disclose a method of treating a skin condition in an individual comprising the step of administering a therapeutically effective amount of a compound disclosed herein or a pharmaceutical composition disclosed herein. Aspects of the present specification also disclose a compound disclosed herein or a pharmaceutical composition disclosed herein for use in the treatment of a skin condition; use of a compound disclosed herein or a pharmaceutical composition disclosed herein for the treatment of a skin condition; and use of a compound disclosed herein or a pharmaceutical composition disclosed herein in the manufacture of a medicament for the treatment of a skin condition

DETAILED DESCRIPTION

The skin is the outer covering of a mammalian body and guards the underlying muscles, bones, ligaments and internal organs. Typically the largest organ of the integumentary system, skin is composed of three primary layers: the epidermis, the dermis and the hypodermis. The epidermis is the outermost epithelial layer of the skin and forms the waterproof, protective wrap over the body's surface which also serves as a barrier to infection. The dermis is an epithelial layer of skin beneath the epidermis and serves to cushions the body from stress and strain. The hypodermis lies below the dermis and comprises loose connective tissue, adipose tissue and elastin. Although not composed of epithelial tissue, and thus not part of the skin, the hypodermis attaches the skin to underlying bone and muscle as well as supplying it with blood vessels and nerves.

Each hair comprises two structures: the hair shaft and the hair follicle. The hair shaft is primary composed of keratin that is organized into three layers called the medulla, cortex and cuticle. The medulla is the inner layer is not necessarily present in all hair types. The next keratin layer is the cortex, the intermediate layer that makes up the majority of the hair shaft. The outer layer is the cuticle, which is formed by tightly packed scales in an overlapping structure similar to roof shingles and is continuous with the root sheath. Most hair conditioning products attempt to affect the cuticle. Pigment cells, or melanocytes, are distributed throughout the cortex and medulla giving the hair its characteristic color. For purposes of the present disclosure, it is necessary to consider various types of hair, including, terminal hairs and vellus hairs and modified terminal hairs, such as seen in eye lashes and eyebrows. Terminal hairs are coarse, pigmented, long hairs in which the bulb of the hair follicle is seated deep in the dermis. Vellus hairs, on the other hand, are fine, thin, non-pigmented short hairs in which the hair bulb is located superficially in the dermis. As alopecia progresses, a transition takes place in the area of approaching baldness wherein the hairs themselves are changing from the terminal to the vellus type.

Located in the dermal layer of the skin, the hair follicle can be recognized as a separate entity within the skin with formation and maintenance based on interaction between dermal and epidermal components. The follicle comprises several components. At the base of the follicle is a projection called a dermal papilla, which contains capillaries that supply nutrients to the portion of the follicle called the bulb. The bulb can be divided into two regions: a lower region of undifferentiated cells, and an upper region of actively proliferating cells, called matrix cells, that differentiated to form the inner sheath and the hair shaft. Matrix cells are actively proliferating cells which differentiate and become keratinized to form the hair shaft. During epidermal cell differentiation (anagen phase), matrix cells divide every 23 to 72 hours, faster than any other cells in the body. Matrix cells located in the immediate vicinity of the dermal papilla differentiate and become keratinized to form the hair shaft, whereas matrix cells towards the periphery of a hair follicle proliferate and produce the inner root sheath. The follicle also contains two epidermal layers termed the inner root sheath and outer root sheath. These sheaths protect and mold the growing hair shaft. The inner root sheath can be divided into three layers (cuticle, Huxley layer, and Henle layer) based on structure, patterns of keratinization, and incorporation of trichohyalin. The inner sheath follows the hair shaft until it ends just below the level of a sebaceous gland to leave only the hair shaft to protrude above the epidermis. The outer root sheath continues all the way up to the gland and is distinct from other epidermal components of the hair follicle in that it is continuous with the epidermis. The sebaceous gland produces sebum, a natural oil that conditions the hair shaft and sometimes an apocrine (scent) gland. An erector pili muscle attaches below the gland to a fibrous layer around the outer sheath. The contraction of the muscle pulls on both the hair to make it erect and pulls on the skin making a bumpy surface. Hair color is caused by a pigment (melanin) that is produced by the hair follicle.

Under normal circumstances hair growth in each hair follicle occurs in a cycle that can comprise at least four phases: anagen (growth phase), catagen (regression phase), telogen (resting phase), and exogen (shedding phase). The anagen phase is the active growth phase of the hair during which the matrix cells in the root of the hair are dividing rapidly. About 80-90% of all hairs are in this phase at any time. Anagen hairs are anchored deeply into the subcutaneous fat and cannot be pulled out easily. When a new hair is formed, it pushes the club hair up the follicle and eventually out. During this phase the hair grows about 0.35 mm a day (1 cm every 28 days), but this rate varies depending on the site of the hair follicle and the age and sex of the individual. Human scalp hair stays in the active anagen phase of growth for 2-6 years, as compared to other sites like on the leg (which stays in the anagen phase for 19 to 26 weeks), on the arm (from 6 to 12 weeks), and in the mustache area, eyelashes, and eyebrows (from 4 to 14 weeks). Human subjects that have difficulty growing their hair beyond a certain length have a short active phase of growth. Human subjects that have very long hair have a long active phase of growth.

The catagen phase is a short transitional phase between the anagen and telogen phases which lasts only about 7-21 days. Although brief, this phase can be divided into eight subphases starting with late anagen and ending in early telogen. About 1-3% of all hairs are in this phase at any time. It is a period of controlled regression in which the hair follicle regresses and dismantles the hair growing part of the hair follicle, in part, through apoptosis. During this phase there is involution of the hair follicle and a fundamental restructuring of the extracellular matrix by 1) a withdrawal of dermal papilla and stoppage of hair growth, 2) cessation of matrix cell proliferation and melanocyte melanin synthesis, 3) shrinkage of the outer root sheath and attachment to the hair shaft, 4) movement of the lower hair follicle to the level of the arrector pili muscle, 5) movement of the dermal papilla upward through the skin, coming to rest beneath the hair-follicle bulge, and 6) cessation of protein and pigment production through programmed cell death keratinocyte and melanocytes. Also, there is massive apotosis in the bulbar, transient, portion of the hair follicle contributes to regression of the hair follicle and the formation of a fibrous streamer in the skin. The onset of these apoptotic events seems to be predetermined and finely orchestrated, and as such the events in this phase can be more appropriately described by the term, "programmed cell death".

The third phase is the telogen phase which, for all practical purposes, can be denominated a "resting phase." About 10-15% of all hairs are in this phase at any time. During this phase the hair follicle is stops dividing and the hair shaft ceases to grow, the telogen hair completes differentiation, and the last hair growth cells cluster together at the base of the hair shaft to form a club-structure comprising a centrally lying brush of keratinized cells surrounded by apparent mooring cells containing easily found, discrete nuclei and abundant cytoplasm. Called a club hair, the cluster of cells actually holds the hair shaft in the tube of hair follicle. In the final aspect of the telogen phase, a chemical signal causes matrix cells to initiate growth of a new hair shaft from the same hair follicle and the cycle starts over with a new anagen phase. Even though a telogen hair is located near the surface of the skin, it remains firmly anchored to the hair follicle. A telogen hair eventually sheds in the exogen phase and replaced by the next budding anagen hair. About 30-90 days elapse before telogen hair from the scalp sheds. The time period is much longer for hairs on the eyebrow, eyelash, arm and leg.

The final phase is the exogen, a phase marked by a highly controlled, active process where a telogen hair is actually shed from the follicle. The shed exogen hair has a shrunken base that is more elongated in shape and has a scalloped and pitted margin. Within this shaft base there is little associated cytoplasm and very few shrunken and fragmented nuclei. It is believed that the shrinkage of the hair club and disappears of the brush mooring allows the exogen hair to be shed from the follicle. Normally about 25-150 exogen hairs are shed each day.

Recently, an addition phase called kenogen has been proposed. This phase describes the interval of the hair cycle in which the hair follicle remains empty after the telogen hair has been extruded, but before a new anagen hair reappears.

Androgens, mainly testosterone and 5α-dihydrotestosterone (DHT) play significant role in the growth and development of the male reproductive organs. These steroid hormones bring about their biological functions through their associations with Androgen receptor (AR). Also known as nuclear receptor subfamily 3, group C, member 4 (NR3C4), AR is a 110 KDa ligand dependent transcription factor that falls under the group of nuclear receptor superfamily. AR has four functional domains, an N terminal domain (NTD), a DNA binding domain (DBD), a hinge region and a Ligand binding Domain (LBD). The DBD has ZNF motifs which allows it bind to DNA. The rest of the domains are involved in dimerization and ligand binding. An AR is most closely related to the progesterone receptor, and progestins in higher dosages can block AR. AR is found to be expressed in a number of tissues and cells including prostate, testis, seminal vescicle, epididymis, skin, skeletal muscle, cardiac muscle, liver and central nervous system. The main function of the AR receptor is as a DNA-binding transcription factor that regulates gene expression, including genes critical for the development and maintenance of the male sexual phenotype.

In the ligand unbound state, an AR is an inactive cytosolic protein, which is complex with various heat-shock proteins including Hsp70, Hsp90 and Hsp 56 as well as p23. Upon ligand binding, two critical phosphorylation events promote a conformational change to an AR, resulting in the release the LBD for hormone binding and disassociation of the ligand-bound AR from the Hsp complex. The complex-free ligand-bound AR translocates into the nucleus, forms homodimers, and binds to the androgen-response elements (AREs) present on various target genes, thereby activating gene expression. Temporal and spatial expression can be regulated in part by many co-regulators which bind to ligand-bound AR homodimers at different time points and in different cell types. For example, modulation of AR activity can be carried out by several transcription factors like ARA70, TR4, SRC family members and CBP/p300 and other associated proteins. FXXLF and WXXLF motifs containing coactivators such as the p160 members bind with the AF2 region of the LBD of an AR.

AR activity also drives hair loss, hair thinning, or hair color loss. For example, the dermal papilla is the master regulator of the hair cycle and this structure has AR. DHT exposure to follicles on the vertex and frontal region of the scalp can suppress hair growth in part by dramatically shortening the length of anagen to point where the hair follicle exists only in a miniaturized state of extended telogen. In addition, testosterone is converted to DHT in the follicle via the enzymatic activity of Type II 5-alpha reductase. Further, androgenic alopecia is a common form of hair loss that begins to manifest itself in males following the onset of puberty and increasing in frequency with each decade of life. In the balding scalp of men levels of both AR and DHT are about 2-times higher than AR and DHT levels observed in non-balding scalp. Thus, although modulated by both genetic and environmental variables, the primary attribute of androgenic alopecia is increased AR signaling resulting in the progressive shortening of the hair growth cycle in the hair follicle. It should be noted that female alopecia also occurs and it thought to be regulated by factors similar to those involved with androgenic alopecia. Thus, targeting AR in a manner that reduces, suppresses or eliminates its signaling capabilities will prevent the progression of factors that drive hair loss, hair thinning, or hair color loss.

AR activity also drives certain skin conditions, disease and disorders such as, e.g., acne. Acne, also known as acne vulgaris, is a long-term skin disease that occurs when hair follicles are clogged with dead skin cells and oil from the skin. It is characterized by blackheads or whiteheads, pimples, greasy skin, and possible scarring. Acne primarily affects areas of the skin with a relatively high number of oil glands, including the face, upper part of the chest, and back. The resulting appearance can lead to anxiety, reduced self-esteem and, in extreme cases, depression or thoughts of suicide. During puberty, an increase in androgens in both males and females cause skin follicle glands to grow larger and produce more oily sebum. Acne has been linked to increased exposure to testosterone, DHT, and dehydroepiandrosterone (DHEA), and such androgens appear to be essential for acne to occur, as acne does not develop in individuals with complete androgen insensitivity syndrome (CAIS). Thus, targeting AR in a manner that reduces, suppresses or eliminates its signaling capabilities will prevent the progression of factors that drive skin conditions, diseases and disorders such as acne or another AR signal-mediated skin condition, disease or disorder.

Besides being one of the most common skin disorders, acne is also a cardinal component of many systemic diseases or syndromes. Their association illustrates the nature of these diseases and is indicative of the pathogenesis of acne. Congenital adrenal hyperplasia (CAH) and seborrhoea-acne-hirsutism-androgenetic alopecia (SAHA) syndrome highlight the role of androgen steroids, while polycystic ovary (PCO) and hyperandrogenism-insulin resistance-acanthosis *nigricans* (HAIR-AN) syndromes indicate insulin resistance in acne. Apert syndrome with increased fibroblast growth factor receptor 2 (FGFR2) signalling results in follicular hyperkeratinization and sebaceous gland hypertrophy in acne. Synovitis-acne-pustulosis-hyperostosis-osteitis (SAPHO) and pyogenic arthritis-pyoderma gangrenosum-acne (PAPA) syndromes highlight the attributes of inflammation to acne formation.

The present specification discloses tripartite androgen receptor eliminators (AREs) which comprises an AR antagonist linked to a molecule that marks the AR antagonist for proteasome degradation. Thus, the disclosed AREs have the ability to both antagonize AR activity and trigger the degradation of this receptor. The AREs disclosed herein effectively penetrate the skin and/or scalp when topically applied to trigger cellular AR clearance, thereby resulting in the treatment of skin and hair conditions, diseases and disorders mediated by AR signaling, including, without limitation hair problems such as androgenic alopecia and facial hirsutism and/or skin problems such as acne, excessive sebum production, and post-wound scar formation.

Without wishing to be bound by any particular theory, it is thought that the disclosed AREs, compositions comprising one or more AREs, and methods and uses of such compositions reduce or prevent a hair condition, disease or disorder mediated by AR signaling in order to reduce or prevent hair loss, hair thinning, and/or hair color loss mediated by AR signaling. This can be accomplished, without limitation, by reducing, suppressing or inhibiting AR signaling in a hair follicle, reducing or eliminating AR in the cytoplasm of a follicle and/or dermal papilla, inducing a hair follicle into the anagen phase and/or stimulating the matrix cells to form a new hair shaft, by prolonging the time period a hair follicle remains in anagen phase thereby enabling the follicle to produce a longer and/or thicker hair shaft, by increasing keratin deposition thereby producing a longer and/or thicker hair shaft, by increasing melanin deposition thereby darkening hair shaft color, by preventing or prolonging the catagen phase thereby increasing the time a hair remains in a follicle, by prolonging the time period a hair follicle remains in telogen phase thereby increasing the time a hair remains in a follicle, by preventing the follicle to enter the exogen phase thereby stopping the release of the hair shaft, by stopping hair shaft release in the exogen phase thereby increasing the number of hairs and/or by stimulating new hair shaft growth thereby allowing the production of two or more hair shafts per follicle, and/or by increasing the conversion of intermediate hairs into terminal hairs. Therefore, at any given time during treatment, there are more hairs in follicles and decreased hair loss. The result is not only an increase in length, thickness and/or darkness of hairs, but also an increase in the number and/or density of hairs.

In addition, without wishing to be bound by any particular theory, it is thought that the disclosed AREs, compositions comprising one or more AREs, and methods and uses of such compositions reduce or prevent a skin condition, disease or disorder mediated by AR signaling. This can be accomplished, without limitation, by reducing, suppressing or inhibiting AR signaling in a skin follicle, and reducing or eliminating AR in the cytoplasm of a cell. Therefore, at any given time during treatment, the symptoms or unwanted attributes of a skin condition, disease or disorder are reduced, suppressed or eliminated.

The present specification discloses, in part, a tripartite androgen receptor eliminator (ARE). AN ARE comprises an AR antagonist, a linker molecule and an AR elimination promoter or elimination enhancer element. In one embodiment, an ARE is of formula I:

ARA-L-EE      (I)

wherein ARA is an AR antagonist, L is a linker molecule and EE is an AR elimination promoter or elimination enhancer element.

The present specification discloses, in part, an AR receptor antagonist. An AR antagonist, also called an AR blocker, reduces or prevents agonist-mediated responses mediated by an AR, rather than provoking a biological response itself upon binding to an AR. Thus, an AR antagonist has affinity but no efficacy for its cognate AR, and binding will disrupt the interaction and inhibit the function of an AR agonist or an inverse AR agonist at an AR. An AR antagonist disclosed herein can mediate its effects by binding to an active orthosteric site or by binding to an allosteric site on an AR, or an AR antagonist disclosed herein may interact at unique binding sites not normally involved in the biological regulation of AR activity. An AR antagonist disclosed herein may be reversible or irreversible depending on the longevity of the antagonist-receptor complex, which, in turn, depends on the nature of antagonist-receptor binding. Without wishing to be limited to any one theory, AR degradation in cells can be triggered by disrupting the HSP90/AR complex in the cytoplasm, thereby causing AR clearance via the proteasome.

In one embodiment, an AR antagonist disclosed herein is flutamide, nilutamide, bicalutamide, enzalutamide, apalutamide, cyproterone acetate, megestrol acetate, chlormadinone acetate, spironolactone, canrenone, drospirenone, ketoconazole, topilutamide (fluridil), or cimetidine. In an aspect of this embodiment, an AR antagonist disclosed herein is spironolactone, ketoconazole, methoxybenzyl lactam, RU58841 or Compound ARA1.

Shaposhnik. Tripartite Androgen Receptor Eliminators. Methods and Uses Thereof

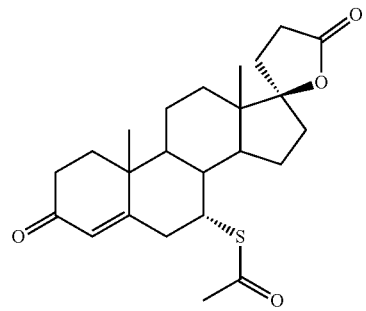 [SMILES: CC(=O)S[C@@H]1CC2=CC(=O)CCC2(C)C2CCC3(C)C(CC[C@@]34CCC(=O)O4)C21]

Spironolactone

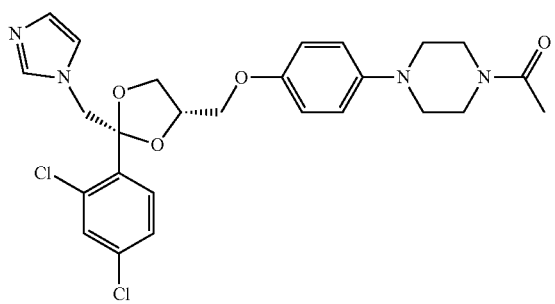 [SMILES: CC(=O)N1CCN(c2ccc(OC[C@H]3CO[C@](Cn4ccnc4)(c4ccc(Cl)cc4Cl)O3)cc2)CC1]

Ketoconazole

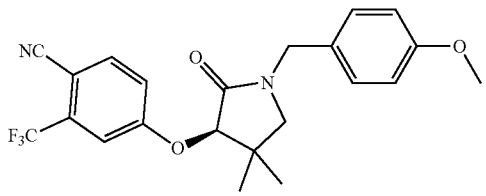 [SMILES: COc1ccc(CN2CC(C)(C)[C@@H](Oc3ccc(C#N)c(C(F)(F)F)c3)C2=O)cc1]

Methoxybenzyl lactam

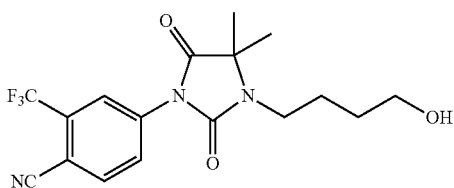 [SMILES: CC1(C)C(=O)N(c2ccc(C#N)c(C(F)(F)F)c2)C(=O)N1CCCCO]

RU58841

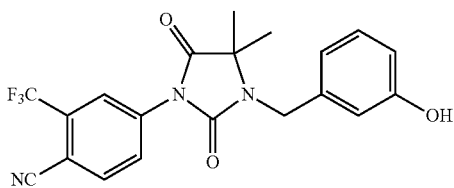 [SMILES: CC1(C)C(=O)N(c2ccc(C#N)c(C(F)(F)F)c2)C(=O)N1Cc1cccc(O)c1]

Compound ARA1

Other antagonists useful as an AR antagonist disclosed herein are described in, e.g., U.S. Pat. Nos. 6,790,979; 8,198,323; Hu, et al., Synthesis and Biological Evaluation of Amino-Pyridines as Androgen Receptor Antagonists for Stimulating Hair Growth and Reducing Sebum Production, Bioorg. Med. Chem. Lett. 17:5693-5697 (2007); Hu, et al., (1R,2S)-4-(2-Cyano-cydohexyl-oxy)-2-trifluoromethy 1-benzonittile, a Potent Androgen Receptor Antagonists for Stimulating Hair Growth and Reducing Sebum Production, Bioorg. Med. Chem. Lett. 17:5983-5988 (2007); Mitchell, et al., Rational Design of a Topical Androgen Receptor Antagonist for the Suppression of Sebum. Production with Properties Suitable for Follicular Delivery, J. Med. Chem. 53:4422-4427 (2010), each of which is incorporated by reference in its entirety.

The present specification discloses, in part, a linker. A linker disclosed herein is a molecule that directly or indirectly attaches an androgen receptor antagonist to an AR elimination promoter or elimination enhancer element. Typically, this attachment is a covalent attachment.

In one embodiment, a linker molecule is of formula II:

(II)

wherein $R^1$ and $R^2$ are each independently H, OH, COOH, $NH_2$, $R^3OH$, $R^3COOH$, $OR^3OH$, $OR^3COOH$, $R^3NH(CO)$ $R^4$, $R^3NH(CO)$ $R^4OH$, $R^3NH(CO)$ $R^4COOH$; $R^3$ and $R^4$ are each independently $C_{1-10}$ alkyl, $C_{2-10}$ alkenyl, or $C_{2-10}$ alkynyl; and n any integer from 0 to 10. An alkyl functional group comprising a straight-chain or branched-chain hydrocarbon linked exclusively by single bonds and not having any cyclic structure. An alkenyl functional group comprising a straight-chain or branched-chain hydrocarbon having one or more carbon-carbon double bonds and not having any cyclic structure. An alkynyl functional group comprising a straight-chain or branched-chain hydrocarbon having one or more carbon-carbon triple bonds and not having any cyclic structure.

In aspects of this embodiment, a linker molecule disclosed herein is of formula II, wherein $R^1$ and $R^2$ are each independently H, OH, COOH, $NH_2$, $R^3OH$, $R^3COOH$, $OR^3OH$, $OR^3COOH$, $R^3NH(CO)$ $R^4$, $R^3NH(CO)$ $R^4OH$, or $R^3NH(CO)$ $R^4COOH$; $R^3$ and $R^4$ are each independently $C_{1-6}$ alkyl, $C_{2-6}$ alkenyl, or $C_{2-6}$ alkynyl; and n any integer from 0 to 10. In other aspects of this embodiment, a linker molecule disclosed herein is of formula II, wherein $R^1$ and $R^2$ are each independently H, OH, COOH, $NH_2$, $R^3OH$, $R^3COOH$, $OR^3OH$, $OR^3COOH$, $R^3NH(CO)$ $R^4$, $R^3NH(CO)$ $R^4OH$, or $R^3NH(CO)$ $R^4COOH$; $R^3$ and $R^4$ are each independently $C_{1-4}$ alkyl, $C_{2-4}$ alkenyl, or $C_{2-4}$ alkynyl; and n any integer from 0 to 5. In yet aspects of this embodiment, a linker molecule disclosed herein is of formula II, wherein $R^1$ and $R^2$ are each independently H, OH, COOH, $NH_2$, $R^3OH$, $R^3COOH$, $OR^3OH$, $OR^3COOH$, or $R^3NH(CO)$ $R^4OH$; $R^3$ and $R^4$ are each independently $C_{1-10}$ alkyl; and n any integer from 0 to 10. In still other aspects of this embodiment, a linker molecule disclosed herein is of formula II, wherein $R^1$ and $R^2$ are each independently H, OH, COOH, $NH_2$, $R^3OH$, $R^3COOH$, $OR^3OH$, $OR^3COOH$, or $R^3NH(CO)$ $R^4OH$; $R^3$ and $R^4$ are each independently $C_{1-6}$ alkyl; and n any integer from 0 to 10. In other aspects of this embodiment, a linker molecule disclosed herein is of formula II, wherein $R^1$ and $R^2$ are each independently H, OH, COOH, $NH_2$, $R^3OH$, $R^3COOH$, $OR^3OH$, $OR^3COOH$, or $R^3NH(CO)$ $R^4OH$; $R^3$ and $R^4$ are each independently $C_{1-6}$ alkyl; and n any integer from 0 to 5.

In aspects of this embodiment, a linker molecule disclosed herein is of formula II, wherein $R^1$ is OH, COOH, $NH_2$, $R^3OH$, $R^3COOH$, or $R^3NH(CO)$ $R^4OH$; $R^2$ is OH, COOH, NH$_2$, R$^3$COOH, or OR$^3$COOH, R$^3$ and R$^4$ are each independently C$_{1-10}$ alkyl; and n any integer from 0 to 10. In other aspects of this embodiment, a linker molecule disclosed herein is of formula II, wherein R$^1$ is OH, COOH, NH$_2$, R$^3$OH, R$^3$COOH, or R$^3$NH(CO) R$^4$OH; R$^2$ is OH, COOH, NH$_2$, R$^3$COOH, or OR$^3$COOH, R$^3$ and R$^4$ are each independently C$_{1-6}$ alkyl; and n any integer from 0 to 10. In yet other aspects of this embodiment, a linker molecule disclosed herein is of formula II, wherein R$^1$ is OH, COOH, NH$_2$, R$^3$OH, R$^3$COOH, or R$^3$NH(CO) R$^4$OH; R$^2$ is OH, COOH, NH$_2$, R$^3$COOH, or OR$^3$COOH, R$^3$ and R$^4$ are each independently C$_{1-6}$ alkyl; and n any integer from 0 to 5. In still other aspects of this embodiment, a linker molecule disclosed herein is of formula II, wherein R$^1$ is OH, R$^3$OH, R$^3$COOH, or R$^3$NH(CO) R$^4$OH; R$^2$ is OH, COOH, NH$_2$, R$^3$COOH, or OR$^3$COOH, R$^3$ and R$^4$ are each independently C$_{1-6}$ alkyl; and n any integer from 0 to 5. In other aspects of this embodiment, a linker molecule disclosed herein is of formula II, wherein R$^1$ is OH, R$^3$OH, R$^3$COOH, or R$^3$NH (CO) R$^4$OH; R$^2$ is OH, COOH, NH$_2$, R$^3$COOH, or OR$^3$COOH, R$^3$ and R$^4$ are each independently C$_{1-4}$ alkyl; and n any integer from 0 to 4.

In aspects of this embodiment, a linker molecule disclosed herein is of formula II, wherein R$^1$ is OH, C—C—OH, C—COOH, or C—C—NH—CO—C—C—C—OH; R$^2$ is OH, COOH, NH$_2$, C—COOH, or O—C—COOH; and n any integer from 0 to 10. In other aspects of this embodiment, a linker molecule disclosed herein is of formula II, wherein R$^1$ is OH, C—C—OH, C—COOH, or C—C—NH—CO—C—C—C—OH; R$^2$ is OH, COOH, NH$_2$, C—COOH, or O—C—COOH; and n any integer from 0 to 8. In yet other aspects of this embodiment, a linker molecule disclosed herein is of formula II, wherein R$^1$ is OH, C—C—OH, C—COOH, or C—C—NH—CO—C—C—C—OH; R$^2$ is OH, COOH, NH$_2$, C—COOH, or O—C—COOH; and n any integer from 0 to 6. In still other aspects of this embodiment, a linker molecule disclosed herein is of formula II, wherein R$^1$ is OH, C—C—OH, C—COOH, or C—C—NH—CO—C—C—C—OH; R$^2$ is OH, COOH, NH$_2$, C—COOH, or O—C—COOH; and n any integer from 0 to 4.

In other aspects of this embodiment, a linker molecule disclosed herein is of formula III:

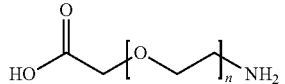
(III)

wherein n any integer from 0 to 10. In aspects of this embodiment, a linker molecule disclosed herein is of formula III, wherein n any integer from 0 to 8. In yet other aspects of this embodiment, a linker molecule disclosed herein is of formula III, wherein n any integer from 0 to 6. In still other aspects of this embodiment, a linker molecule disclosed herein is of formula III, wherein n any integer from 0 to 4. In other aspects of this embodiment, a linker molecule disclosed herein of formula III is

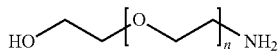,
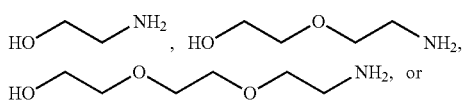

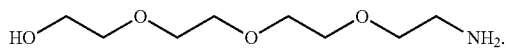.

In other aspects of this embodiment, a linker molecule disclosed herein is of formula IV:

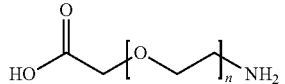
(IV)

wherein n any integer from 0 to 10. In aspects of this embodiment, a linker molecule disclosed herein is of formula IV, wherein n any integer from 0 to 8. In yet other aspects of this embodiment, a linker molecule disclosed herein is of formula IV, wherein n any integer from 0 to 6. In still other aspects of this embodiment, a linker molecule disclosed herein is of formula IV, wherein n any integer from 0 to 4. In other aspects of this embodiment, a linker molecule disclosed herein of formula IV is

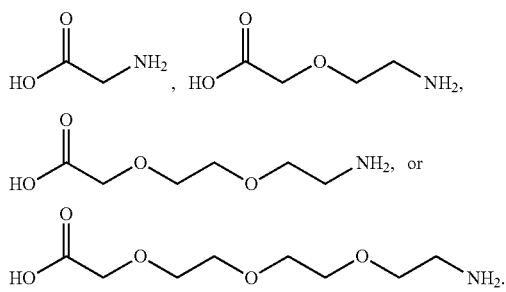

In other aspects of this embodiment, a linker molecule disclosed herein is of formula V:

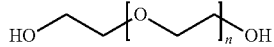
(V)

wherein n any integer from 0 to 10. In aspects of this embodiment, a linker molecule disclosed herein is of formula V, wherein n any integer from 0 to 8. In yet other aspects of this embodiment, a linker molecule disclosed herein is of formula V, wherein n any integer from 0 to 6. In still other aspects of this embodiment, a linker molecule disclosed herein is of formula V, wherein n any integer from 0 to 4. In other aspects of this embodiment, a linker molecule disclosed herein of formula V is

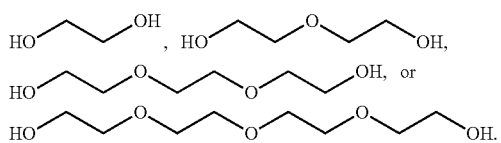

In other aspects of this embodiment, a linker molecule disclosed herein is of formula VI:

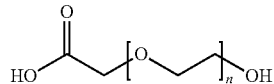

(VI)

wherein n any integer from 0 to 10. In aspects of this embodiment, a linker molecule disclosed herein is of formula VI, wherein n any integer from 0 to 8. In yet other aspects of this embodiment, a linker molecule disclosed herein is of formula VI, wherein n any integer from 0 to 6. In still other aspects of this embodiment, a linker molecule disclosed herein is of formula VI, wherein n any integer from 0 to 4. In other aspects of this embodiment, a linker molecule disclosed herein of formula VI is

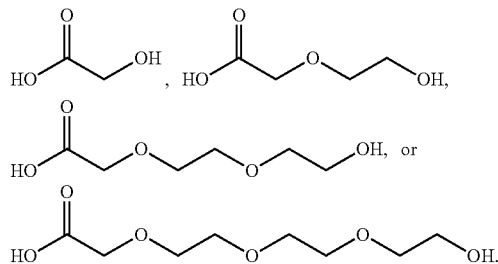

In other aspects of this embodiment, a linker molecule disclosed herein is of formula VII:

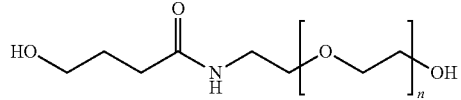

(VII)

wherein n any integer from 0 to 10. In aspects of this embodiment, a linker molecule disclosed herein is of formula VII, wherein n any integer from 0 to 8. In yet other aspects of this embodiment, a linker molecule disclosed herein is of formula VII, wherein n any integer from 0 to 6. In still other aspects of this embodiment, a linker molecule disclosed herein is of formula VII, wherein n any integer from 0 to 4. In other aspects of this embodiment, a linker molecule disclosed herein of formula VII is

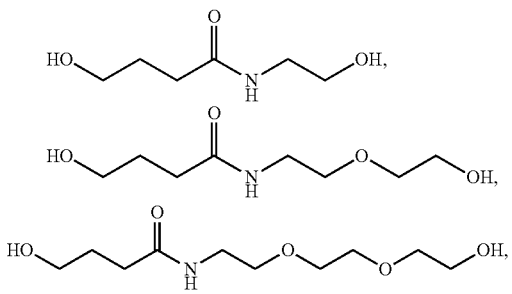 or

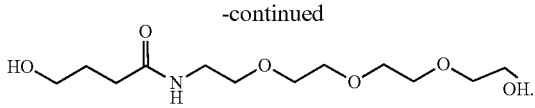

In other aspects of this embodiment, a linker molecule disclosed herein is of formula VIII:

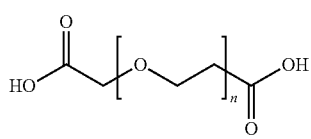

(VIII)

wherein n any integer from 0 to 10. In aspects of this embodiment, a linker molecule disclosed herein is of formula VIII, wherein n any integer from 0 to 8. In yet other aspects of this embodiment, a linker molecule disclosed herein is of formula VIII, wherein n any integer from 0 to 6. In still other aspects of this embodiment, a linker molecule disclosed herein is of formula VIII, wherein n any integer from 0 to 4. In other aspects of this embodiment, a linker molecule disclosed herein of formula VIII is

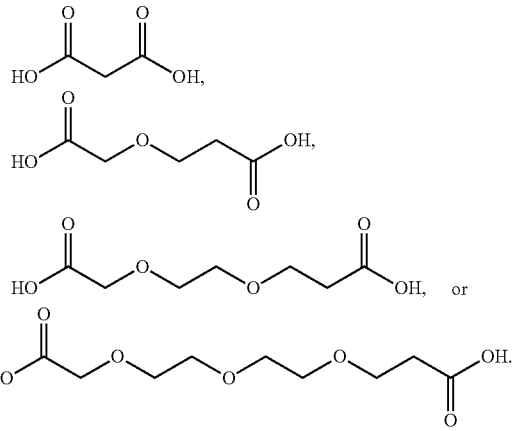

In other aspects of this embodiment, a linker molecule disclosed herein is of formula IX:

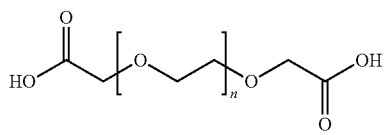

(IX)

wherein n any integer from 0 to 10. In aspects of this embodiment, a linker molecule disclosed herein is of formula IX, wherein n any integer from 0 to 8. In yet other aspects of this embodiment, a linker molecule disclosed herein is of formula IX, wherein n any integer from 0 to 6. In still other aspects of this embodiment, a linker molecule disclosed herein is of formula IX, wherein n any integer from 0 to 4. In other aspects of this embodiment, a linker molecule disclosed herein of formula IX is

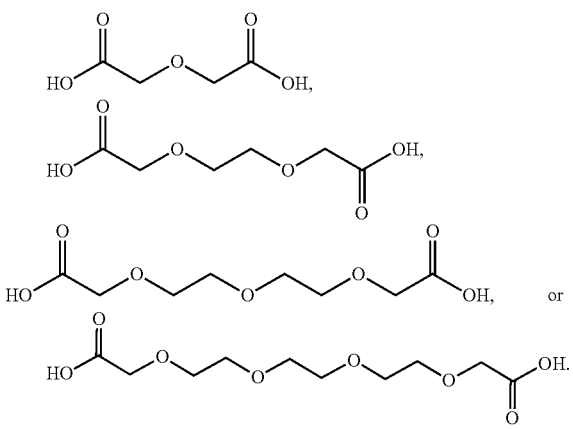

In other aspects of this embodiment, a linker molecule disclosed herein is of formula X:

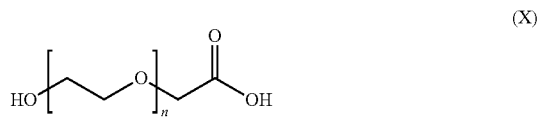

(X)

wherein n any integer from 0 to 10. In aspects of this embodiment, a linker molecule disclosed herein is of formula X, wherein n any integer from 0 to 8. In yet other aspects of this embodiment, a linker molecule disclosed herein is of formula X, wherein n any integer from 0 to 6. In still other aspects of this embodiment, a linker molecule disclosed herein is of formula X, wherein n any integer from 0 to 4. In other aspects of this embodiment, a linker molecule disclosed herein of formula X is

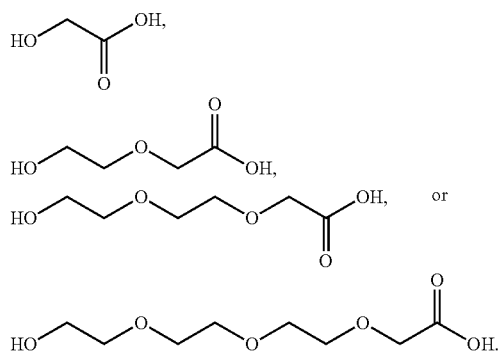

The present specification discloses, in part, an AR elimination promoter or elimination enhancer element. An AR elimination promoter or elimination enhancer element disclosed herein targets, induces, facilitates or otherwise marks a polypeptide linked to the AR elimination promoter or elimination enhancer element as a polypeptide that should be degraded, destroyed or otherwise made inactive or non-functional. In one embodiment, an AR elimination promoter or elimination enhancer element disclosed herein targets, facilitates or otherwise marks a polypeptide for the proteasomal degradation pathway. In an aspect of this embodiment, an AR elimination promoter or elimination enhancer element disclosed herein targets, facilitates or otherwise marks a polypeptide for degradation by a proteasome using an ubiquitin-independent pathway. In another aspect of this embodiment, an AR elimination promoter or elimination enhancer element disclosed herein targets, facilitates or otherwise marks a polypeptide for degradation by a proteasome using an ubiquitin-dependent pathway.

In one embodiment, an AR elimination promoter or elimination enhancer element is a hydrophobic tag. A hydrophobic tag is a molecule that appears to destabilize a polypeptide, thereby resulting in the recruitment of one or more chaperones to an unfolded polypeptide. The destabilized protein is then transported to proteasomes where it is degraded. Degradation using a hydrophobic tag appears to be an ubiquitin-independent process. Examples of a hydrophobic tag is an adamantane moiety and a butyl carbamate (Boc)-protected amino acid.

In one aspect of this embodiment, a hydrophobic tag is an adamantane moiety. An adamantane moiety disclosed herein comprises a $C_{10}H_{16}$ cycloalkane arranged in an "armchair" configuration of four connected cyclohexane rings. A boat-shaped configuration can also exist. In aspects of this embodiment, an adamantane is of formula XI:

(XI)

wherein $R^5$ is H, OH, COOH, $NH_2$, a halogen, $R^6OH$, $R^6COOH$, $R^6C(O) NH_2$, or $R^6C(O) R^7$; $R^6$ is $C_{1-10}$ alkyl, $C_{2-10}$ alkenyl, or $C_{2-10}$ alkynyl; and $R^7$ is a halogen. A halogen refers to a nonmetal element including fluorine (F), chlorine (Cl), bromine (Br), iodine (I), astatine (At) and ununseptium (Uus). In aspects of this embodiment, an adamantane moiety disclosed herein is of formula XI, wherein $R^5$ is H, OH, COOH, $NH_2$, a halogen, $R^6OH$, $R^6COOH$, $R^6C(O) NH_2$ or $RC(O) R^7$; $R^6$ is $C_{1-6}$ alkyl, $C_{2-6}$ alkenyl, or $C_{2-6}$ alkynyl; and $R^7$ is a halogen. In other aspects of this embodiment, an adamantane moiety disclosed herein is of formula XI, wherein $R^5$ is H, OH, COOH, $NH_2$, a halogen, $R^6OH$, $R^6COOH$, $R^6C(O) NH_2$ or $R^6C(O) R^7$; $R^6$ is $C_{1-4}$ alkyl, $C_{2-4}$ alkenyl, or $C_{2-4}$ alkynyl; and $R^7$ is a halogen. In yet other aspects of this embodiment, an adamantane moiety disclosed herein is of formula XI, wherein $R^5$ is H, OH, COOH, $NH_2$, F, Br, Cl, I, $R^6OH$, $R^6COOH$, $R^6C(O) NH_2$ or $R^6C(O) R^7$; $R^6$ is $C_{1-6}$ alkyl, $C_{2-6}$ alkenyl, or $C_{2-6}$ alkynyl; and $R^7$ is a F, Br, Cl or I. In still other aspects of this embodiment, an adamantane moiety disclosed herein of formula XI is

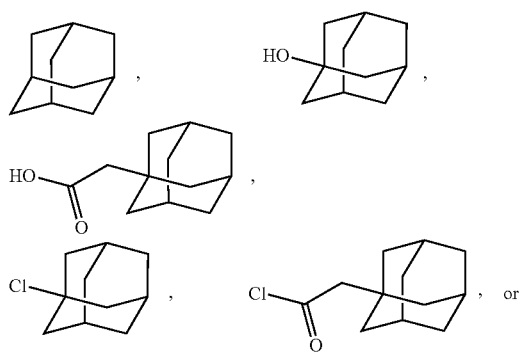

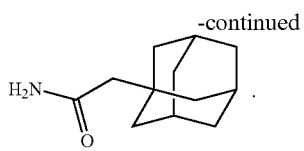

In another aspect of this embodiment, a hydrophobic tag is a Boc-protected amino acid. A Boc-protected amino acid induces protein degradation by taking advantage of the N-end rule pathway, where the half-life of a polypeptide is determined by the specific N-terminal amino acid present. The following amino acids all confer half-life of less than 90 minutes to a polypeptide: glutamine, arginine, glutamic acid, phenylalanine, aspartic acid, cysteine, lysine and asparagine. In aspects of this embodiment, a hydrophobic tag is a tert-butyl carbamate-protected arginine ($BOC_3Arg$) moiety, an iso-butyl carbamate-protected lysine ($BOC_2Lys$) moiety, an iso-butyl carbamate-protected aspartic acid ($BOC_2Asp$) moiety, an iso-butyl carbamate-protected asparagine ($BOC_2Asn$) moiety, an iso-butyl carbamate-protected glutamic acid ($BOC_2Glu$) moiety, and an iso-butyl carbamate-protected glutamine ($BOC_2Gln$) moiety. In aspects of this embodiment, a hydrophobic tag is

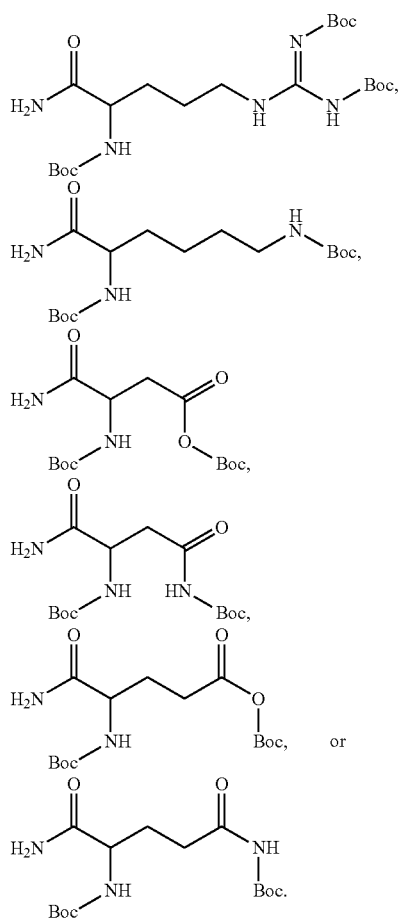

Additional hydrophobic tags useful as an AR elimination promoter or elimination enhancer element disclosed herein are described in, e.g., Neklesa, et al., Small-Molecule Hydrophobic Tagging Induced Degradation of HaloTag Fusion Proteins, Nat. Chem. Biol. 7 (8): 538-543 (2012), which is hereby incorporated by reference in its entirety.

In one embodiment, an AR elimination promoter or elimination enhancer element is an E3 ligase-recruiting moiety. An E3 ligase-recruiting moiety recruits an ubiquitin E3 ligase to ubiquitylate a polypeptide of interest, thereby making the entire complex for degradation via the ubiquitination pathway. Degradation using an E3 ligase-recruiting moiety is an ubiquitin-dependent process.

In one aspect of this embodiment, an E3 ligase-recruiting moiety is a hypoxia-inducible factor 1α (HIF-1α) moiety. E3 ligase recognizes a core hydroxylated proline in a seven-amino-acid recognition sequence of hypoxia-inducible factor 1α (HIF-1α). In an aspect of this embodiment, a HIF-1α moiety is formula XII

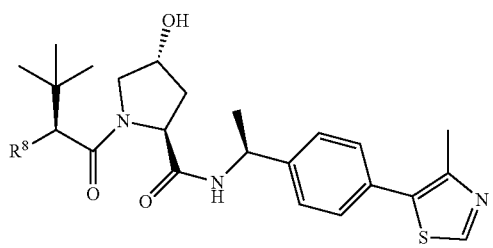

(XII)

wherein $R^8$ is H, OH, COOH, $NH_2$, a halogen, $R^9OH$, $R^9COOH$, $R^6C(O)$ $NH_2$, or $R^6C(O)$ $R^{10}$; $R^9$ is $C_{1-10}$ alkyl, $C_{2-10}$ alkenyl, or $C_{2-10}$ alkynyl; and $R^{10}$ is a halogen. In aspects of this embodiment, a HIF-1α moiety disclosed herein is of formula XII, wherein $R^8$ is H, OH, COOH, $NH_2$, a halogen, $R^9OH$, $R^9COOH$, $R^6C(O)$ $NH_2$, or $R^6C(O)$ $R^{10}$; $R^9$ is $C_{1-6}$ alkyl, $C_{2-6}$ alkenyl, or $C_{2-6}$ alkynyl; and $R^{10}$ is a halogen. In other aspects of this embodiment, a HIF-1α moiety disclosed herein is of formula XII, wherein $R^8$ is H, OH, COOH, $NH_2$, a halogen, $R^9OH$, $R^9COOH$, $R^6C(O)$ $NH_2$, or $R^6C(O)$ $R^{10}$; $R^9$ is $C_{1-4}$ alkyl, $C_{2-4}$ alkenyl, or $C_{2-4}$ alkynyl; and $R^{10}$ is a halogen. In yet other aspects of this embodiment, a HIF-1α moiety disclosed herein is of formula XII, wherein $R^8$ is H, OH, COOH, $NH_2$, F, Br, Cl, I, ROH, $R^9COOH$, $R^6C(O)$ $NH_2$, or $R^6C(O)$ $R^{10}$; $R^9$ is $C_{1-6}$ alkyl, $C_{2-6}$ alkenyl, or $C_{2-6}$ alkynyl; and $R^{10}$ is a F, Br, Cl or I. In still other aspects of this embodiment, a HIF-1α moiety disclosed herein of formula XII is

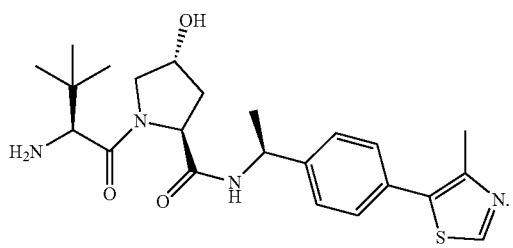 [SMILES: Cc1ncsc1-c1ccc([C@H](C)NC(=O)[C@@H]2C[C@@H](O)CN2C(=O)[C@@H](N)C(C)(C)C)cc1]

In another aspect of this embodiment, an E3 ligase-recruiting moiety is a Nutlin moiety. A Nutlin moiety is a cis-imidazoline analog that inhibit the interaction between mouse double minute 2 (MDM2) and tumor suppressor p53. A Nutlin moiety includes a Nutlin-1 moiety, a Nutlin-2 moiety and a Nutlin-3 moiety. In an aspect of this embodiment, a Nutlin moiety is formula XIII

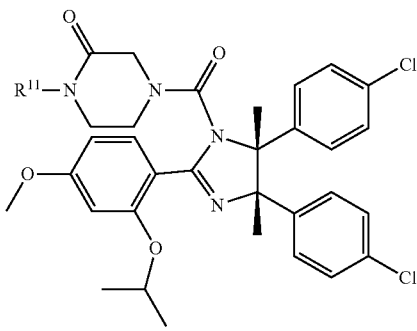

(XIII)

wherein $R^{11}$ is H, OH, COOH, $NH_2$, a halogen, $R^{12}OH$, $R^{12}COOH$, $R^{12}C(O)$ $NH_2$, or $R^{12}C(O)$ $R^{13}$; $R^{12}$ is $C_{1-10}$ alkyl, $C_{2-10}$ alkenyl, or $C_{2-10}$ alkynyl; and $R^{13}$ is a halogen. In aspects of this embodiment, a Nutlin moiety disclosed herein is of formula XIII, wherein $R^{11}$ is H, OH, COOH, $NH_2$, a halogen, $R^{12}OH$, $R^{12}COOH$, $R^{12}C(O)$ $NH_2$, or $R^{12}C(O)$ $R^{13}$; $R^{12}$ is $C_{1-6}$ alkyl, $C_{2-6}$ alkenyl, or $C_{2-6}$ alkynyl; and $R^{13}$ is a halogen. In other aspects of this embodiment, a Nutlin moiety disclosed herein is of formula XIII, wherein $R^{11}$ is H, OH, COOH, $NH_2$, a halogen, $R^{12}OH$, $R^{12}COOH$, $R^{12}C(O)$ $NH_2$, or $R^{12}C(O)$ $R^{13}$; $R^{12}$ is $C_{1-4}$ alkyl, $C_{2-4}$ alkenyl, or $C_{2-4}$ alkynyl; and $R^{13}$ is a halogen. In yet other aspects of this embodiment, a Nutlin moiety disclosed herein is of formula XIII, wherein $R^{11}$ is H, OH, COOH, $NH_2$, F, Br, Cl, I, $R^{12}OH$, $R^{12}COOH$, $R^{12}C(O)$ $NH_2$, or $R^{12}C(O)$ $R^{13}$; $R^{12}$ is $C_{1-6}$ alkyl, $C_{2-6}$ alkenyl, or $C_{2-6}$ alkynyl; and $R^{13}$ is a F, Br, Cl or I.

In another aspect of this embodiment, an E3 ligase-recruiting moiety is a bestatin moiety. A bestatin (also known as ubenimex) moiety is a competitive, reversible protease inhibitor. In an aspect of this embodiment, a bestatin moiety is formula XIV

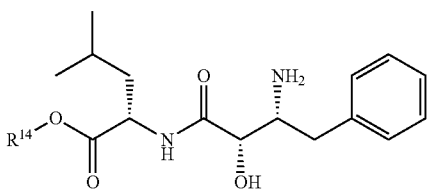

(XIV)

wherein $R^{14}$ is H, OH, COOH, $NH_2$, a halogen, $R^{15}OH$, $R^{15}COOH$, $R^{15}C(O)$ $NH_2$, or $R^{15}C(O)$ $R^{16}$; $R^{15}$ is $C_{1-10}$ alkyl, $C_{2-10}$ alkenyl, or $C_{2-10}$ alkynyl; and $R^{16}$ is a halogen. In aspects of this embodiment, a bestatin moiety disclosed herein is of formula XIV, wherein $R^{14}$ is H, OH, COOH, $NH_2$, a halogen, $R^{15}OH$, $R^{15}COOH$, $R^{15}C(O)$ $NH_2$, or $R^{15}C(O)$ $R^{16}$; $R^{15}$ is $C_{1-6}$ alkyl, $C_{2-6}$ alkenyl, or $C_{2-6}$ alkynyl; and $R^{16}$ is a halogen. In other aspects of this embodiment, a bestatin moiety disclosed herein is of formula XIV, wherein $R^{14}$ is H, OH, COOH, $NH_2$, a halogen, $R^{15}OH$, $R^{15}COOH$, $R^{15}C(O)$ $NH_2$, or $R^{15}C(O)$ $R^{16}$; $R^{15}$ is $C_{1-4}$ alkyl, $C_{2-4}$ alkenyl, or $C_{2}$-4 alkynyl; and $R^{16}$ is a halogen. In yet other aspects of this embodiment, a bestatin moiety disclosed herein is of formula XIV, wherein $R^{14}$ is H, OH, COOH, $NH_2$, F, Br, Cl, I, $R^{15}OH$, $R^{15}COOH$, $R^{15}C(O)$ $NH_2$, or $R^{15}C(O)$ $R^{16}$; $R^{15}$ is $C_{1-6}$ alkyl, $C_{2-6}$ alkenyl, or $C_{2-6}$ alkynyl; and $R^{16}$ is a F, Br, Cl or I.

In another aspect of this embodiment, an E3 ligase-recruiting moiety is a phthalimide moiety. A phthalimide moiety is a competitive, reversible protease inhibitor. A phthalimide moiety is a molecule comprising a phthalimide, $C_6H_4(CO)_2NH$. A phthalimide moiety includes thalidomide, lenalidomide and pomalidomide. In an aspect of this embodiment, a phthalimide moiety is formula XV

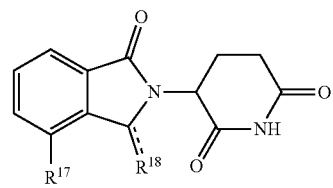

(XV)

wherein $R^{17}$ is H, OH, COOH, $NH_2$, a halogen, $R^{19}OH$, $R^{19}COOH$, $R^{19}C(O)$ $NH_2$, or $R^{19}C(O)$ $R^{20}$, $NHR^{19}OH$, $NHR^{19}COOH$, $NHR^{19}C(O)$ $NH_2$, or $NHR^{19}C(O)$ $R^{20}$; $R^{18}$ is H, OH, O, COOH, or $C_{1-6}$; $R^{19}$ is $C_{1-10}$ alkyl, $C_{2-10}$ alkenyl, or $C_{2-10}$ alkynyl; and $R^{20}$ is a halogen. In aspects of this embodiment, a phthalimide moiety disclosed herein is of formula XV, wherein $R^{17}$ is H, OH, COOH, $NH_2$, a halogen, $R^{19}OH$, $R^{19}COOH$, $R^{19}C(O)$ $NH_2$, or $R^{19}C(O)$ $R^{20}$, $NHR^{19}OH$, $NHR^{19}COOH$, $NHR^{19}C(O)$ $NH_2$, or $NHR^{19}C(O)$ $R^{20}$; $R^{18}$ is H, OH, O, COOH, or $C_{1-6}$; $R^{19}$ is $C_{1-6}$ alkyl, $C_{2-6}$ alkenyl, or $C_{2-6}$ alkynyl; and $R^{20}$ is a halogen. In other aspects of this embodiment, a phthalimide moiety disclosed herein is of formula XV, wherein $R^{17}$ is H, OH, COOH, $NH_2$, a halogen, $R^{19}OH$, $R^{19}COOH$, $R^{19}C(O)$ $NH_2$, or $R^{19}C(O)$ $R^{20}$, $NHR^{19}OH$, $NHR^{19}COOH$, $NHR^{19}C(O)$ $NH_2$, or $NHR^{19}C(O)$ $R^{20}$; $R^{18}$ is H, OH, O, COOH, or $C_{1-6}$; $R^{19}$ is $C_{1-4}$ alkyl, $C_{2-4}$ alkenyl, or $C_{2-4}$ alkynyl; and $R^{20}$ is a halogen. In yet other aspects of this embodiment, a phthalimide moiety disclosed herein is of formula XV, wherein $R^{17}$ is H, OH, COOH, $NH_2$, F, Br, Cl, I, $R^{19}OH$, $R^{19}COOH$, $R^{19}C(O)$ $NH_2$, or $R^{19}C(O)$ $R^{20}$, $NHR^{19}OH$, $NHR^{19}COOH$, $NHR^{19}C(O)$ $NH_2$, or $NHR^{19}C(O)$ $R^{20}$; $R^{18}$ is H, OH, O, COOH, or $C_{1-6}$; $R^{19}$ is $C_{1-6}$ alkyl, $C_{2-6}$ alkenyl, or $C_{2-6}$ alkynyl; and $R^{20}$ is a F, Br, Cl or I.

In another aspect of this embodiment, a phthalimide moiety is any one of formulas XVI, XVII, XVIII or XIX

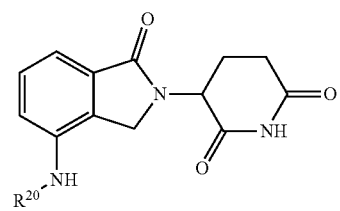

(XVI)

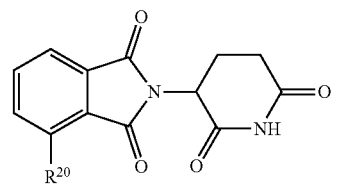

(XVII)

-continued (XVIII)

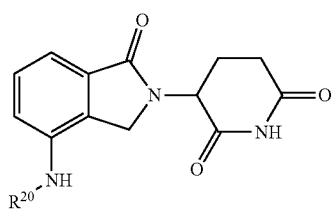

(XIX)

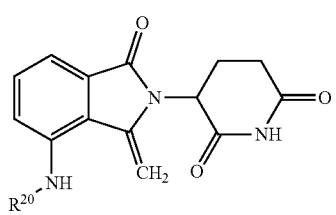

wherein $R^{20}$ is H, OH, COOH, $NH_2$, a halogen, $R^{21}OH$, $R^{21}COOH$, $R^{21}C(O)$ $NH_2$, or $R^{21}C(O)$ $R^{22}$; $R^{21}$ is $C_{1-10}$ alkyl, $C_{2-10}$ alkenyl, or $C_{2-10}$ alkynyl; and $R^{22}$ is a halogen. In aspects of this embodiment, a phthalimide moiety disclosed herein is any one of formulas XVI, XVII, XVIII or XIX, wherein $R^{20}$ is H, OH, COOH, $NH_2$, a halogen, $R^{21}OH$, $R^{21}COOH$, $R^{21}C(O)$ $NH_2$, or $R^{21}C(O)$ $R^{22}$; $R^{21}$ is $C_{1-6}$ alkyl, $C_{2-6}$ alkenyl, or $C_{2-6}$ alkynyl; and $R^{22}$ is a halogen. In other aspects of this embodiment, a phthalimide moiety disclosed herein is any one of formulas XVI, XVII, XVIII or XIX, wherein $R^{20}$ is H, OH, COOH, $NH_2$, a halogen, $R^{21}OH$, $R^{21}COOH$, $R^{21}C(O)$ $NH_2$, or $R^{21}C(O)$ $R^{22}$; and $R^{21}$ is $C_{1-4}$ alkyl, $C_{2-4}$ alkenyl, or $C_{2-4}$ alkynyl; and $R^{22}$ is a halogen. In yet other aspects of this embodiment, a phthalimide moiety disclosed herein is any one of formulas XVI, XVII, XVIII or XIX, wherein $R^{20}$ is H, OH, COOH, $NH_2$, F, Br, Cl, I, $R^{21}OH$, $R^{21}COOH$, $R^{21}C(O)$ $NH_2$, or $R^{21}C(O)$ $R^{22}$; and $R^{21}$ is $C_{1-6}$ alkyl, $C_{2-6}$ alkenyl, or $C_{2-6}$ alkynyl; and $R^{22}$ is a F, Br, Cl or I.

In an embodiment, an ARE disclosed herein is of formula XX:

(XX)

wherein n any integer from 0 to 10. In aspects of this embodiment, an ARE disclosed herein is of formula XX, wherein n any integer from 0 to 8. In yet other aspects of this embodiment, an ARE disclosed herein is of formula XX, wherein n any integer from 0 to 6. In still other aspects of this embodiment, an ARE disclosed herein is of formula XX, wherein n any integer from 0 to 4. In other aspects of this embodiment, an ARE disclosed herein is

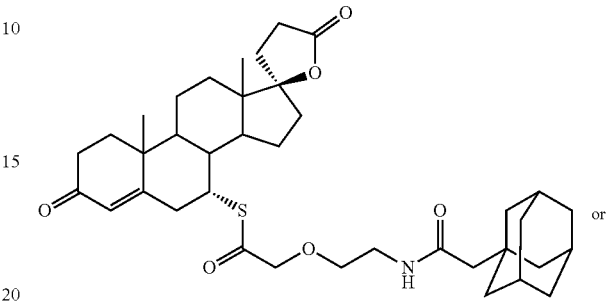

or

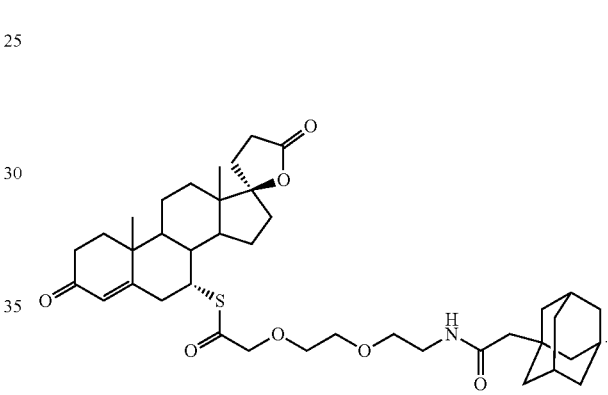

In an embodiment, an ARE disclosed herein is:

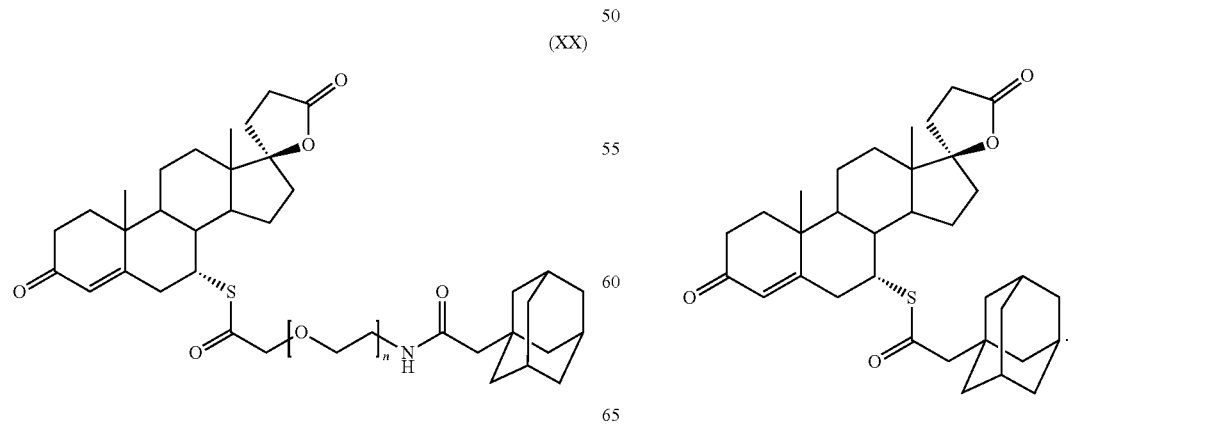

In an embodiment, an ARE disclosed herein is of formula XXI:

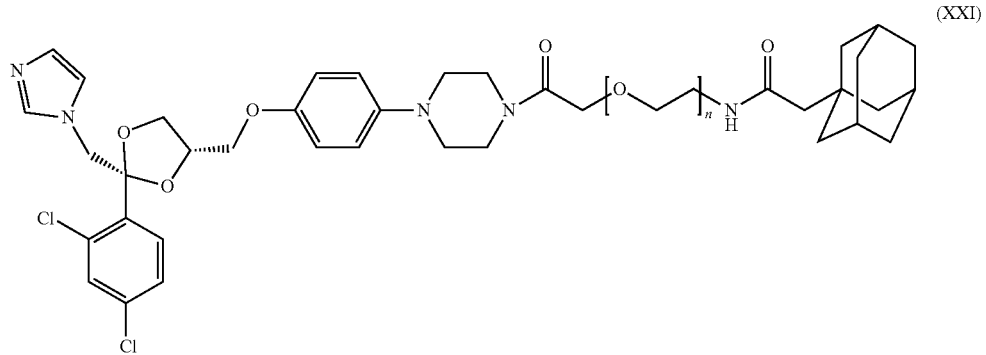

wherein n any integer from 0 to 10. In aspects of this embodiment, an ARE disclosed herein is of formula XXI, wherein n any integer from 0 to 8. In yet other aspects of this embodiment, an ARE disclosed herein is of formula XXI, wherein n any integer from 0 to 6. In still other aspects of this embodiment, an ARE disclosed herein is of formula XXI, wherein n any integer from 0 to 4. In other aspects of this embodiment, an ARE disclosed herein is

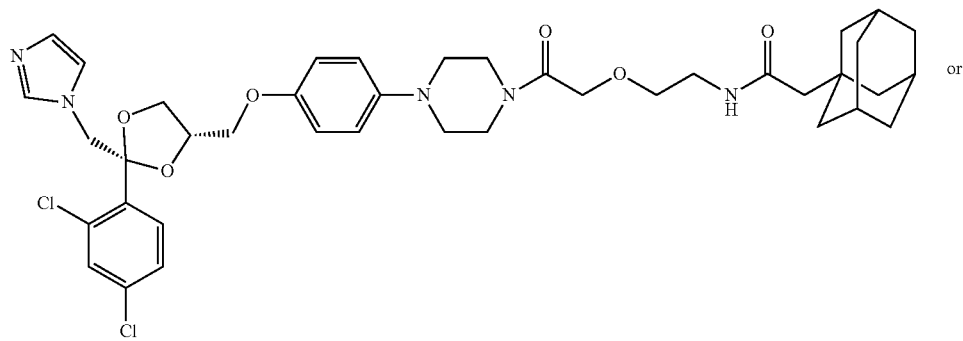 or

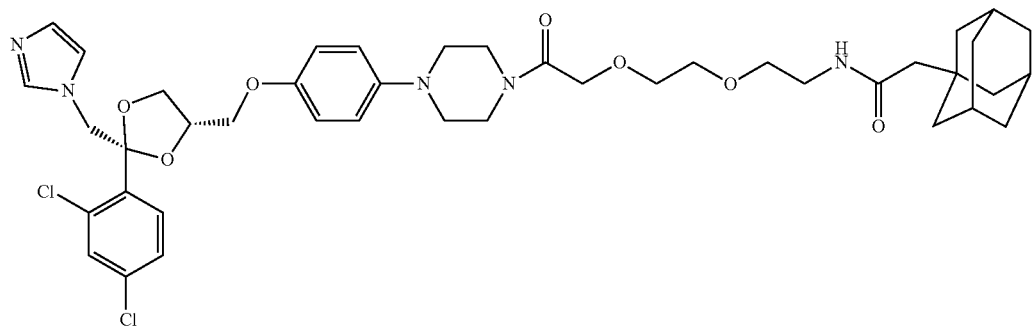

In an embodiment, an ARE disclosed herein is:

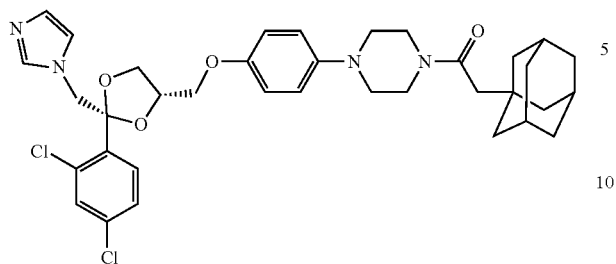

In an embodiment, an ARE disclosed herein is of formula XXII:

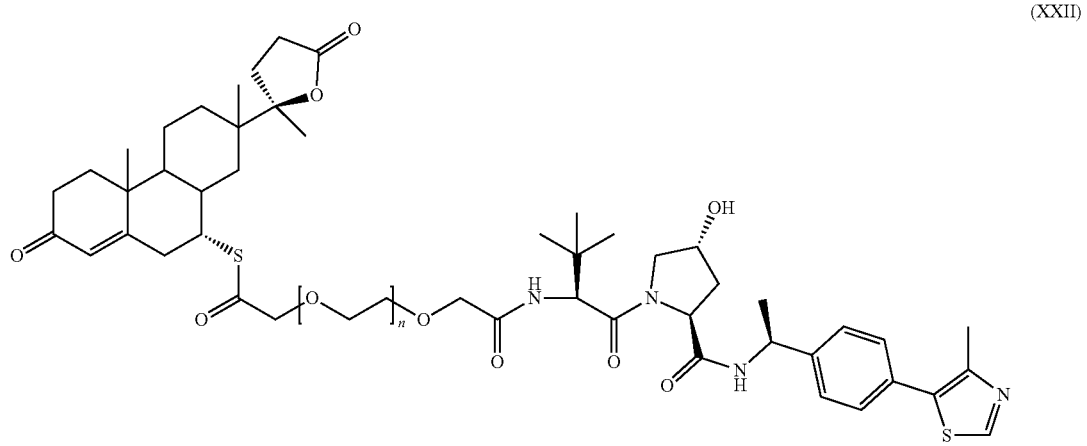

(XXII)

wherein n any integer from 0 to 10. In aspects of this embodiment, an ARE disclosed herein is of formula XXII, wherein n any integer from 0 to 8. In yet other aspects of this embodiment, an ARE disclosed herein is of formula XXII, wherein n any integer from 0 to 6. In still other aspects of this embodiment, an ARE disclosed herein is of formula XXII, wherein n any integer from 0 to 4. In other aspects of this embodiment, an ARE disclosed herein is

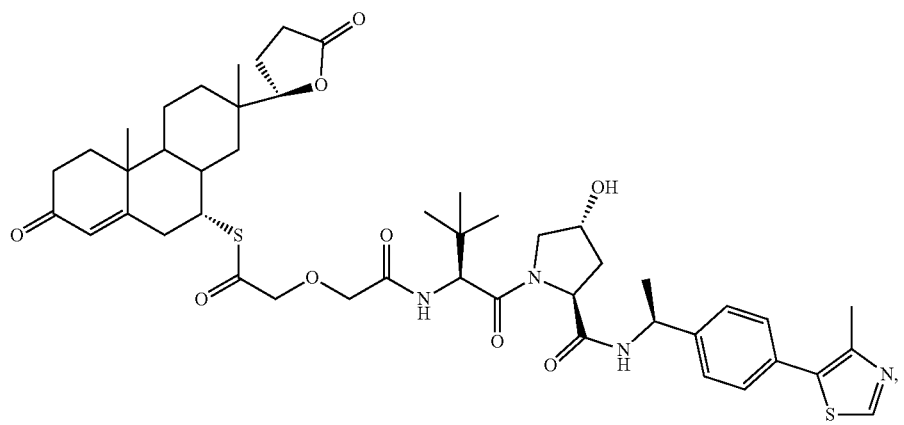

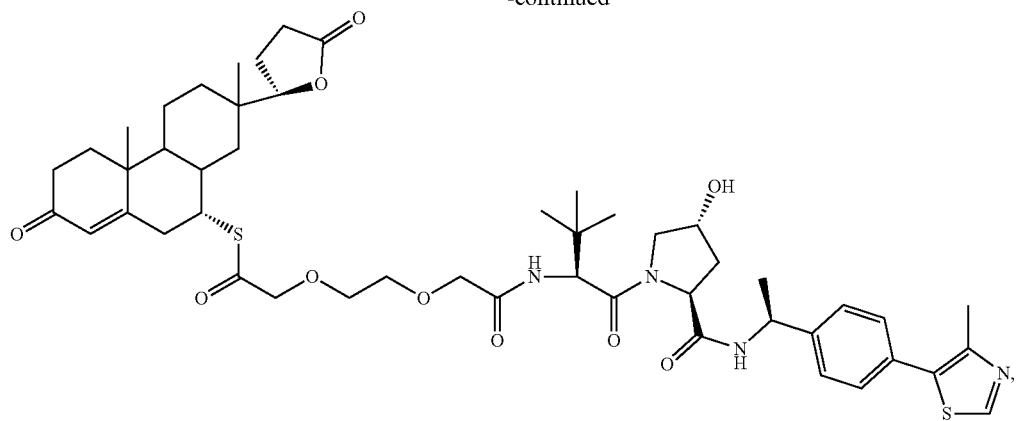
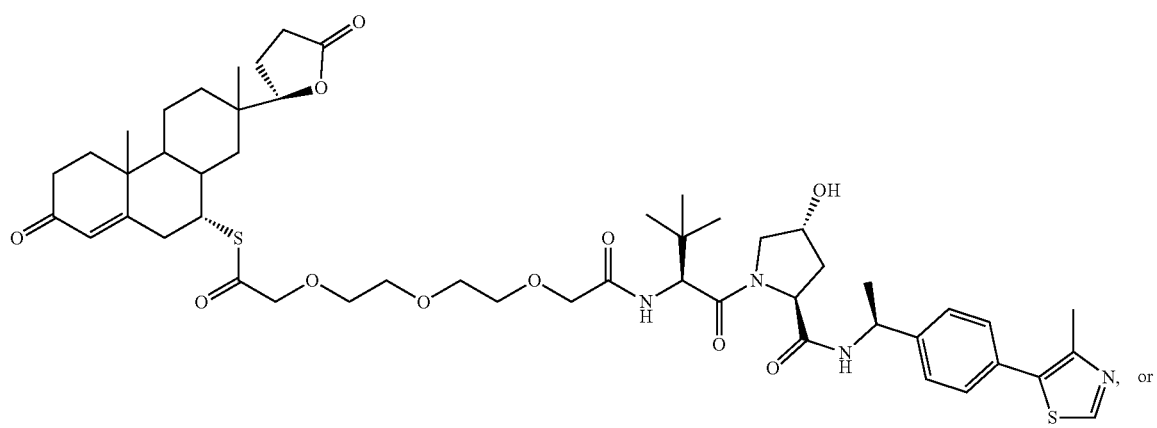
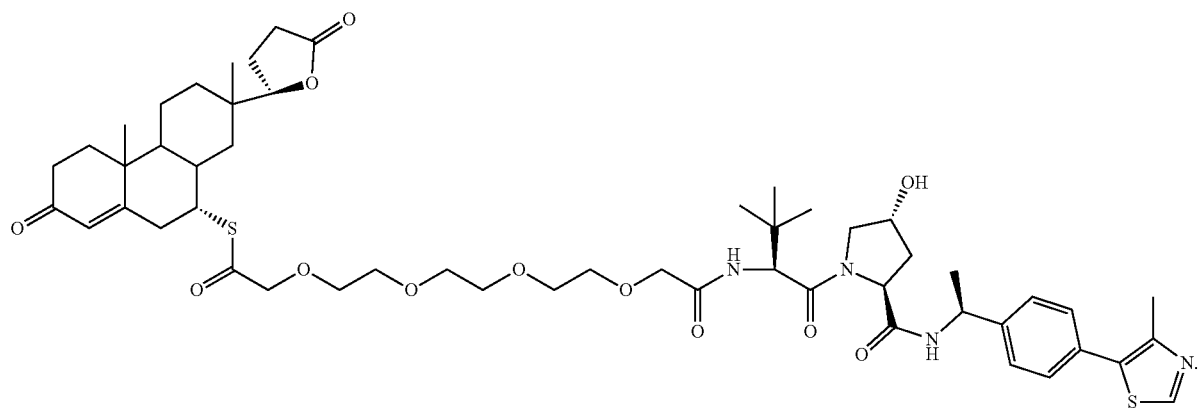

In an embodiment, an ARE disclosed herein is of formula XXIII:

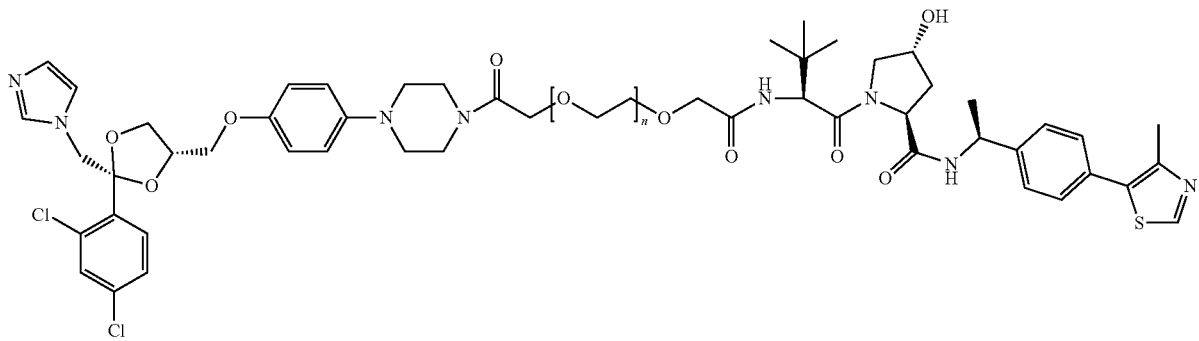

(XXIII)

wherein n any integer from 0 to 10. In aspects of this embodiment, an ARE disclosed herein is of formula XXIII, wherein n any integer from 0 to 8. In yet other aspects of this embodiment, an ARE disclosed herein is of formula XXIII, wherein n any integer from 0 to 6. In still other aspects of this embodiment, an ARE disclosed herein is of formula XXIII, wherein n any integer from 0 to 4. In other aspects of this embodiment, an ARE disclosed herein is

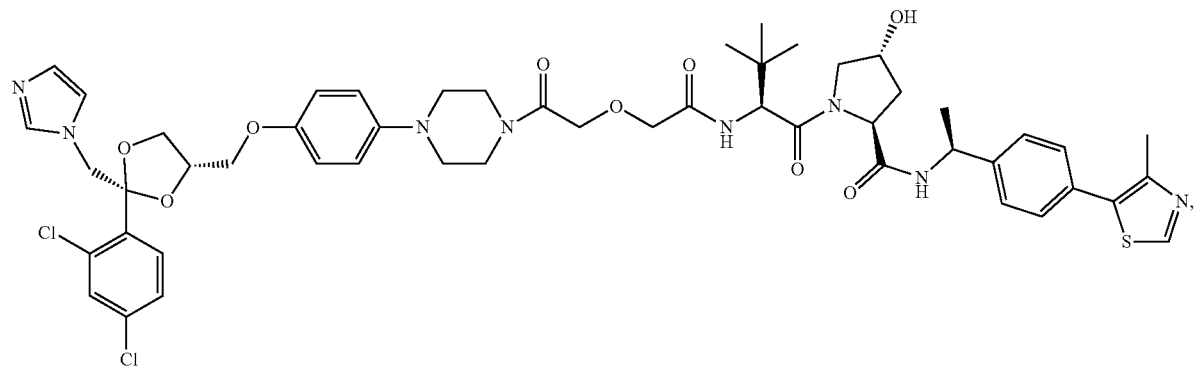

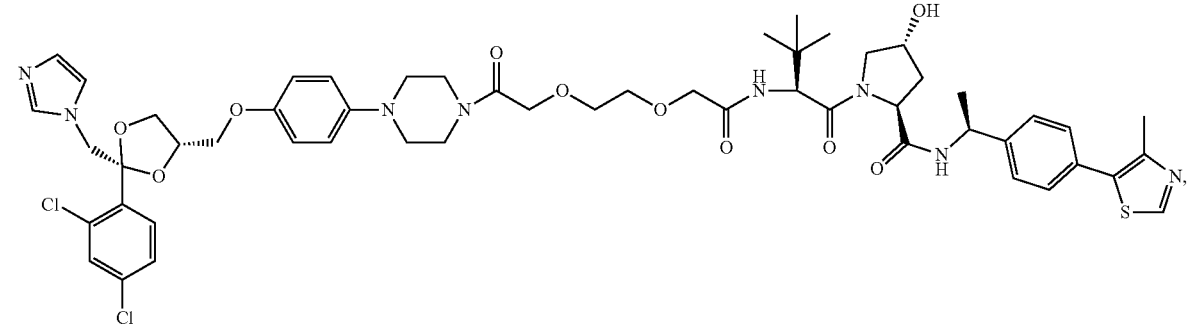

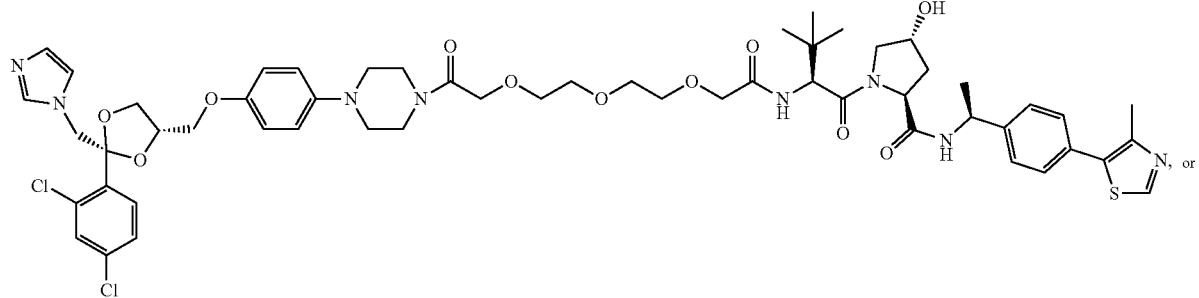

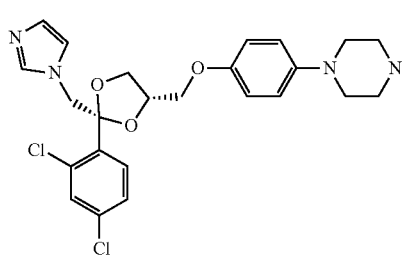
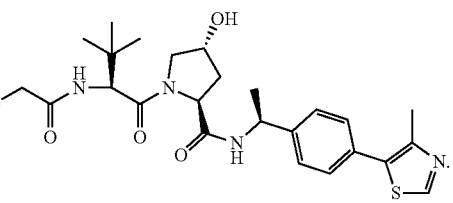

Aspects of the present specification disclose, in part, a pharmaceutical composition. A pharmaceutical composition refers to a therapeutically effective concentration of an active ingredient, such as, e.g., any of the AREs disclosed herein. Preferably, the pharmaceutical composition does not produce an adverse, allergic, or other untoward or unwanted reaction when administered to an individual. A pharmaceutical composition as disclosed herein is useful for medical and veterinary applications. A pharmaceutical composition may be administered to an individual alone, or in combination with other supplementary active compounds, agents, drugs or hormones.

In one embodiment, a composition can comprise a single ARE disclosed herein. In another embodiment, a composition can comprise a single ARE disclosed herein. In aspects of this embodiment, a composition disclosed herein comprises, e.g., one or more AREs, two or more AREs, three or more AREs, four or more AREs or five or more AREs. In other aspects of this embodiment, a composition disclosed herein comprises, e.g., only one ARE, at most two AREs, at most three AREs, at most four AREs, or at most five AREs. In yet other aspects of this embodiment, a composition disclosed herein comprises from, e.g., 1 to 2 AREs, 1 to 3 AREs, 1 to 4 AREs, 1 to 5 AREs, 2 to 3 AREs, 2 to 4 AREs, 2 to 5 AREs, 3 to 4 AREs, 3 to 5 AREs or 4 to 5 AREs.

The amount of one or more AREs in a pharmaceutical composition disclosed herein will generally range from about 0.01% to about 50% by weight of the total composition preferably from about 0.1% to about 50% by weight of total composition, more preferably from about 1% to about 50% by weight of the total composition.

In aspects of this embodiment, a composition disclosed herein comprises an ARE in an amount of, e.g., 0.01%, 0.025%, 0.05%, 0.075%, 0.1%, 0.2%, 0.25%, 0.3%, 0.4%, 0.5%, 0.6%, 0.7%, 0.75%, 0.8%, 0.9%, 1%, 2%, 3%, 4%, 5%, 6%, 7%, 8%. 9%, 10%, 15%, 20%, 25%, 30%, 35%, 40%, 45% or 50% by weight of the composition. In other aspects of this embodiment, a composition disclosed herein comprises an ARE in an amount of, e.g., at least 0.01%, at least 0.025%, at least 0.05%, at least 0.075%, at least 0.1%, at least 0.25%, at least 0.5%, at least 0.75%, at least 1%, at least 2%, at least 3%, at least 4%, at least 5%, at least 6%, at least 7%, at least 8%, at least 9%, least 10%, least 15%, least 20%, least 25%, least 30%, least 35%, least 40%, at least 45%, or at least 50% by weight of the composition. In yet other aspects of this embodiment, a composition disclosed herein comprises an ARE in an amount of, e.g., at most 0.01%, at most 0.025%, at most 0.05%, at most 0.075%, at most 0.1%, at most 0.25%, at most 0.5%, at most 0.75%, at most 1%, at most 2%, at most 3%, at most 4%, at most 5%, at most 6%, at most 7%, at most 8%, at most 9%, at most 10%, at most 15%, at most 20%, at most 25%, at most 30%, at most 35%, at most 40%, at most 45%, or at most 50% by weight of the composition.

In still other aspects of this embodiment, a composition disclosed herein comprises an ARE in an amount of from, e.g., 0.01% to about 0.05%, 0.01% to about 0.075%, 0.01% to about 0.1%, about 0.1% to about 0.5%, about 0.1% to about 0.75%, about 0.1% to about 1%, about 0.1% to about 2%, about 0.1% to about 3%, about 0.1% to about 4%, about 0.1% to about 5%, about 0.1% to about 6%, about 0.1% to about 7%, about 0.1% to about 8%, about 0.1% to about 9%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.25% to about 0.5%, about 0.25% to about 0.75%, about 0.25% to about 1%, about 0.25% to about 2%, about 0.25% to about 3%, about 0.25% to about 4%, about 0.25% to about 5%, about 0.25% to about 6%, about 0.25% to about 7%, about 0.25% to about 8%, about 0.25% to about 9%, about 0.25% to about 10%, about 0.25% to about 15%, about 0.25% to about 20%, about 0.25% to about 25%, about 0.25% to about 30%, about 0.25% to about 35%, about 0.25% to about 40%, about 0.5% to about 0.75%, about 0.5% to about 1%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 9%, about 0.5% to about 10%, about 0.5% to about 15%, about 0.5% to about 20%, about 0.5% to about 25%, about 0.5% to about 30%, about 0.5% to about 35%, about 0.5% to about 40%, about 0.75% to about 1%, about 0.75% to about 2%, about 0.75% to about 3%, about 0.75% to about 4%, about 0.75% to about 5%, about 0.75% to about 6%, about 0.75% to about 7%, about 0.75% to about 8%, about 0.75% to about 9%, about 0.75% to about 10%, about 0.75% to about 15%, about 0.75% to about 20%, about 0.75% to about 25%, about 0.75% to about 30%, about 0.75% to about 35%, about 0.75% to about 40%, about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 1% to about 15%, about 1% to about 20%, about 1% to about 25%, about 1% to about 30%, about 1% to about 35%, about 1% to about 40%, about 2% to about 3%, about 2% to about 4%, about 2% to about 5%, about 2% to about 6%, about 2% to about 7%, about 2% to about 8%, about 2% to about 9%, about 2% to about 10%, about 2% to about 15%, about 2% to about 20%, about 2% to about 25%, about 2% to about 30%, about 2% to about 35%, about 2% to about 40%, about 3% to about 4%, about 3% to about 5%, about 3% to about 6%, about 3% to about 7%, about 3% to about 8%, about 3% to about 9%, about 3% to about 10%, about 3% to about 15%, about 3% to about 20%, about 3% to about 25%, about 3% to about 30%, about 3% to about 35%, about 3% to about 40%, about 4% to about 5%, about 4% to about 6%, about 4% to about 7%, about 4% to about 8%, about 4% to about 9%, about 4% to about 10%, about 4% to about 15%, about 4% to about 20%, about 4% to about 25%, about 4% to about 30%, about 4% to about 35%, about 4% to about 40%, about 5% to about 6%, about 5% to about 7%, about 5% to about 8%, about 5% to about 9%, about 5% to about 10%, about 5% to about 15%, about 5% to about 20%, about 5% to about 25%, about 5% to about 30%, about 5% to about 35%, about 5% to about 40%, about 6% to about 7%, about 6% to about 8%, about 6% to about 9%, about 6% to about 10%, about 6% to about 15%, about 6% to about 20%, about 6% to about 25%, about 6% to about 30%, about 6% to about 35%, about 6% to about 40%, about 7% to about 8%, about 7% to about 9%, about 7% to about 10%, about 7% to about 15%, about 7% to about 20%, about 7% to about 25%, about 7% to about 30%, about 7% to about 35%, about 7% to about 40%, about 8% to about 9%, about 8% to about 10%, about 8% to about 15%, about 8% to about 20%, about 8% to about 25%, about 8% to about 30%, about 8% to about 35%, about 8% to about 40%, about 9% to about 10%, about 9% to about 15%, about 9% to about 20%, about 9% to about 25%, about 9% to about 30%, about 9% to about 35%, about 9% to about 40%, about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45%, about 30% to about 25%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, or about 45% to about 50%, by weight of the composition.

In aspects of this embodiment, a composition disclosed herein comprises an ARE in an amount of, e.g., about 1 µg, about 2 µg, about 3 µg, about 4 µg, about 5 µg, about 6 µg, about 7 µg, about 8 µg, about 9 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, 260 µg, about 270 µg, about 280 µg, about 290 µg, about 300 µg, about 310 µg, about 320 µg, about 330 µg, about 340 µg, about 350 µg, 360 µg, about 370 µg, about 380 µg, about 390 µg, about 400 µg, about 410 µg, about 420 µg, about 430 µg, about 440 µg, about 450 µg, 460 µg, about 470 µg, about 480 µg, about 490 µg, about 500 µg, about 510 µg, about 520 µg, about 530 µg, about 540 µg, about 550 µg, 560 µg, about 570 µg, about 580 µg, about 590 µg, about 600 µg, about 610 µg, about 620 µg, about 630 µg, about 640 µg, about 650 µg, 660 µg, about 670 µg, about 680 µg, about 690 µg, about 700 µg, about 710 µg, about 720 µg, about 730 µg, about 740 µg, about 750 µg, 760 µg, about 770 µg, about 780 µg, at least 790 µg, about 800 µg, about 810 µg, about 820 µg, about 830 µg, about 840 µg, about 850 µg, 860 µg, about 870 µg, about 880 µg, about 890 µg, about 900 µg, about 910 µg, about 920 µg, about 930 µg, about 940 µg, about 950 µg, 960 µg, about 970 µg, about 980 µg, about 990 µg, or about 1,000 µg.

In other aspects of this embodiment, a composition disclosed herein comprises an ARE in an amount of, e.g., at least 1 µg, at least 2 µg, at least 3 µg, at least 4 µg, at least 5 µg, at least 6 µg, at least 7 µg, at least 8 µg, at least 9 µg, at least 10 µg, at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 110 µg, at least 120 µg, at least 130 µg, at least 140 µg, at least 150 µg, at least 160 µg, at least 170 µg, at least 180 µg, at least 190 µg, at least 200 µg, at least 210 µg, at least 220 µg, at least 230 µg, at least 240 µg, at least 250 µg, 260 µg, at least 270 µg, at least 280 µg, at least 290 µg, at least 300 µg, at least 310 µg, at least 320 µg, at least 330 µg, at least 340 µg, at least 350 µg, 360 µg, at least 370 µg, at least 380 µg, at least 390 µg, at least 400 µg, at least 410 µg, at least 420 µg, at least 430 µg, at least 440 µg, at least 450 µg, 460 µg, at least 470 µg, at least 480 µg, at least 490 µg, at least 500 µg, at least 510 µg, at least 520 µg, at least 530 µg, at least 540 µg, at least 550 µg, 560 µg, at least 570 µg, at least 580 µg, at least 590 µg, at least 600 µg, at least 610 µg, at least 620 µg, at least 630 µg, at least 640 µg, at least 650 µg, 660 µg, at least 670 µg, at least 680 µg, at least 690 µg, at least 700 µg, at least 710 µg, at least 720 µg, at least 730 µg, at least 740 µg, at least 750 µg, 760 µg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg.

In yet other aspects of this embodiment a composition disclosed herein comprises an ARE in an amount of, e.g., at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

In still other aspects of this embodiment, a composition disclosed herein comprises an ARE in an amount of, e.g., about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, or about 75 µg to about 250 µg.

In still other aspects of this embodiment, a composition disclosed herein comprises an ARE in an amount of, e.g., about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125 µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, or about 200 µg to about 1,000 µg.

In still other aspects of this embodiment, a composition disclosed herein comprises an ARE in an amount of, e.g., about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, or about 400 µg to about 1,000 µg.

In still other aspects of this embodiment, a composition disclosed herein comprises an ARE in an amount of, e.g., about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, or about 800 µg to about 1,000 µg.

In aspects of this embodiment, a composition disclosed herein comprises an ARE in an amount of, e.g., about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, 260 mg, about 270 mg, about 280 mg, about 290 mg, about 300 mg, about 310 mg, about 320 mg, about 330 mg, about 340 mg, about 350 mg, 360 mg, about 370 mg, about 380 mg, about 390 mg, about 400 mg, about 410 mg, about 420 mg, about 430 mg, about 440 mg, about 450 mg, 460 mg, about 470 mg, about 480 mg, about 490 mg, about 500 mg, about 510 mg, about 520 mg, about 530 mg, about 540 mg, about 550 mg, 560 mg, about 570 mg, about 580 mg, about 590 mg, about 600 mg, about 610 mg, about 620 mg, about 630 mg, about 640 mg, about 650 mg, 660 mg, about 670 mg, about 680 mg, about 690 mg, about 700 mg, about 710 mg, about 720 mg, about 730 mg, about 740 mg, about 750 mg, 760 mg, about 770 mg, about 780 mg, about 790 mg, about 800 mg, about 810 mg, about 820 mg, about 830 mg, about 840 mg, about 850 mg, 860 mg, about 870 mg, about 880 mg, about 890 mg, about 900 mg, about 910 mg, about 920 mg, about 930 mg, about 940 mg, about 950 mg, 960 mg, about 970 mg, about 980 mg, about 990 mg, or about 1,000 mg.

In other aspects of this embodiment, a composition disclosed herein comprises an ARE in an amount of, e.g., at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, 260 mg, at least 270 mg, at least 280 mg, at least 290 mg, at least 300 mg, at least 310 mg, at least 320 mg, at least 330 mg, at least 340 mg, at least 350 mg, 360 mg, at least 370 mg, at least 380 mg, at least 390 mg, at least 400 mg, at least 410 mg, at least 420 mg, at least 430 mg, at least 440 mg, at least 450 mg, 460 mg, at least 470 mg, at least 480 mg, at least 490 mg, at least 500 mg, at least 510 mg, at least 520 mg, at least 530 mg, at least 540 mg, at least 550 mg, 560 mg, at least 570 mg, at least 580 mg, at least 590 mg, at least 600 mg, at least 610 mg, at least 620 mg, at least 630 mg, at least 640 mg, at least 650 mg, 660 mg, at least 670 mg, at least 680 mg, at least 690 mg, at least 700 mg, at least 710 mg, at least 720 mg, at least 730 mg, at least 740 mg, at least 750 mg, 760 mg, at least 770 mg, at least 780 mg, at least 790 mg, at least 800 mg, at least 810 mg, at least 820 mg, at least 830 mg, at least 840 mg, at least 850 mg, 860 mg, at least 870 mg, at least 880 mg, at least 890 mg, at least 900 mg, at least 910 mg, at least 920 mg, at least 930 mg, at least 940 mg, at least 950 mg, 960 mg, at least 970 mg, at least 980 mg, at least 990 mg, or at least 1,000 mg.

In yet other aspects of this embodiment, a composition disclosed herein comprises an ARE in an amount of, e.g., at most 1 mg, at most 2 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, at most 70 mg, at most 75 mg, at most 80 mg, at most 85 mg, at most 90 mg, at most 95 mg, at most 100 mg, at most 110 mg, at most 120 mg, at most 130 mg, at most 140 mg, at most 150 mg, at most 160 mg, at most 170 mg, at most 180 mg, at most 190 mg, at most 200 mg, at most 210 mg, at most 220 mg, at most 230 mg, at most 240 mg, at most 250 mg, 260 mg, at most 270 mg, at most 280 mg, at most 290 mg, at most 300 mg, at most 310 mg, at most 320 mg, at most 330 mg, at most 340 mg, at most 350 mg, 360 mg, at most 370 mg, at most 380 mg, at most 390 mg, at most 400 mg, at most 410 mg, at most 420 mg, at most 430 mg, at most 440 mg, at most 450 mg, 460 mg, at most 470 mg, at most 480 mg, at most 490 mg, at most 500 mg, at most 510 mg, at most 520 mg, at most 530 mg, at most 540 mg, at most 550 mg, 560 mg, at most 570 mg, at most 580 mg, at most 590 mg, at most 600 mg, at most 610 mg, at most 620 mg, at most 630 mg, at most 640 mg, at most 650 mg, 660 mg, at most 670 mg, at most 680 mg, at most 690 mg, at most 700 mg, at most 710 mg, at most 720 mg, at most 730 mg, at most 740 mg, at most 750 mg, 760 mg, at most 770 mg, at most 780 mg, at most 790 mg, at most 800 mg, at most 810 mg, at most 820 mg, at most 830 mg, at most 840 mg, at most 850 mg, 860 mg, at most 870 mg, at most 880 mg, at most 890 mg, at most 900 mg, at most 910 mg, at most 920 mg, at most 930 mg, at most 940 mg, at most 950 mg, 960 mg, at most 970 mg, at most 980 mg, at most 990 mg, or at most 1,000 mg.

In still other aspects of this embodiment, a composition disclosed herein comprises an ARE in an amount of, e.g., about 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, about 1 mg to about 90 mg, about 1 mg to about 100 mg, about 1 mg to about 110 mg, about 1 mg to about 120 mg, about 1 mg to about 130 mg, about 1 mg to about 140 mg, about 1 mg to about 150 mg, about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, about 5 mg to about 90 mg, about 5 mg to about 100 mg, about 5 mg to about 110 mg, about 5 mg to about 120 mg, about 5 mg to about 130 mg, about 5 mg to about 140 mg, about 5 mg to about 150 mg, about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 110 mg, about 10 mg to about 120 mg, about 10 mg to about 130 mg, about 10 mg to about 140 mg, about 10 mg to about 150 mg, about 10 mg to about 175 mg, about 10 mg to about 200 mg, about 10 mg to about 225 mg, about 10 mg to about 250 mg, about 25 mg to about 50 mg, about 25 mg to about 75 mg, about 25 mg to about 100 mg, about 25 mg to about 125 mg, about 25 mg to about 150 mg, about 25 mg to about 175 mg, about 25 mg to about 200 mg, about 25 mg to about 225 mg, about 25 mg to about 250 mg, about 50 mg to about 75 mg, about 50 mg to about 100 mg, about 50 mg to about 125 mg, about 50 mg to about 150 mg, about 50 mg to about 175 mg, about 50 mg to about 200 mg, about 50 mg to about 225 mg, about 50 mg to about 250 mg, about 75 mg to about 100 mg, about 75 mg to about 125 mg, about 75 mg to about 150 mg, about 75 mg to about 175 mg, about 75 mg to about 200 mg, about 75 mg to about 225 mg, or about 75 mg to about 250 mg.

In still other aspects of this embodiment, a composition disclosed herein comprises an ARE in an amount of, e.g., about 100 mg to about 125 mg, about 100 mg to about 150 mg, about 100 mg to about 175 mg, about 100 mg to about 200 mg, about 100 mg to about 225 mg, about 100 mg to about 250 mg, about 100 mg to about 275 mg, about 100 mg to about 300 mg, about 100 mg to about 325 mg, about 100 mg to about 350 mg, about 100 mg to about 375 mg, about 100 mg to about 400 mg, about 100 mg to about 425 mg, about 100 mg to about 450 mg, about 100 mg to about 475 mg, about 100 mg to about 500 mg, about 100 mg to about 525 mg, about 100 mg to about 550 mg, about 100 mg to about 575 mg, about 100 mg to about 600 mg, about 125 mg to about 150 mg, about 125 mg to about 175 mg, about 125 mg to about 200 mg, about 125 mg to about 225 mg, about 125 mg to about 250 mg, about 125 mg to about 275 mg, about 125 mg to about 300 mg, about 125 mg to about 325 mg, about 125 mg to about 350 mg, about 125 mg to about 375 mg, about 125 mg to about 400 mg, about 125 mg to about 425 mg, about 125 mg to about 450 mg, about 125 mg to about 475 mg, about 125 mg to about 500 mg, about 125 mg to about 525 mg, about 125 mg to about 550 mg, about 125 mg to about 575 mg, about 125 mg to about 600 mg, about 150 mg to about 175 mg, about 150 mg to about 200 mg, about 150 mg to about 225 mg, about 150 mg to about 250 mg, about 150 mg to about 275 mg, about 150 mg to about 300 mg, about 150 mg to about 325 mg, about 150 mg to about 350 mg, about 150 mg to about 375 mg, about 150 mg to about 400 mg, about 150 mg to about 425 mg, about 150 mg to about 450 mg, about 150 mg to about 475 mg, about 150 mg to about 500 mg, about 150 mg to about 525 mg, about 150 mg to about 550 mg, about 150 mg to about 575 mg, about 150 mg to about 600 mg, about 200 mg to about 225 mg, about 200 mg to about 250 mg, about 200 mg to about 275 mg, about 200 mg to about 300 mg, about 200 mg to about 325 mg, about 200 mg to about 350 mg, about 200 mg to about 375 mg, about 200 mg to about 400 mg, about 200 mg to about 425 mg, about 200 mg to about 450 mg, about 200 mg to about 475 mg, about 200 mg to about 500 mg, about 200 mg to about 525 mg, about 200 mg to about 550 mg, about 200 mg to about 575 mg, about 200 mg to about 600 mg, about 200 mg to about 625 mg, about 200 mg to about 650 mg, about 200 mg to about 675 mg, about 200 mg to about 700 mg, about 200 mg to about 725 mg, about 200 mg to about 750 mg, about 200 mg to about 775 mg, about 200 mg to about 800 mg, about 200 mg to about 825 mg, about 200 mg to about 850 mg, about 200 mg to about 875 mg, about 200 mg to about 900 mg, about 200 mg to about 925 mg, about 200 mg to about 950 mg, about 200 mg to about 975 mg, or about 200 mg to about 1,000 mg.

In still other aspects of this embodiment, a composition disclosed herein comprises an ARE in an amount of, e.g., about 250 mg to about 275 mg, about 250 mg to about 300 mg, about 250 mg to about 325 mg, about 250 mg to about 350 mg, about 250 mg to about 375 mg, about 250 mg to about 400 mg, about 250 mg to about 425 mg, about 250 mg to about 450 mg, about 250 mg to about 475 mg, about 250 mg to about 500 mg, about 250 mg to about 525 mg, about 250 mg to about 550 mg, about 250 mg to about 575 mg, about 250 mg to about 600 mg, about 250 mg to about 625 mg, about 250 mg to about 650 mg, about 250 mg to about 675 mg, about 250 mg to about 700 mg, about 250 mg to about 725 mg, about 250 mg to about 750 mg, about 250 mg to about 775 mg, about 250 mg to about 800 mg, about 250 mg to about 825 mg, about 250 mg to about 850 mg, about 250 mg to about 875 mg, about 250 mg to about 900 mg, about 250 mg to about 925 mg, about 250 mg to about 950 mg, about 250 mg to about 975 mg, about 250 mg to about 1,000 mg, about 300 mg to about 325 mg, about 300 mg to about 350 mg, about 300 mg to about 375 mg, about 300 mg to about 400 mg, about 300 mg to about 425 mg, about 300 mg to about 450 mg, about 300 mg to about 475 mg, about 300 mg to about 500 mg, about 300 mg to about 525 mg, about 300 mg to about 550 mg, about 300 mg to about 575 mg, about 300 mg to about 600 mg, about 300 mg to about 625 mg, about 300 mg to about 650 mg, about 300 mg to about 675 mg, about 300 mg to about 700 mg, about 300 mg to about 725 mg, about 300 mg to about 750 mg, about 300 mg to about 775 mg, about 300 mg to about 800 mg, about 300 mg to about 825 mg, about 300 mg to about 850 mg, about 300 mg to about 875 mg, about 300 mg to about 900 mg, about 300 mg to about 925 mg, about 300 mg to about 950 mg, about 300 mg to about 975 mg, about 300 mg to about 1,000 mg, about 400 mg to about 425 mg, about 400 mg to about 450 mg, about 400 mg to about 475 mg, about 400 mg to about 500 mg, about 400 mg to about 525 mg, about 400 mg to about 550 mg, about 400 mg to about 575 mg, about 400 mg to about 600 mg, about 400 mg to about 625 mg, about 400 mg to about 650 mg, about 400 mg to about 675 mg, about 400 mg to about 700 mg, about 400 mg to about 725 mg, about 400 mg to about 750 mg, about 400 mg to about 775 mg, about 400 mg to about 800 mg, about 400 mg to about 825 mg, about 400 mg to about 850 mg, about 400 mg to about 875 mg, about 400 mg to about 900 mg, about 400 mg to about 925 mg, about 400 mg to about 950 mg, about 400 mg to about 975 mg, or about 400 mg to about 1,000 mg.

In still other aspects of this embodiment, a composition disclosed herein comprises an ARE in an amount of, e.g., about 500 mg to about 525 mg, about 500 mg to about 550 mg, about 500 mg to about 575 mg, about 500 mg to about 600 mg, about 500 mg to about 625 mg, about 500 mg to about 650 mg, about 500 mg to about 675 mg, about 500 mg to about 700 mg, about 500 mg to about 725 mg, about 500 mg to about 750 mg, about 500 mg to about 775 mg, about 500 mg to about 800 mg, about 500 mg to about 825 mg, about 500 mg to about 850 mg, about 500 mg to about 875 mg, about 500 mg to about 900 mg, about 500 mg to about 925 mg, about 500 mg to about 950 mg, about 500 mg to about 975 mg, about 500 mg to about 1,000 mg, about 600 mg to about 625 mg, about 600 mg to about 650 mg, about 600 mg to about 675 mg, about 600 mg to about 700 mg, about 600 mg to about 725 mg, about 600 mg to about 750 mg, about 600 mg to about 775 mg, about 600 mg to about 800 mg, about 600 mg to about 825 mg, about 600 mg to about 850 mg, about 600 mg to about 875 mg, about 600 mg to about 900 mg, about 600 mg to about 925 mg, about 600 mg to about 950 mg, about 600 mg to about 975 mg, about 600 mg to about 1,000 mg, about 700 mg to about 725 mg, about 700 mg to about 750 mg, about 700 mg to about 775 mg, about 700 mg to about 800 mg, about 700 mg to about 825 mg, about 700 mg to about 850 mg, about 700 mg to about 875 mg, about 700 mg to about 900 mg, about 700 mg to about 925 mg, about 700 mg to about 950 mg, about 700 mg to about 975 mg, about 700 mg to about 1,000 mg, about 800 mg to about 825 mg, about 800 mg to about 850 mg, about 800 mg to about 875 mg, about 800 mg to about 900 mg, about 800 mg to about 925 mg, about 800 mg to about 950 mg, about 800 mg to about 975 mg, or about 800 mg to about 1,000 mg.

A pharmaceutical composition disclosed herein can optionally include a pharmaceutically acceptable carrier that facilitates processing of an ARE into pharmaceutically acceptable compositions. A pharmacologically acceptable carrier is synonymous with "pharmacological carrier" and refers to any carrier that has substantially no long term or permanent detrimental effect when administered and encompasses terms such as pharmacologically acceptable vehicle, stabilizer, diluent, additive, auxiliary, or excipient. Such a carrier generally is mixed with an active compound or permitted to dilute or enclose the active compound and can be a solid, semi-solid, or liquid agent. It is understood that the active ingredients can be soluble or can be delivered as a suspension in the desired carrier or diluent.

In one embodiment, a single pharmaceutically acceptable carrier is present in a composition disclosed herein. In another embodiment, a plurality of pharmaceutically acceptable carriers are present in a composition disclosed herein. In aspects of this embodiment, a composition disclosed herein comprises, e.g., one or more, two or more, three or more, four or more or five or more pharmaceutically acceptable carriers. In other aspects of this embodiment, a composition disclosed herein comprises, e.g., only one, at most two, at most three, at most four, or at most five pharmaceutically acceptable carriers. In yet other aspects of this embodiment, a composition disclosed herein comprises from, e.g., 1 to 2, 1 to 3, 1 to 4, 1 to 5, 2 to 3, 2 to 4, 2 to 5, 3 to 4, 3 to 5 or 4 to 5 pharmaceutically acceptable carriers.

In another embodiment, a composition disclosed herein comprises an amount of pharmaceutically acceptable carrier that provides a desired formulative or beneficial effect to a pharmaceutical composition disclosed herein. In aspects of this embodiment, a composition disclosed herein comprises a pharmaceutically acceptable carrier in an amount of, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% by weight of the composition. In other aspects of this embodiment, a composition disclosed herein comprises a pharmaceutically acceptable carrier in an amount of, e.g., at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98% or at most 99% by weight of the composition. In yet other aspects of this embodiment, a composition disclosed herein comprises a pharmaceutically acceptable carrier in an amount of from, e.g., about 25% to about 50%, about 25% to about 75%, about 25% to about 90%, about 25% to about 95%, about 25% to about 96%, about 25% to about 97%, about 25% to about 98%, about 25% to about 99%, about 50% to about 75%, about 50% to about 90%, about 50% to about 95%, about 50% to about 96%, about 50% to about 97%, about 50% to about 98%, about 50% to about 99%, about 75% to about 80%, about 75% to about 85%, about 75% to about 90%, about 75% to about 95%, about 75% to about 96%, about 75% to about 97%, about 75% to about 98%, about 75% to about 99%, about 80% to about 85%, about 80% to about 90%, about 80% to about 95%, about 80% to about 96%, about 80% to about 97%, about 80% to about 98%, about 80% to about 99%, about 85% to about 90%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, about 90% to about 99%, or about 95% to about 99%, by weight of the composition.

A pharmaceutical composition disclosed herein may further comprise one or more pharmaceutically acceptable components (or pharmaceutical components), including, without limitation, buffers, preservatives, tonicity adjusters, salts, antioxidants, osmolality adjusting agents, physiological substances, pharmacological substances, bulking agents, viscosity agents, surfactants, emulsifying agents, wetting agents, sweetening or flavoring agents, and the like. Various buffers and means for adjusting pH can be used to prepare a pharmaceutical composition disclosed herein, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, chlorhexidine, thimerosal, a parahydroxybenzoic acid such as, e.g., like methyl-, propyl-, or butyl-parahydroxybenzoic acid, a phenylmercuric salt such as, e.g., nitrate, chloride, acetate, and borate, a stabilized oxy chloro composition, such as, e.g., PURITE® and chelants, such as, e.g., EDTA, DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. A bulking agent or viscosity agent useful in a pharmaceutical composition include, without limitation, a polysaccharide, such as, e.g., methylcellulose, mucopolysaccharides, e.g., hyaluronic acid and chondroitin sulfate, or polyalcohol, e.g., polyvinylalcohol. Various slow releasing gels and matrices may also be employed as well as soluble and insoluble ocular inserts, for instance, based on substances forming in-situ gels. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition.

A pharmaceutical composition disclosed herein can be formulated into any form that enables topical application of an ARE disclosed herein in a manner that achieves a desired beneficial effect. A topical application refers to the use of at least ARE described herein, incorporated in a suitable pharmaceutical carrier, and applied at a site of skin and/or thinning hair or baldness for exertion of local action. Accordingly, such topical compositions include those pharmaceutical forms in which the at least one ARE is applied externally by direct contact with the skin surface to be treated.

In one embodiment, a composition disclosed herein can be formulated into, e.g., a single phase formulation or a biphasic formulation comprising a medium phase and a dispersed phase. In another embodiment, a composition disclosed herein can be formulated into, e.g., a liquid composition, a colloidal composition, a semi-solid composition, or a solid composition. In another embodiment, a composition disclosed herein can be formulated into, e.g., a liquid aerosol, a foam, an emulsion, a gel, a sol, or a solid sol. In another embodiment, a composition disclosed herein can be formulated into, e.g., a spray, a liquid aerosol, a wash, an aftershave, a perfume, a lotion, a cream, a salve, a waxing composition, a mousse, a shampoo, a conditioner, an ointment, a liniment, a paste, a jelly, a soap, a suspension, or an emollient. Various gels and matrices for slow release delivery may also be employed as well as soluble and insoluble ocular inserts, for instance, based on substances forming in-situ gels.

In one embodiment, a pharmaceutical composition disclosed herein is mixed with a dermatologically compatible vehicle or carrier. The vehicle which may be employed for preparing compositions may comprise, for example, aqueous solutions such as e.g., physiological salines, oil solutions or ointments. The vehicle furthermore may contain dermatologically compatible preservatives such as e.g., benzalkonium chloride, surfactants like e.g., polysorbate 80, liposomes or polymers, for example, methyl cellulose, polyvinyl alcohol, polyvinyl pyrrolidone and hyaluronic acid; these may be used for increasing the viscosity. Furthermore, it is also possible to use soluble or insoluble drug inserts when the drug is to be administered.

In one embodiment, a pharmaceutical composition disclosed herein comprising 0.1% to 10% of a compound disclosed herein, 20% to 40% denatured alcohol, 40% to 60% isopropyl myristate, and 10% to 30% Transcutol. In aspects of this embodiment, a pharmaceutical composition disclosed herein comprising 0.25% to 8% of a compound disclosed herein, 23% to 37% denatured alcohol, 43% to 57% isopropyl myristate, and 13% to 27% Transcutol. In other aspects of this embodiment, a pharmaceutical composition disclosed herein comprising 0.5% to 5% of a compound disclosed herein, 25% to 35% denatured alcohol, 45% to 55% isopropyl myristate, and 15% to 25% Transcutol. In yet other aspects of this embodiment, a pharmaceutical composition disclosed herein comprising 0.75% to 3% of a compound disclosed herein, 27% to 32% denatured alcohol, 47% to 52% isopropyl myristate, and 17% to 22% Transcutol. In still other aspects of this embodiment, a pharmaceutical composition disclosed herein comprising 1% to 2% of a compound disclosed herein, 29% to 31% denatured alcohol, 48% to 50% isopropyl myristate, and 19% to 21% Transcutol.

In one embodiment, a pharmaceutical composition disclosed herein comprising 0.1% to 10% of any one of Compounds 37 to 52, or any combination thereof, 20% to 40% denatured alcohol, 40% to 60% isopropyl myristate, and 10% to 30% Transcutol. In aspects of this embodiment, a pharmaceutical composition disclosed herein comprising 0.25% to 8% of any one of Compounds 37 to 52, or any combination thereof, 23% to 37% denatured alcohol, 43% to 57% isopropyl myristate, and 13% to 27% Transcutol. In other aspects of this embodiment, a pharmaceutical composition disclosed herein comprising 0.5% to 5% of any one of Compounds 37 to 52, or any combination thereof, 25% to 35% denatured alcohol, 45% to 55% isopropyl myristate, and 15% to 25% Transcutol. In yet other aspects of this embodiment, a pharmaceutical composition disclosed herein comprising 0.75% to 3% of any one of Compounds 37 to 52, or any combination thereof, 27% to 32% denatured alcohol, 47% to 52% isopropyl myristate, and 17% to 22% Transcutol. In still other aspects of this embodiment, a pharmaceutical composition disclosed herein comprising 1% to 2% of any one of Compounds 37 to 52, or any combination thereof, 29% to 31% denatured alcohol, 48% to 50% isopropyl myristate, and 19% to 21% Transcutol.

In one embodiment, a pharmaceutical composition disclosed herein can be housed in containers suitable for dispensing the composition. The container can be a vial, bottle, tube, etc. In certain embodiments, the container will be a squeezable in order to release the composition therein. The container can have a lid, which may snap, twist, etc. on and off. The container should be such that the sterility of the composition therein is maintained. In certain embodiments, the container will have a safety seal prior to opening. In one embodiment, a container may hold from about 1 mL to about 50 mL of the composition disclosed herein. In aspects of this embodiment, a container may hold from, e.g., 1 mL to 5 mL, 1 mL to 10 mL, 1 mL to 15 mL, 1 mL to 20 mL, 1 mL to 25 mL, 1 mL to 30 mL, 1 mL to 35 mL, 1 mL to 40 mL, 1 mL to 45 mL, 1 mL to 50 mL, 2 mL to 5 mL, 2 mL to 10 mL, 2 mL to 15 mL, 2 mL to 20 mL, 2 mL to 25 mL, 2 mL to 30 mL, 2 mL to 35 mL, 2 mL to 40 mL, 2 mL to 45 mL, 2 mL to 50 mL, 3 mL to 5 mL, 3 mL to 10 mL, 3 mL to 15 mL, 3 mL to 20 mL, 3 mL to 25 mL, 3 mL to 30 mL, 3 mL to 35 mL, 3 mL to 40 mL, 3 mL to 45 mL, 3 mL to 50 mL, 5 mL to 10 mL, 5 mL to 15 mL, 5 mL to 20 mL, 5 mL to 25 mL, 5 mL to 30 mL, 5 mL to 35 mL, 5 mL to 40 mL, 5 mL to 45 mL, 5 mL to 50 mL, 10 mL to 20 ml, 10 mL to 30 mL, 10 mL to 40 mL, 10 mL to 50 mL, 20 mL to 30 mL, 20 mL to 40 mL, 20 mL to 50 mL, 30 mL to 40 mL, 30 mL to 50 mL, or 40 mL to 50 mL.

A pharmaceutical composition disclosed herein can be provided in a kit. A kit can comprise a delivery system having one or more of an applicator brush, porous foam swab or pad, hollow tube, dipstick, or a combination thereof. In certain embodiments, the delivery system comprises a plurality of applicator brushes that have filaments coated with a lubricity enhancing agent. The lubricity enhancing agent can be a polymer that is coated onto the filaments in order to control the release of the composition from the brush, that is, the composition is not released from the brush until it makes contact with the skin surface and the rate of release is such that a therapeutically appropriate amount of a composition is released from the brush onto a skin surface. The applicator brushes of the kit are useful for applying the hair growth enhancing composition to the site of interest, that is, at least one skin region. There may be a plurality of applicator brushes in a kit. For example, in a 30 day supply kit, there can be 60 applicators, such that there is one applicator for each eye, per application, for 30 days. Alternately, there can be 2, 10, 20, 30, 40, 50, 60, 90, 120, etc. applicators per kit. Within the kit, the applicator brushes may be packaged individually, or in sets of 2 or more. The applicator brushes are packaged such that they remain sterile until use. In certain embodiments, the applicator brushes can be packaged in plastic sheaths. Further, to prevent contamination of the eye, they are preferably single-use, disposable applicators.

The kit can also comprise a set of instructions. The instructions may include information useful to the end user such as how to use the delivery system and hair growth enhancing composition, how often to use it, etc.

The contents of the kit, the applicator brushes, container of composition, and instructions, are enclosed in an outer casing. The outer casing can be a box, a sealed bag, a foil pouch, etc. In certain embodiments, the delivery system, container and instructions are enclosed in a box. In other embodiments of the kit, the container and instructions are contained in a first box, the delivery system is contained in a second box, and the first and second box are contained together in a third box.

Aspects of the present specification disclose, in part, a method for treating hair loss. Such method involves administering an effective amount of one or more AREs or pharmaceutical composition disclosed herein to at least one hair region or a portion thereof associated with hair loss, wherein the administration results in a reduction in the attribute associated with hair loss. The term "hair loss" is synonymous with "alopecia" and refers to the absence or loss of hair from a skin surface, including, without limitation, hair loss from the scalp, face, beard, head, pubic area, upper lip, eyebrows, and/or eyelids.

Aspects of the present specification disclose, in part, a method for treating hair thinning. Such method involves administering an effective amount of one or more AREs or pharmaceutical composition disclosed herein to at least one hair region or a portion thereof associated with hair thinning, wherein the administration results in a reduction in the attribute associated with hair thinning. The term "hair thinning" refers to an age-related condition where hair follicles produce hairs that are shorter in length, smaller in diameter, lighter in color, and more fragile as opposed to no hair production at all. Hair thinning is a condition where the shaft of each hair becomes shorter in length, smaller in diameter (finer), less pigmented, and/or more fragile. As such, hair thinning is distinct from hair loss, a condition in which the hair follicle stops producing a hair shaft altogether. As discussed above, the hair follicle is a complex mini organ. But like all biological systems, the biologically active part of the hair follicle undergoes an aging process. This aging process is characterized by 1) the migration of the base of the hair follicle upwards toward the skin surface, a decline in the synthesis of hair keratins, and a loss of pigmentation. Although producing hairs, older hair follicles make hairs that are shorter in length, smaller in diameter, lighter in color, and more fragile. Taken together, this age-related shift in hair characteristics manifests itself as hair thinning. Thinning hair affects an estimated 40 million men and 25 million women in the United States. The emotional impact from hair loss can lead to anxiety, stress, depression, and lower self-esteem.

Aspects of the present specification disclose, in part, a method for treating hair color loss. Such method involves administering an effective amount of one or more AREs or pharmaceutical composition disclosed herein to at least one hair region or a portion thereof associated with hair color loss, wherein the administration results in a reduction in the attribute associated with hair color loss. The term "hair color loss" refers to the reduction of pigmentation of the hair shaft.

Hair includes that of mammalian species, including both humans and animals. In humans, hair includes hair of the scalp, face, beard, head, pubic area, upper lip, eyebrows, and eyelids. In animals, hair includes hair of the entire surface of the body. For example, for animals raised for their pelts, such as, e.g., a mink, a chinchilla, fox, or a beaver, the compounds can be applied over the entire surface of the body to improve the overall fur for commercial reasons. The process can also be used for cosmetic reasons in animals, e.g., applied to the skin of dogs and cats having bald patches due to mange or other diseases causing a degree of hair appearance.

Aspects of the present specification disclose, in part, a method for treating a condition associated with a degenerative hair follicle disorder. Such method involves administering an effective amount of one or more AREs or pharmaceutical composition disclosed herein to at least one hair region or a portion thereof associated with a degenerative hair follicle disorder, wherein the administration results in a reduction in the attribute associated with the degenerative hair follicle disorder. A degenerative hair follicle disorder is a condition where the function or structure of a hair follicle progressively deteriorates over time. A degenerative hair follicle disorder results in hair loss, hair thinning, and/or hair color loss. For example, a degenerative hair follicle disorder include alopecia including scarring alopecias and non-scarring alopecias.

In an aspect of this embodiment, a composition disclosed herein is administered to an individual to treat a degenerative hair follicle disorder associated with hair loss, hair thinning, hair color loss, no new hair shaft growth, reduced rate of hair shaft growth, reduced hair shaft diameter (thickness), reduced hair shaft length, reduced hair density, reduced keratinization of the hair shaft, increased fragility, reduced hair pigmentation, reduced hair shaft luster, reduced hair health, reduced time a hair follicle spends in anagen phase, reduced time a hair follicle spends in catagen phase, reduced time a hair follicle spends in telogen phase, premature release of hair shaft from hair follicle, premature initiation of apoptosis in hair follicle, premature conversion of a terminal hair into a vellus hair.

Alopecia can be caused by a multitude of factors including, without limitation, genetic make-up, functional disorder, hereditary disorder, hereditary disposition of the hair shaft or genodermatoses, chemical breakage such as over processing, or frequent use of chemical relaxer, heat damage as from repeated hot comb use, chronic exposure to traction on hair shaft, compulsive hair pulling, telogen effluvium resulting from physical or psychological stress, secondary syphilis can cause "moth eaten hair loss", discoid lupus erythematosus or chronic cutanous lupus erythematosus, lichenplanopilaris, pseudopelade of Brocq, tufted folliculitis, dissecting cellulitis, alopecia mucinosa, keratosis follicularis spinulosa decalvans, adverse effect from certain drugs such as chemotherapy, radiation therapy, and testosterone booster tablets. Alopecia frequently occurs in patients undergoing treatment for cancer or suffering from other diseases, such as AIDS, where cell-killing, or cytotoxic, drugs are used.

Alopecia is typically categorized as scarring or nonscarring. Scarring alopecia, also known as "alopecia cicatrisata" or "cicatricial alopecia," refers to hair loss characterized by potentially permanent and irreversible destruction of hair follicles and their replacement with scar tissue. Non-limiting examples of scarring alopecia include bullous diseases, chemical alopecia, discoid lupus erythematosus, severre folliculitis, lichen planopilaris, dissecting cellulitis, central centrifugal cicatricial alopecia, postmenopausal frontal fibrosing alopecia, and tumors and skin outgrowths, such as, e.g., sebaceous nevus, basal cell carcinoma, and squamous cell carcinoma.

Nonscarring alopecia refers to hair loss without permanent destruction of the hair follicle. Non-limiting examples of nonscarring alopecia include anagen effluvium, alopecia adnata, alopecia androgenetica, alopecian AREata, alopecia congenitalis, alopecia *diffusa*, alopecia disseminate, alopecia follicularis, alopecia leprotica, alopecia *marginalis*, alopecia medicamentosa, alopecia mucinosa, alopecia neurotica, alopecia pityrodes, alopecia presenili, alopecia *senilis*, alopecia symptomatica, alopecia syphilitica, alopecia totalis, alopecia toxica, alopecia *triangularis*, alopecia *triangularis* congenitalis, alopecia universalis, folliculitis, olliculitis decalvans, traction alopecia, trichotillomania, telogen effluvium, and inherited disorders of the hair shaft.

In an embodiment, a pharmaceutical composition disclosed herein is administered to an individual to treat a degenerative hair follicle disorder associated with scarring alopecia. In aspects of this embodiment, a composition disclosed herein is administered to an individual to treat a degenerative hair follicle disorder associated with a bullous disease, a chemical exposure, a discoid lupus erythematosus, a severre folliculitis, a lichen planopilaris, a dissecting cellulitis, a central centrifugal cicatricial alopecia, a postmenopausal frontal fibrosing alopecia, a tumor, or a skin outgrowth.

In another embodiment, a pharmaceutical composition disclosed herein is administered to an individual to treat a non-scarring alopecia. In aspects of this embodiment, a composition disclosed herein is administered to an individual to treat a degenerative hair follicle disorder associated anagen effluvium, alopecia adnata, alopecia androgenetica, alopecian AREata, alopecia congenitalis, alopecia *diffusa*, alopecia disseminate, alopecia a follicularis, alopecia leprotica, alopecia *marginalis*, alopecia medicamentosa, alopecia mucinosa, alopecia neurotica, alopecia pityrodes, alopecia presenili, alopecia *senilis*, alopecia symptomatica, alopecia syphilitica, alopecia totalis, alopecia toxica, alopecia *triangularis*, alopecia *triangularis* congenitalis, alopecia universalis, folliculitis, olliculitis decalvans, traction alopecia, trichotillomania, telogen effluvium, or inherited disorder of the hair shaft.

In another aspect of this embodiment, a degenerative hair follicle disorder associated with hair loss in an individual is treated by reducing an attribute associated with hair loss. In aspects of this embodiment, reduction of the attribute associated with hair loss is accomplished by increasing the rate of hair growth, increasing hair thickness, increasing hair length, increasing hair density, increasing number of hairs produce per follicle, increasing hair pigmentation, increasing hair luster, converting intermediate or vellus hair to terminal hair, increasing hair health, increasing the time a hair follicle remains in anagen phase, increasing the time a hair follicle remains in catagen phase, increasing the time a hair follicle remains in telogen phase, prolonging or preventing the release of the hair shaft from the hair follicle, or prolonging or preventing the initiation of apoptosis in a hair follicle.

In aspects of this embodiment, reduction of the attribute associated with a degenerative hair follicle disorder associated with hair thinning is accomplished by increasing the rate of hair growth, increasing hair thickness, increasing hair length, increasing hair density, increasing number of hairs produce per follicle, increasing keratin production in the hair shaft, increasing hair shaft pigmentation, increasing hair shaft luster, converting intermediate or vellus hair to terminal hair, increasing hair health, increasing the time a hair follicle remains in anagen phase, increasing the time a hair follicle remains in catagen phase, or increasing the time a hair follicle remains in telogen phase.

In an embodiment, a pharmaceutical composition disclosed herein is administered to an individual to treat a degenerative hair follicle disorder associated with hair color loss. In another aspect of this embodiment, a composition disclosed herein is administered to an individual to treat a degenerative hair follicle disorder associated with decreases pigmentation of the hair shaft, decreased melanin production, increased death of melanocytes associated with apoptosis or any other cause.

In aspects of this embodiment, reduction of the attribute associated with a degenerative hair follicle disorder associated with hair color loss is accomplished by increasing pigmentation of the hair shaft, increasing melanin production, increasing hair luster, converting intermediate or vellus hair to terminal hair, increasing hair health, increasing the time a hair follicle remains in anagen phase, increasing the time a hair follicle remains in catagen phase, increasing the time a hair follicle remains in telogen phase, prolonging or preventing melanocyte death, or prolonging or preventing the initiation of apoptosis in a hair follicle.

Aspects of the present specification disclose, in part, a method of improving hair appearance. Such methods involve administering an effective amount of one or more AREs or pharmaceutical composition disclosed herein to at least one hair region or a portion thereof, wherein administration improves an attribute of hair appearance. This administration results in an improvement of at least one hair attribute including, without limitation, increased hair length, increased hair thickness, increased new hair growth, increased hair growth rate, increased hair number, increased conversion of intermediate hair into terminal hair, increased hair density, increased number of hairs per follicle, and/or increased hair color or darkness.

Aspects of the present specification disclose, in part, a method for treating a skin condition, disease or disorder. Such method involves administering an effective amount of an ARE or pharmaceutical composition disclosed herein to at least one skin region or a portion thereof associated with a skin condition, disease or disorder. As used herein, the term "skin region" is synonymous with "epidermal region." In aspects of this embodiment, a skin condition, disease or disorder includes, without limitation, an acne, an excessive sebum production, a post-wound scar formation, or a dermatological issue associated with polycystic ovary disease.

An effective amount (or therapeutically effective amount) of the at least one ARE disclosed herein is one that reduces or inhibits one or more physiological conditions, attributes or symptoms of a skin or hair condition, disorder or disease associated with AR-mediated signaling. An effective amount may be determined by one of ordinary skill in the art but will vary depending on the ARE employed, frequency of the application, and desired result.

In aspects of this embodiment, a therapeutically effective amount of the at least one ARE disclosed herein reduces or inhibits one or more physiological conditions, attributes or symptoms of a skin or hair condition, disorder or disease associated with AR-mediated signaling by, e.g., at least 10%, at least 20%, at least 30%, at least 40%, at least 50%, at least 60%, at least 70%, at least 80%, at least 90% or at least 95%.

In yet other aspects of this embodiment, a therapeutically effective amount of the at least one compound enhances an attribute associated with hair by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 70%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%. In aspects of this embodiment, a therapeutically effective dose is the dosage sufficient to achieve the desired therapeutic effect for, e.g., at least one day, at least two days, at least three days, at least four days, at least five days, at least six days, at least seven days, at least one week, at least two weeks, at least three weeks, at least four weeks, at least one month, at least two months, at least three months, at least four months, at least five months, at least six months, at least seven months, at least eight months, at least nine months, at least ten months, at least eleven months, or at least twelve months.

In aspects of this embodiment, an effective amount of an ARE disclosed herein generally is in the range of about 0.001 mg/kg/day to about 100 mg/kg/day. In aspects of this embodiment, an effective amount of an ARE disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In other aspects of this embodiment, an effective amount of an ARE disclosed herein may be, e.g., at most 0.001 mg/kg/day, at most 0.01 mg/kg/day, at most 0.1 mg/kg/day, at most 1.0 mg/kg/day, at most 5.0 mg/kg/day, at most 10 mg/kg/day, at most 15 mg/kg/day, at most 20 mg/kg/day, at most 25 mg/kg/day, at most 30 mg/kg/day, at most 35 mg/kg/day, at most 40 mg/kg/day, at most 45 mg/kg/day, or at most 50 mg/kg/day.

In other aspects of this embodiment, an effective amount of an ARE disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of an ARE disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of an ARE disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of an ARE disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of an ARE disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In other aspects of this embodiment, an effective amount of an ARE disclosed herein generally is in the range of about 0.001 mg/day to about 100 mg/day. In aspects of this embodiment, an effective amount of an ARE disclosed herein may be, e.g., at least 0.001 mg/day, at least 0.01 mg/day, at least 0.1 mg/day, at least 1.0 mg/day, at least 5.0 mg/day, at least 10 mg/day, at least 15 mg/day, at least 20 mg/day, at least 25 mg/day, at least 30 mg/day, at least 35 mg/day, at least 40 mg/day, at least 45 mg/day, or at least 50 mg/day. In other aspects of this embodiment, an effective amount of an ARE disclosed herein may be, e.g., at most 0.001 mg/day, at most 0.01 mg/day, at most 0.1 mg/day, at most 1.0 mg/day, at most 5.0 mg/day, at most 10 mg/day, at most 15 mg/day, at most 20 mg/day, at most 25 mg/day, at most 30 mg/day, at most 35 mg/day, at most 40 mg/day, at most 45 mg/day, or at most 50 mg/day.

In other aspects of this embodiment, an effective amount of an ARE disclosed herein may be in the range of, e.g., about 0.001 mg/day to about 10 mg/day, about 0.001 mg/day to about 15 mg/day, about 0.001 mg/day to about 20 mg/day, about 0.001 mg/day to about 25 mg/day, about 0.001 mg/day to about 30 mg/day, about 0.001 mg/day to about 35 mg/day, about 0.001 mg/day to about 40 mg/day, about 0.001 mg/day to about 45 mg/day, about 0.001 mg/day to about 50 mg/day, about 0.001 mg/day to about 75 mg/day, or about 0.001 mg/day to about 100 mg/day. In yet other aspects of this embodiment, an effective amount of an ARE disclosed herein may be in the range of, e.g., about 0.01 mg/day to about 10 mg/day, about 0.01 mg/day to about 15 mg/day, about 0.01 mg/day to about 20 mg/day, about 0.01 mg/day to about 25 mg/day, about 0.01 mg/day to about 30 mg/day, about 0.01 mg/day to about 35 mg/day, about 0.01 mg/day to about 40 mg/day, about 0.01 mg/day to about 45 mg/day, about 0.01 mg/day to about 50 mg/day, about 0.01 mg/day to about 75 mg/day, or about 0.01 mg/day to about 100 mg/day. In still other aspects of this embodiment, an effective amount of an ARE disclosed herein may be in the range of, e.g., about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 35 mg/day, about 0.1 mg/day to about 40 mg/day, about 0.1 mg/day to about 45 mg/day, about 0.1 mg/day to about 50 mg/day, about 0.1 mg/day to about 75 mg/day, or about 0.1 mg/day to about 100 mg/day.

In other aspects of this embodiment, an effective amount of an ARE disclosed herein may be in the range of, e.g., about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 35 mg/day, about 1 mg/day to about 40 mg/day, about 1 mg/day to about 45 mg/day, about 1 mg/day to about 50 mg/day, about 1 mg/day to about 75 mg/day, or about 1 mg/day to about 100 mg/day. In yet other aspects of this embodiment, an effective amount of an ARE disclosed herein may be in the range of, e.g., about 5 mg/day to about 10 mg/day, about 5 mg/day to about 15 mg/day, about 5 mg/day to about 20 mg/day, about 5 mg/day to about 25 mg/day, about 5 mg/day to about 30 mg/day, about 5 mg/day to about 35 mg/day, about 5 mg/day to about 40 mg/day, about 5 mg/day to about 45 mg/day, about 5 mg/day to about 50 mg/day, about 5 mg/day to about 75 mg/day, or about 5 mg/day to about 100 mg/day.

Dosing can be single dosage or cumulative (serial dosing), and can be readily determined by one skilled in the art. For instance, method of treatment disclosed herein may comprise a one-time administration of an effective amount of an ARE or pharmaceutical composition disclosed herein. As a non-limiting example, an effective amount of an ARE or pharmaceutical composition disclosed herein can be administered once to an individual, e.g., as a single injection or deposition. Alternatively, a method of treatment disclosed herein may comprise multiple administrations of an effective amount of an ARE or pharmaceutical composition disclosed herein carried out over a range of time periods, such as, e.g., daily, every other day, every third of day, once a week, multiple times per week, once a month, multiple times per month, once a year or multiple times per year. A pharmaceutical composition disclosed herein can be administered multiple times per day, e.g., twice a day, three times a day, four time a day, five times a day, or six times a day. The timing of administration can vary from individual to individual, depending upon such factors as the severity of an individual's symptoms. For example, an effective amount of an ARE or pharmaceutical composition disclosed herein can be administered to an individual 1 to 5 times every day for an indefinite period of time, or until the individual no longer requires therapy, e.g., for a period of treatment of at least one week, more preferably at least one month, more preferably at least three months, and most preferably at least six months. A person of ordinary skill in the art will recognize that the condition of the individual can be monitored throughout the course of treatment and that the effective amount of a pharmaceutical composition disclosed herein that is administered can be adjusted accordingly.

In aspects of this embodiment, hair length from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, hair length increases relative to an untreated region by, e.g., about 5% to about 100%, about 15% to about 100%, about 25% to about 100%, about 35% to about 100%, or about 45% to about 100%. In still other aspects of this embodiment, hair length from a treated region increases relative to an untreated region by, e.g., about 1 mm to about 500 mm, about 10 mm to about 500 mm, or about 100 mm to about 500 mm. Is further aspects of this embodiment, hair length from a treated region increases relative to an untreated region by, e.g., at least 1 mm, at least, 2 mm, at least, 3 mm, at least 4 mm, at least 5 mm, at least 6 mm, at least 7 mm, at least 8 mm, at least 9 mm, or at least 10 mm.

In other aspects of this embodiment, hair thickness from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, hair thickness from a treated region increases relative to an untreated region by, e.g., about 5% to about 100%, about 15% to about 100%, about 25% to about 100%, about 35% to about 100%, or about 45% to about 100%. In still other aspects of this embodiment, hair thickness from a treated region increases relative to an untreated region by, e.g., about 1 $\mu m^2$ to about 1 $\mu m^2$, about 10 $\mu m^2$ to about 1 $mm^2$, about 100 $\mu m^2$ to about 1 $mm^2$, or about 100 $\mu m^2$ to about 2 $mm^2$. Is further aspects of this embodiment, hair thickness from a treated region increases relative to an untreated by, e.g., at least 100 $\mu m^2$, at least 200 $\mu m^2$, at least 300 $\mu m^2$, at least 400 $\mu m^2$, at least 500 $\mu m^2$, at least 600 $\mu m^2$, at least 700 $\mu m^2$, at least 800 $\mu m^2$, at least 900 $\mu m^2$, at least 1 $mm^2$, at least 2 $mm^2$, or at least 3 $mm^2$.

In aspects of this embodiment, new hair growth from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In other aspects of this embodiment, new hair growth from a treated region increases relative to an untreated region by, e.g., about 5% to about 100%, about 15% to about 100%, about 25% to about 100%, about 35% to about 100%, or about 45% to about 100%.

In other aspects of this embodiment, the rate of hair growth from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, the rate of hair growth from a treated region increases relative to an untreated region by, e.g., about 5% to about 100%, about 15% to about 100%, about 25% to about 100%, about 35% to about 100%, or about 45% to about 100%.

In other aspects of this embodiment, the hair numbers from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, hair numbers from a treated region increases relative to an untreated region by, e.g., about 5% to about 100%, about 15% to about 100%, about 25% to about 100%, about 35% to about 100%, or about 45% to about 100%.

In other aspects of this embodiment, the conversion of intermediate hairs into terminal hairs from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, the conversion of intermediate hairs into terminal hairs from a treated region increases relative to an untreated region by, e.g., about 5% to about 100%, about 15% to about 100%, about 25% to about 100%, about 35% to about 100%, or about 45% to about 100%.

In other aspects of this embodiment, hair density from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, hair density from a treated region increases relative to an untreated region by, e.g., about 5% to about 100%, about 15% to about 100%, about 25% to about 100%, about 35% to about 100%, or about 45% to about 100%.

In other aspects of this embodiment, the number of hairs produce per hair follicle from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In yet other aspects of this embodiment, the number of hairs produce per hair follicle from a treated region increases relative to an untreated region by, e.g., about 5% to about 100%, about 15% to about 100%, about 25% to about 100%, about 35% to about 100%, or about 45% to about 100%. In still other aspects of this embodiment, the number of hairs produce per hair follicle from a treated region increases relative to an untreated region by, e.g., 2 or more hair shafts/follicle, 3 or more hair shafts/follicle, 4 or more hair shafts/follicle, or 5 or more hair shafts/follicle. In further aspects of this embodiment, the number of hairs produced per hair follicle from a treated region increases relative to an untreated region by, e.g., 2 hair shafts/follicle, 3 hair shafts/follicle, 4 hair shafts/follicle, or 5 hair shafts/follicle. In yet further aspects of this embodiment, the number of hairs produce per hair follicle from a treated region increases relative to an untreated region by, e.g., 2 to 5 hair shafts/follicle, 3 to 5 hair shafts/follicle, 2 to 4 hair shafts/follicle, or 2 to 3 hair shafts/follicle.

In other aspects of this embodiment, hair color from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In other aspects of this embodiment, hair color from a treated region increases relative to an untreated region by, e.g., about 5% to about 100%, about 15% to about 100%, about 25% to about 100%, about 35% to about 100%, or about 45% to about 100%.

In other aspects of this embodiment, hair pigmentation and/or melanization from a treated region increases relative to an untreated region by, e.g., at least 5%, at least 10%, at least 15%, at least 20%, at least 25%, at least 30%, at least 40%, at least 50%, at least 60%, at least 70%, at least 80%, at least 90%, or at least 95%. In other aspects of this embodiment, hair pigmentation and/or melanization from a treated region increases relative to an untreated region by, e.g., about 5% to about 100%, about 15% to about 100%, about 25% to about 100%, about 35% to about 100%, or about 45% to about 100%.

A pharmaceutical composition disclosed herein can be applied according to a method disclosed herein to a site of skin and/or thinning hair or baldness. Application of a compositions disclosed herein can be by rubbing, pouring, sprinkling, or spraying on, or otherwise applied to a site of skin and/or thinning hair or baldness. A pharmaceutical composition disclosed herein can be applied by introducing or impregnating a composition into or onto a solid support such as, e.g., a dressing, a wipe, a towelette, a towel, a mitt, a glove, or a mask and then applying the composition to a site of skin and/or thinning hair or baldness. A pharmaceutical composition disclosed herein can be applied by using a delivery device, such as, e.g., an aerosol dispenser, a pump spray, a trigger spray or a squeeze bottle, to apply a composition to a site of skin and/or thinning hair or baldness.

Aspects of the present invention can also be described as follows:

1. A compound of formula I disclosed herein, wherein ARA is an AR antagonist, L is a linker molecule and EE is an AR elimination promoter or elimination enhancer element.
2. The compound of embodiment 1, wherein the AR antagonist includes apalutamide, bicalutamide, canrenone, chlormadinone acetate, cimetidine, Compound ARA 1, cyproterone acetate, drospirenone, enzalutamide, flutamide, ketoconazole, megestrol acetate, methoxybenzyl lactam, nilutamide, RU58841, spironolactone, ortopilutamide (fluridil).
3. The compound of embodiment 1 or 2, wherein the linker molecule is formula II disclosed herein, wherein $R^1$ and $R^2$ are each independently H, OH, COOH, $NH_2$, $R^3$OH, $R^3$COOH, OR$^3$OH, OR$^3$COOH, $R^3$NH(CO) $R^4$, $R^3$NH(CO) $R^4$OH, $R^3$NH(CO) $R^4$COOH; $R^3$ and $R^4$ are each independently $C_{1-10}$ alkyl, $C_{2-10}$ alkenyl, or $C_{2-10}$ alkynyl; and n any integer from 0 to 10.
4. The compound of embodiment 3, wherein $R^1$ and $R^2$ are each independently H, OH, COOH, $NH_2$, $R^3$OH, $R^3$COOH, OR$^3$OH, OR$^3$COOH, $R^3$NH(CO) $R^4$, $R^3$NH (CO) $R^4$OH, or $R^3$NH(CO) $R^4$COOH; $R^3$ and $R^4$ are each independently $C_{1-6}$ alkyl, $C_{2-6}$ alkenyl, or $C_{2-6}$ alkynyl; and n any integer from 0 to 10.
5. The compound of embodiment 4, wherein $R^1$ and $R^2$ are each independently H, OH, COOH, $NH_2$, $R^3$OH, $R^3$COOH, OR$^3$OH, OR$^3$COOH, $R^3$NH(CO) $R^4$, $R^3$NH (CO) $R^4$OH, or $R^3$NH(CO) $R^4$COOH; $R^3$ and $R^4$ are each independently $C_{1-4}$ alkyl, $C_{2-4}$ alkenyl, or $C_{2-4}$ alkynyl; and n any integer from 0 to 5.
6. The compound of embodiment 3, wherein $R^1$ and $R^2$ are each independently H, OH, COOH, $NH_2$, $R^3$OH, $R^3$COOH, OR$^3$OH, OR$^3$COOH, or $R^3$NH(CO) $R^4$OH; $R^3$ and $R^4$ are each independently $C_{1-10}$ alkyl; and n any integer from 0 to 10.
7. The compound of embodiment 6, wherein $R^1$ and $R^2$ are each independently H, OH, COOH, $NH_2$, $R^3$OH, $R^3$COOH, OR$^3$OH, OR$^3$COOH, or $R^3$NH(CO) $R^4$OH; $R^3$ and $R^4$ are each independently $C_{1-6}$ alkyl; and n any integer from 0 to 10.
8. The compound of embodiment 7, wherein $R^1$ and $R^2$ are each independently H, OH, COOH, $NH_2$, $R^3$OH, $R^3$COOH, OR$^3$OH, OR$^3$COOH, or $R^3$NH(CO) $R^4$OH; $R^3$ and $R^4$ are each independently $C_{1-6}$ alkyl; and n any integer from 0 to 5.
9. The compound of embodiment 3, wherein $R^1$ is OH, COOH, $NH_2$, $R^3$OH, $R^3$COOH, or $R^3$NH(CO) $R^4$OH; $R^2$ is OH, COOH, $NH_2$, $R^3$COOH, or OR$^3$COOH, $R^3$ and $R^4$ are each independently $C_{1-10}$ alkyl; and n any integer from 0 to 10.
10. The compound of embodiment 9, wherein $R^1$ is OH, COOH, $NH_2$, $R^3$OH, $R^3$COOH, or $R^3$NH(CO) $R^4$OH; $R^2$ is OH, COOH, $NH_2$, $R^3$COOH, or OR$^3$COOH, $R^3$ and $R^4$ are each independently $C_{1-6}$ alkyl; and n any integer from 0 to 10.
11. The compound of embodiment 10, wherein $R^1$ is OH, COOH, $NH_2$, $R^3$OH, $R^3$COOH, or $R^3$NH(CO) $R^4$OH; $R^2$ is OH, COOH, $NH_2$, $R^3$COOH, or OR$^3$COOH, $R^3$ and $R^4$ are each independently $C_{1-6}$ alkyl; and n any integer from 0 to 5.

12. The compound of embodiment 11, wherein $R^1$ is OH, $R^3$OH, $R^3$COOH, or $R^3$NH(CO) $R^4$OH; $R^2$ is OH, COOH, $NH_2$, $R^3$COOH, or $OR^3$COOH, $R^3$ and $R^4$ are each independently $C_{1-6}$ alkyl; and n any integer from 0 to 5.

13. The compound of embodiment 12, wherein $R^1$ is OH, $R^3$OH, $R^3$COOH, or $R^3$NH(CO) $R^4$OH; $R^2$ is OH, COOH, $NH_2$, $R^3$COOH, or $OR^3$COOH, $R^3$ and $R^4$ are each independently $C_{1-4}$ alkyl; and n any integer from 0 to 4.

14. The compound of embodiment 13, wherein $R^1$ is OH, C—C—OH, C—COOH, or C—C—NH—CO—C—C—C—OH; $R^2$ is OH, COOH, $NH_2$, C—COOH, or O—C—COOH; and n any integer from 0 to 10.

15. The compound of embodiment 14, wherein $R^1$ is OH, C—C—OH, C—COOH, or C—C—NH—CO—C—C—C—OH; $R^2$ is OH, COOH, $NH_2$, C—COOH, or O—C—COOH; and n any integer from 0 to 8.

16. The compound of embodiment 15, wherein $R^1$ is OH, C—C—OH, C—COOH, or C—C—NH—CO—C—C—C—OH; $R^2$ is OH, COOH, $NH_2$, C—COOH, or O—C—COOH; and n any integer from 0 to 6.

17. The compound of embodiment 16, wherein $R^1$ is OH, C—C—OH, C—COOH, or C—C—NH—CO—C—C—C—OH; $R^2$ is OH, COOH, $NH_2$, C—COOH, or O—C—COOH; and n any integer from 0 to 4.

18. The compound of any one of embodiments 1-3, wherein the linker molecule is formula III disclosed herein, wherein n any integer from 0 to 10.

19. The compound of embodiment 18, wherein n any integer from 0 to 8, or any integer from 0 to 6, or any integer from 0 to 4.

20. The compound of any one of embodiments 1-3, 18 or 19, wherein the linker molecule is

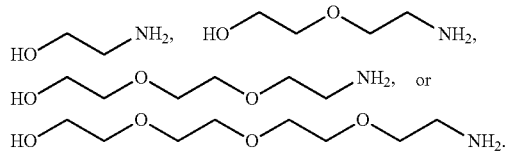

21. The compound of any one of embodiments 1-3, wherein the linker molecule is formula IV disclosed herein, wherein n any integer from 0 to 10.

22. The compound of embodiment 21, wherein n any integer from 0 to 8, or any integer from 0 to 6, or any integer from 0 to 4.

23. The compound of any one of embodiments 1-3, 21 or 22, wherein the linker molecule is

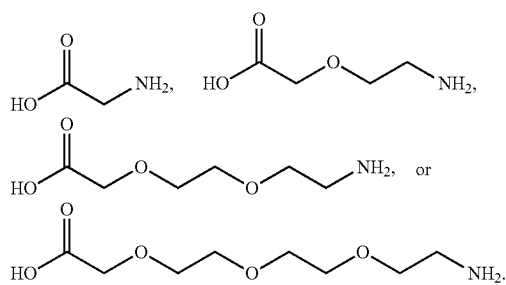

24. The compound of any one of embodiments 1-3, wherein the linker molecule is formula V disclosed herein, wherein n any integer from 0 to 10.

25. The compound of embodiment 24, wherein n any integer from 0 to 8, or any integer from 0 to 6, or any integer from 0 to 4.

26. The compound of any one of embodiments 1-3, 24 or 25, wherein the linker molecule is

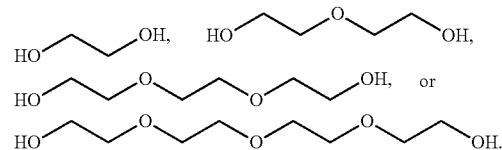

27. The compound of any one of embodiments 1-3, wherein the linker molecule is formula VI disclosed herein, wherein n any integer from 0 to 10.

28. The compound of embodiment 27, wherein n any integer from 0 to 8, or any integer from 0 to 6, or any integer from 0 to 4.

29. The compound of any one of embodiments 1-3, 27 or 28, wherein the linker molecule is

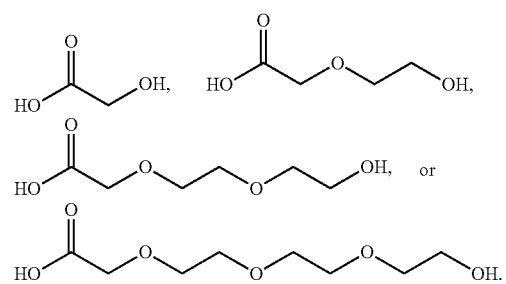

30. The compound of any one of embodiments 1-3, wherein the linker molecule is formula VII disclosed herein, wherein n any integer from 0 to 10.

31. The compound of embodiment 30, wherein n any integer from 0 to 8, or any integer from 0 to 6, or any integer from 0 to 4.

32. The compound of any one of embodiments 1-3, 30 or 31, wherein the linker molecule is

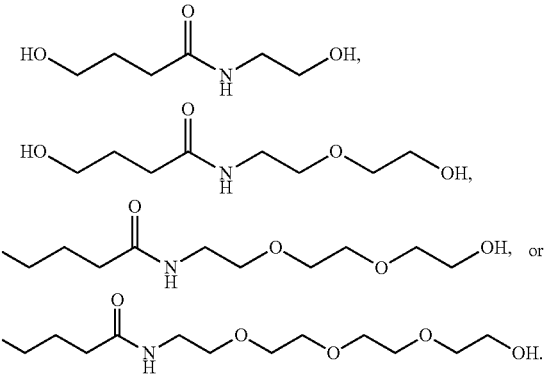

33. The compound of any one of embodiments 1-3, wherein the linker molecule is formula VIII disclosed herein, wherein n any integer from 0 to 10.

34. The compound of embodiment 33, wherein n any integer from 0 to 8, or any integer from 0 to 6, or any integer from 0 to 4.
35. The compound of any one of embodiments 1-3, 33 or 34, wherein the linker molecule is

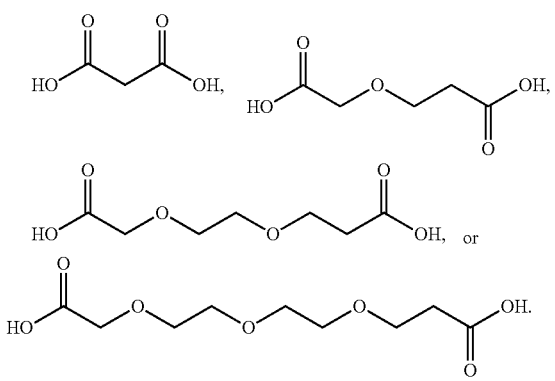

36. The compound of any one of embodiments 1-3, wherein the linker molecule is formula IX disclosed herein, wherein n any integer from 0 to 10.
37. The compound of embodiment 36, wherein n any integer from 0 to 8, or any integer from 0 to 6, or any integer from 0 to 4.
38. The compound of any one of embodiments 1-3, 36 or 37, wherein the linker molecule is

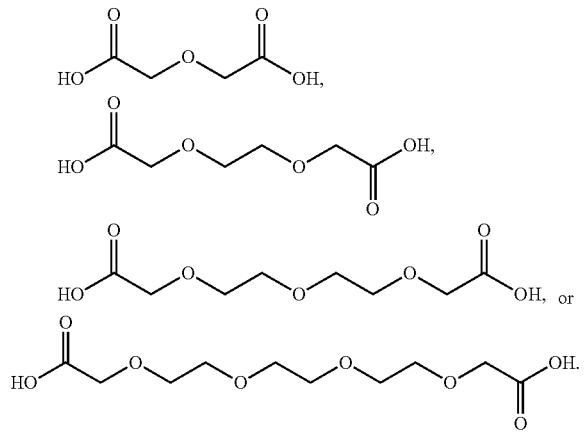

39. The compound of any one of embodiments 1-3, wherein the linker molecule is formula X disclosed herein, wherein n any integer from 0 to 10.
40. The compound of embodiment 39, wherein n any integer from 0 to 8, or any integer from 0 to 6, or any integer from 0 to 4.
41. The compound of any one of embodiments 1-3, 39 or 40, wherein the linker molecule is

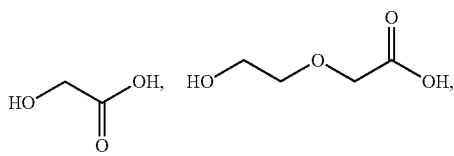

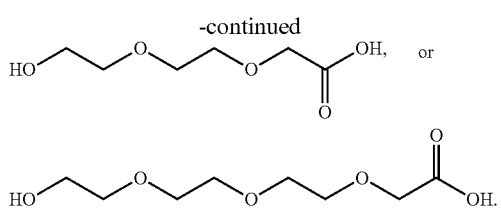

42. The compound of any one of embodiments 1-41, wherein the AR eliminator promoter or enhancing element is a hydrophobic tag or an E3 ligase-recruiting moiety.
43. The compound of embodiment 42, wherein the hydrophobic tag is an adamantane moiety.
44. The compound of embodiment 43, wherein the adamantane moiety is formula XI disclosed herein, wherein $R^5$ is H, OH, COOH, $NH_2$, a halogen, $R^6OH$, $R^6COOH$, $R^6C(O)$ $NH_2$, or $R^6C(O)$ $R^7$; $R^6$ is $C_{1-10}$ alkyl, $C_{2-10}$ alkenyl, or $C_{2-10}$ alkynyl; and $R^7$ is a halogen.
45. The compound of embodiment 44, wherein $R^5$ is H, OH, COOH, $NH_2$, a halogen, $R^6OH$, $R^6COOH$, $R^6C(O)$ $NH_2$ or $R^6C(O)$ $R^7$; $R^6$ is $C_{1-6}$ alkyl, $C_{2-6}$ alkenyl, or $C_{2-6}$ alkynyl; and $R^7$ is a halogen.
46. The compound of embodiment 45, wherein $R^5$ is H, OH, COOH, $NH_2$, a halogen, $R^6OH$, $R^6COOH$, $R^6C(O)$ $NH_2$ or $R^6C(O)$ $R^7$; $R^6$ is $C_{1-4}$ alkyl, $C_{2-4}$ alkenyl, or $C_{2-4}$ alkynyl; and $R^7$ is a halogen.
47. The compound of any one of embodiments 44-46, wherein the halogen is fluorine, chlorine, bromine, iodine, astatine or ununseptium.
48. The compound of any one of embodiments 44-47, wherein $R^5$ is H, OH, COOH, $NH_2$, F, Br, Cl, I, $R^6OH$, $R^6COOH$, $ROC(O)$ $NH_2$ or $R^6C(O)$ $R^7$; $R^6$ is $C_{1-6}$ alkyl, $C_{2-6}$ alkenyl, or $C_{2-6}$ alkynyl; and $R^7$ is a F, Br, Cl or I.
49. The compound of any one of embodiments 44-48, wherein the adamantane moiety is

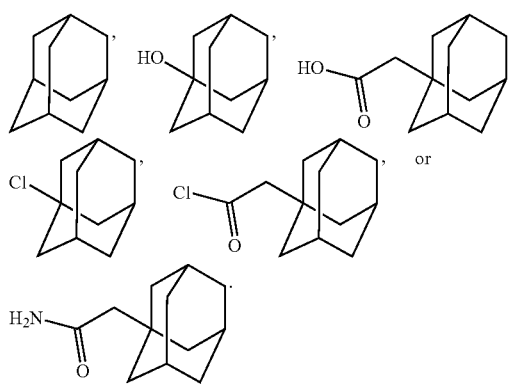

50. The compound of embodiment 42, wherein the hydrophobic tag is a Boc-protected amino acid.
51. The compound of embodiment 50, wherein the Boc-protected amino acid includes a glutamine, arginine, glutamic acid, phenylalanine, aspartic acid, cysteine, lysine or asparagine.
52. The compound of embodiment 50 or 51, wherein the Boc-protected amino acid a tert-butyl carbamate-protected arginine ($BOC_3Arg$) moiety, an iso-butyl carbamate-protected lysine ($BOC_2Lys$) moiety, an iso-butyl carbamate-protected aspartic acid (BOC₂Asp) moiety, an iso-butyl carbamate-protected asparagine (BOC₂Asn) moiety, an iso-butyl carbamate-protected glutamic acid (BOC₂Glu) moiety, or an iso-butyl carbamate-protected glutamine (BOC₂Gln) moiety.

53. The compound of any one of embodiments 50-52, wherein the Boc-protected amino acid is

[chemical structures of Boc-protected amino acids: arginine, lysine, aspartate, asparagine, glutamate, glutamine]

54. The compound of embodiment 42, wherein the E3 ligase-recruiting moiety is a hypoxia-inducible factor 1a (HIF-1α) moiety.
55. The compound of embodiment 54, wherein the HIF-1α moiety is formula XII disclosed herein, wherein $R^8$ is H, OH, COOH, NH$_2$, a halogen, $R^9$OH, $R^9$COOH, $R^6$C(O) NH$_2$, or $R^6$C(O) $R^{10}$; $R^9$ is C$_{1-10}$ alkyl, C$_{2-10}$ alkenyl, or C$_{2-10}$ alkynyl; and $R^{10}$ is a halogen.
56. The compound of embodiment 55, wherein $R^8$ is H, OH, COOH, NH$_2$, a halogen, $R^9$OH, $R^9$COOH, $R^6$C(O) NH$_2$, or $R^6$C(O) $R^{10}$; $R^9$ is C$_{1-6}$ alkyl, C$_{2-6}$ alkenyl, or C$_{2-6}$ alkynyl; and $R^{10}$ is a halogen.
57. The compound of embodiment 56, wherein $R^8$ is H, OH, COOH, NH$_2$, a halogen, $R^9$OH, $R^9$COOH, $R^6$C(O) NH$_2$, or $R^6$C(O) $R^{10}$; $R^9$ is C$_{1-4}$ alkyl, C$_{2-4}$ alkenyl, or C$_{2-4}$ alkynyl; and $R^{10}$ is a halogen.
58. The compound of any one of embodiments 55-57, wherein the halogen is fluorine, chlorine, bromine, iodine, astatine or ununseptium.
59. The compound of any one of embodiments 55-58, wherein $R^8$ is H, OH, COOH, NH$_2$, F, Br, Cl, I, $R^9$OH, $R^9$COOH, $R^6$C(O) NH$_2$, or $R^6$C(O) $R^{10}$; $R^9$ is C$_{1-6}$ alkyl, C$_{2-6}$ alkenyl, or C$_{2-6}$ alkynyl; and $R^{10}$ is a F, Br, Cl or I.
60. The compound of any one of embodiments 55-59, wherein the HIF-1α moiety is

[chemical structure of HIF-1α moiety]

61. The compound of embodiment 42, wherein the E3 ligase-recruiting moiety is a Nutlin moiety.
62. The compound of embodiment 61, wherein the Nutlin moiety is formula XIII disclosed herein, wherein $R^{11}$ is H, OH, COOH, NH$_2$, a halogen, $R^{12}$OH, $R^{12}$COOH, $R^{12}$C(O) NH$_2$, or $R^{12}$C(O) $R^{13}$; $R^{12}$ is C$_{1-10}$ alkyl, C$_{2-10}$ alkenyl, or C$_{2-10}$ alkynyl; and $R^{13}$ is a halogen.
63. The compound of embodiment 62, wherein $R^{11}$ is H, OH, COOH, NH$_2$, a halogen, $R^{12}$OH, $R^{12}$COOH, $R^{12}$C(O) NH$_2$, or $R^{12}$C(O) $R^{13}$; $R^{12}$ is C$_{1-6}$ alkyl, C$_{2-6}$ alkenyl, or C$_{2-6}$ alkynyl; and $R^{13}$ is a halogen.
64. The compound of embodiment 63, wherein $R^{11}$ is H, OH, COOH, NH$_2$, a halogen, $R^{12}$OH, $R^{12}$COOH, $R^{12}$C(O) NH$_2$, or $R^{12}$C(O) $R^{13}$; $R^{12}$ is C$_{1-4}$ alkyl, C$_{2-4}$ alkenyl, or C$_{2-4}$ alkynyl; and $R^{13}$ is a halogen.
65. The compound of any one of embodiments 62-64, wherein the halogen is fluorine, chlorine, bromine, iodine, astatine or ununseptium.
66. The compound of any one of embodiments 62-65, wherein $R^{11}$ is H, OH, COOH, NH$_2$, F, Br, Cl, I, $R^{12}$OH, $R^{12}$COOH, $R^{12}$C(O) NH$_2$, or $R^{12}$C(O) $R^{13}$; $R^{12}$ is C$_{1-6}$ alkyl, C$_{2-6}$ alkenyl, or C$_{2-6}$ alkynyl; and $R^{13}$ is a F, Br, Cl or I.
67. The compound of embodiment 42, wherein the E3 ligase-recruiting moiety is a bestatin moiety.
68. The compound of embodiment 61, wherein the bestatin moiety is formula XIV disclosed herein, wherein $R^{14}$ is H, OH, COOH, NH$_2$, a halogen, $R^{15}$OH, $R^{15}$COOH, $R^{15}$C(O) NH$_2$, or $R^{15}$C(O) $R^{16}$; $R^{15}$ is C$_{1-10}$ alkyl, C$_{2-10}$ alkenyl, or C$_{2-10}$ alkynyl; and $R^{16}$ is a halogen.
69. The compound of embodiment 68, wherein $R^{14}$ is H, OH, COOH, NH$_2$, a halogen, $R^{15}$OH, $R^{15}$COOH, $R^{15}$C(O) NH$_2$, or $R^{15}$C(O) $R^{16}$; $R^{15}$ is C$_{1-6}$ alkyl, C$_{2-6}$ alkenyl, or C$_{2-6}$ alkynyl; and $R^{16}$ is a halogen.
70. The compound of embodiment 69, wherein $R^{14}$ is H, OH, COOH, NH$_2$, a halogen, $R^{15}$OH, $R^{15}$COOH, $R^{15}$C(O) NH$_2$, or $R^{15}$C(O) $R^{16}$; $R^{15}$ is C$_{1-4}$ alkyl, C$_{2-4}$ alkenyl, or C$_{2-4}$ alkynyl; and $R^{16}$ is a halogen.
71. The compound of any one of embodiments 68-70, wherein the halogen is fluorine, chlorine, bromine, iodine, astatine or ununseptium.
72. The compound of any one of embodiments 68-71, wherein $R^{14}$ is H, OH, COOH, NH$_2$, F, Br, Cl, I, $R^{15}$OH, $R^{15}$COOH, $R^{15}$C(O) NH$_2$, or $R^{15}$C(O) $R^{16}$; $R^{15}$ is C$_{1-6}$ alkyl, C$_{2-6}$ alkenyl, or C$_{2-6}$ alkynyl; and $R^{16}$ is a F, Br, Cl or I.
73. The compound of embodiment 42, wherein the E3 ligase-recruiting moiety is a phthalimide moiety.
74. The compound of embodiment 61, wherein the phthalimide moiety is formula XV disclosed herein, wherein $R^{17}$ is H, OH, COOH, NH$_2$, a halogen, $R^{19}$OH, $R^{19}$COOH, $R^{19}$C(O) NH$_2$, or $R^{19}$C(O) $R^{20}$, NHR$^{19}$OH, NHR$^{19}$COOH, NHR$^{19}$C(O) NH$_2$, or NHR$^{19}$C(O) $R^{20}$;

$R^{18}$ is H, OH, O, COOH, or $C_{1-6}$; $R^{19}$ is $C_{1-10}$ alkyl, $C_{2-10}$ alkenyl, or $C_{2-10}$ alkynyl; and $R^{20}$ is a halogen.

75. The compound of embodiment 74, wherein $R^{17}$ is H, OH, COOH, $NH_2$, a halogen, $R^{19}OH$, $R^{19}COOH$, $R^{19}C(O) NH_2$, or $R^{19}C(O) R^{20}$, $NHR^{19}OH$, $NHR^{19}COOH$, $NHR^{19}C(O) NH_2$, or $NHR^{19}C(O) R^{20}$; $R^{18}$ is H, OH, O, COOH, or $C_{1-6}$; $R^{19}$ is $C_{1-6}$ alkyl, $C_{2-6}$ alkenyl, or $C_{2-6}$ alkynyl; and $R^{20}$ is a halogen.

76. The compound of embodiment 75, wherein $R^{17}$ is H, OH, COOH, $NH_2$, a halogen, $R^{19}OH$, $R^{19}COOH$, $R^{19}C(O) NH_2$, or $R^{19}C(O) R^{20}$, $NHR^{19}OH$, $NHR^{19}COOH$, $NHR^{19}C(O) NH_2$, or $NHR^{19}C(O) R^{20}$; $R^{18}$ is H, OH, O, COOH, or $C_{1-6}$; $R^{19}$ is $C_{1-4}$ alkyl, $C_{2-4}$ alkenyl, or $C_{2-4}$ alkynyl; and $R^{20}$ is a halogen.

77. The compound of any one of embodiments 74-76, wherein the halogen is fluorine, chlorine, bromine, iodine, astatine or ununseptium.

78. The compound of any one of embodiments 74-78, wherein $R^{17}$ is H, OH, COOH, $NH_2$, F, Br, Cl, I, $R^{19}OH$, $R^{19}COOH$, $R^{19}C(O) NH_2$, or $R^{19}C(O) R^{20}$, $NHR^{19}OH$, $NHR^{19}COOH$, $NHR^{19}C(O) NH_2$, or $NHR^{19}C(O) R^{20}$; $R^{18}$ is H, OH, O, COOH, or $C_{1-6}$; $R^{19}$ is $C_{1-6}$ alkyl, $C_{2-6}$ alkenyl, or $C_{2-6}$ alkynyl; and $R^{20}$ is a F, Br, Cl or I.

79. The compound of embodiment 73 or 74, wherein the phthalimide moiety is any one of formulas XVI disclosed herein, XVII, XVIII or XIX, wherein $R^{20}$ is H, OH, COOH, $NH_2$, a halogen, $R^{21}OH$, $R^{21}COOH$, $R^{21}C(O) NH_2$, or $R^{21}C(O) R^{22}$; $R^{21}$ is $C_{1-10}$ alkyl, $C_{2-10}$ alkenyl, or $C_{2-10}$ alkynyl; and $R^{22}$ is a halogen.

80. The compound of embodiment 79, wherein $R^{20}$ is H, OH, COOH, $NH_2$, a halogen, $R^{21}OH$, $R^{21}COOH$, $R^{21}C(O) NH_2$, or $R^{21}C(O) R^{22}$; $R^{21}$ is $C_{1-6}$ alkyl, $C_{2-6}$ alkenyl, or $C_{2-6}$ alkynyl; and $R^{22}$ is a halogen.

81. The compound of embodiment 80, wherein $R^{20}$ is H, OH, COOH, $NH_2$, a halogen, $R^{21}OH$, $R^{21}COOH$, $R^{21}C(O) NH_2$, or $R^{21}C(O) R^{22}$; and $R^{21}$ is $C_{1-4}$ alkyl, $C_{2-4}$ alkenyl, or $C_{2-4}$ alkynyl; and $R^{22}$ is a halogen.

82. The compound of any one of embodiments 79-81, wherein the halogen is fluorine, chlorine, bromine, iodine, astatine or ununseptium.

83. The compound of any one of embodiments 79-82, wherein $R^{20}$ is H, OH, COOH, $NH_2$, F, Br, Cl, I, $R^{21}OH$, $R^{21}COOH$, $R^{21}C(O) NH_2$, or $R^{21}C(O) R^{22}$; and $R^{21}$ is $C_{1-6}$ alkyl, $C_{2-6}$ alkenyl, or $C_{2-6}$ alkynyl; and $R^{22}$ is a F, Br, Cl or I.

84. The compound of any one of embodiments 1-83, wherein the compound is of formula XX disclosed herein, wherein n any integer from 0 to 10.

85. The compound of embodiment 84, wherein n any integer from 0 to 8, or any integer from 0 to 6, or any integer from 0 to 4.

86. The compound of embodiment 84 or 85, wherein the compound is Compound 38 or Compound 39.

87. The compound of any one of embodiments 1-83, wherein the compound is Compound 37.

88. The compound of any one of embodiments 1-83, wherein the compound is of formula XXI disclosed herein, wherein n any integer from 0 to 10.

89. The compound of embodiment 88, wherein n any integer from 0 to 8, or any integer from 0 to 6, or any integer from 0 to 4.

90. The compound of embodiment 88 or 89, wherein the compound is Compound 41 or Compound 42.

91. The compound of any one of embodiments 1-83, wherein the compound is Compound 40.

92. The compound of any one of embodiments 1-83, wherein the compound is of formula XXII disclosed herein, wherein n any integer from 0 to 10.

93. The compound of embodiment 92, wherein n any integer from 0 to 8, or any integer from 0 to 6, or any integer from 0 to 4.

94. The compound of embodiment 92 or 93, wherein the compound is Compound 43, Compound 44, Compound 45, or Compound 46.

95. The compound of any one of embodiments 1-83, wherein the compound is of formula XXIII disclosed herein, wherein n any integer from 0 to 10.

96. The compound of embodiment 95, wherein n any integer from 0 to 8, or any integer from 0 to 6, or any integer from 0 to 4.

97. The compound of embodiment 95 or 96, wherein the compound is Compound 47, Compound 48, Compound 49, or Compound 50.

98. The compound of any one of embodiments 1-83, wherein the compound is Compound 51, Compound 52, Compound 53, or Compound 54.

99. A pharmaceutical composition comprising one or more compounds defined in any one of embodiments 1-98.

100. The pharmaceutical composition of embodiment 99, wherein the one or more compounds are in an amount of about 1 µg, about 2 µg, about 3 µg, about 4 µg, about 5 µg, about 6 µg, about 7 µg, about 8 µg, about 9 µg, about 10 µg, about 15 µg, about 20 µg, about 25 µg, about 30 µg, about 35 µg, about 40 µg, about 45 µg, about 50 µg, about 55 µg, about 60 µg, about 65 µg, about 70 µg, about 75 µg, about 80 µg, about 85 µg, about 90 µg, about 95 µg, about 100 µg, about 110 µg, about 120 µg, about 130 µg, about 140 µg, about 150 µg, about 160 µg, about 170 µg, about 180 µg, about 190 µg, about 200 µg, about 210 µg, about 220 µg, about 230 µg, about 240 µg, about 250 µg, 260 µg, about 270 µg, about 280 µg, about 290 µg, about 300 µg, about 310 µg, about 320 µg, about 330 µg, about 340 µg, about 350 µg, 360 µg, about 370 µg, about 380 µg, about 390 µg, about 400 µg, about 410 µg, about 420 µg, about 430 µg, about 440 µg, about 450 µg, 460 µg, about 470 µg, about 480 µg, about 490 µg, about 500 µg, about 510 µg, about 520 µg, about 530 µg, about 540 µg, about 550 µg, about 560 µg, about 570 µg, about 580 µg, about 590 µg, about 600 µg, about 610 µg, about 620 µg, about 630 µg, about 640 µg, about 650 µg, 660 µg, about 670 µg, about 680 µg, about 690 µg, about 700 µg, about 710 µg, about 720 µg, about 730 µg, about 740 µg, about 750 µg, 760 µg, about 770 µg, about 780 µg, about 790 µg, about 800 µg, about 810 µg, about 820 µg, about 830 µg, about 840 µg, about 850 µg, 860 µg, about 870 µg, about 880 µg, about 890 µg, about 900 µg, about 910 µg, about 920 µg, about 930 µg, about 940 µg, about 950 µg, 960 µg, about 970 µg, about 980 µg, about 990 µg, or about 1,000 µg, or in an amount of at least 1 µg, at least 2 µg, at least 3 µg, at least 4 µg, at least 5 µg, at least 6 µg, at least 7 µg, at least 8 µg, at least 9 µg, at least 10 µg, at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 110 µg, at least 120 µg, at least 130 µg, at least 140 µg, at least 150 µg, at least 160 µg, at least 170 µg, at least 180 µg, at least 190 µg, at least 200 µg, at least 210 µg, at least 220 µg, at least 230 µg, at least 240 µg, at least 250 µg, 260 µg, at least 270 µg, at least 280 µg, at least 290 µg, at least 300 µg, at least 310 µg, at least 320 µg, at least 330 µg, at least 340 µg, at least 350 µg, 360 µg, at least 370 µg, at least 380 µg, at least 390 µg, at least 400 µg, at least 410 µg, at least 420 µg, at least 430 µg, at least 440 µg, at least 450 µg, 460 µg, at least 470 µg, at least 480 µg, at least 490 µg, at least 500 µg, at least 510 µg, at least 520 µg, at least 530 µg, at least 540 µg, at least 550 µg, 560 µg, at least 570 µg, at least 580 µg, at least 590 µg, at least 600 µg, at least 610 µg, at least 620 µg, at least 630 µg, at least 640 µg, at least 650 µg, 660 µg, at least 670 µg, at least 680 µg, at least 690 µg, at least 700 µg, at least 710 µg, at least 720 µg, at least 730 µg, at least 740 µg, at least 750 µg, 760 µg, at least 770 µg, at least 780 µg, at least 790 µg, at least 800 µg, at least 810 µg, at least 820 µg, at least 830 µg, at least 840 µg, at least 850 µg, 860 µg, at least 870 µg, at least 880 µg, at least 890 µg, at least 900 µg, at least 910 µg, at least 920 µg, at least 930 µg, at least 940 µg, at least 950 µg, 960 µg, at least 970 µg, at least 980 µg, at least 990 µg, or at least 1,000 µg, or in an amount of at most 1 µg, at most 2 µg, at most 3 µg, at most 4 µg, at most 5 µg, at most 6 µg, at most 7 µg, at most 8 µg, at most 9 µg, at most 10 µg, at most 15 µg, at most 20 µg, at most 25 µg, at most 30 µg, at most 35 µg, at most 40 µg, at most 45 µg, at most 50 µg, at most 55 µg, at most 60 µg, at most 65 µg, at most 70 µg, at most 75 µg, at most 80 µg, at most 85 µg, at most 90 µg, at most 95 µg, at most 100 µg, at most 110 µg, at most 120 µg, at most 130 µg, at most 140 µg, at most 150 µg, at most 160 µg, at most 170 µg, at most 180 µg, at most 190 µg, at most 200 µg, at most 210 µg, at most 220 µg, at most 230 µg, at most 240 µg, at most 250 µg, 260 µg, at most 270 µg, at most 280 µg, at most 290 µg, at most 300 µg, at most 310 µg, at most 320 µg, at most 330 µg, at most 340 µg, at most 350 µg, 360 µg, at most 370 µg, at most 380 µg, at most 390 µg, at most 400 µg, at most 410 µg, at most 420 µg, at most 430 µg, at most 440 µg, at most 450 µg, 460 µg, at most 470 µg, at most 480 µg, at most 490 µg, at most 500 µg, at most 510 µg, at most 520 µg, at most 530 µg, at most 540 µg, at most 550 µg, 560 µg, at most 570 µg, at most 580 µg, at most 590 µg, at most 600 µg, at most 610 µg, at most 620 µg, at most 630 µg, at most 640 µg, at most 650 µg, 660 µg, at most 670 µg, at most 680 µg, at most 690 µg, at most 700 µg, at most 710 µg, at most 720 µg, at most 730 µg, at most 740 µg, at most 750 µg, 760 µg, at most 770 µg, at most 780 µg, at most 790 µg, at most 800 µg, at most 810 µg, at most 820 µg, at most 830 µg, at most 840 µg, at most 850 µg, 860 µg, at most 870 µg, at most 880 µg, at most 890 µg, at most 900 µg, at most 910 µg, at most 920 µg, at most 930 µg, at most 940 µg, at most 950 µg, 960 µg, at most 970 µg, at most 980 µg, at most 990 µg, or at most 1,000 µg.

101. The pharmaceutical composition of embodiment 99, wherein the one or more compounds are in an amount of about 1 µg to about 10 µg, about 1 µg to about 20 µg, about 1 µg to about 30 µg, about 1 µg to about 40 µg, about 1 µg to about 50 µg, about 1 µg to about 60 µg, about 1 µg to about 70 µg, about 1 µg to about 80 µg, about 1 µg to about 90 µg, about 1 µg to about 100 µg, about 1 µg to about 110 µg, about 1 µg to about 120 µg, about 1 µg to about 130 µg, about 1 µg to about 140 µg, about 1 µg to about 150 µg, about 5 µg to about 10 µg, about 5 µg to about 20 µg, about 5 µg to about 30 µg, about 5 µg to about 40 µg, about 5 µg to about 50 µg, about 5 µg to about 60 µg, about 5 µg to about 70 µg, about 5 µg to about 80 µg, about 5 µg to about 90 µg, about 5 µg to about 100 µg, about 5 µg to about 110 µg, about 5 µg to about 120 µg, about 5 µg to about 130 µg, about 5 µg to about 140 µg, about 5 µg to about 150 µg, about 10 µg to about 20 µg, about 10 µg to about 30 µg, about 10 µg to about 40 µg, about 10 µg to about 50 µg, about 10 µg to about 60 µg, about 10 µg to about 70 µg, about 10 µg to about 80 µg, about 10 µg to about 90 µg, about 10 µg to about 100 µg, about 10 µg to about 110 µg, about 10 µg to about 120 µg, about 10 µg to about 130 µg, about 10 µg to about 140 µg, about 10 µg to about 150 µg, about 10 µg to about 175 µg, about 10 µg to about 200 µg, about 10 µg to about 225 µg, about 10 µg to about 250 µg, about 25 µg to about 50 µg, about 25 µg to about 75 µg, about 25 µg to about 100 µg, about 25 µg to about 125 µg, about 25 µg to about 150 µg, about 25 µg to about 175 µg, about 25 µg to about 200 µg, about 25 µg to about 225 µg, about 25 µg to about 250 µg, about 50 µg to about 75 µg, about 50 µg to about 100 µg, about 50 µg to about 125 µg, about 50 µg to about 150 µg, about 50 µg to about 175 µg, about 50 µg to about 200 µg, about 50 µg to about 225 µg, about 50 µg to about 250 µg, about 75 µg to about 100 µg, about 75 µg to about 125 µg, about 75 µg to about 150 µg, about 75 µg to about 175 µg, about 75 µg to about 200 µg, about 75 µg to about 225 µg, about 75 µg to about 250 µg, about 100 µg to about 125 µg, about 100 µg to about 150 µg, about 100 µg to about 175 µg, about 100 µg to about 200 µg, about 100 µg to about 225 µg, about 100 µg to about 250 µg, about 100 µg to about 275 µg, about 100 µg to about 300 µg, about 100 µg to about 325 µg, about 100 µg to about 350 µg, about 100 µg to about 375 µg, about 100 µg to about 400 µg, about 100 µg to about 425 µg, about 100 µg to about 450 µg, about 100 µg to about 475 µg, about 100 µg to about 500 µg, about 100 µg to about 525 µg, about 100 µg to about 550 µg, about 100 µg to about 575 µg, about 100 µg to about 600 µg, about 125 µg to about 150 µg, about 125 µg to about 175 µg, about 125 µg to about 200 µg, about 125 µg to about 225 µg, about 125 µg to about 250 µg, about 125 µg to about 275 µg, about 125 µg to about 300 µg, about 125 µg to about 325 µg, about 125 µg to about 350 µg, about 125 µg to about 375 µg, about 125 µg to about 400 µg, about 125 µg to about 425 µg, about 125 µg to about 450 µg, about 125 µg to about 475 µg, about 125 µg to about 500 µg, about 125 µg to about 525 µg, about 125 µg to about 550 µg, about 125 µg to about 575 µg, about 125 µg to about 600 µg, about 150 µg to about 175 µg, about 150 µg to about 200 µg, about 150 µg to about 225 µg, about 150 µg to about 250 µg, about 150 µg to about 275 µg, about 150 µg to about 300 µg, about 150 µg to about 325 µg, about 150 µg to about 350 µg, about 150 µg to about 375 µg, about 150 µg to about 400 µg, about 150 µg to about 425 µg, about 150 µg to about 450 µg, about 150 µg to about 475 µg, about 150 µg to about 500 µg, about 150 µg to about 525 µg, about 150 µg to about 550 µg, about 150 µg to about 575 µg, about 150 µg to about 600 µg, about 200 µg to about 225 µg, about 200 µg to about 250 µg, about 200 µg to about 275 µg, about 200 µg to about 300 µg, about 200 µg to about 325 µg, about 200 µg to about 350 µg, about 200 µg to about 375 µg, about 200 µg to about 400 µg, about 200 µg to about 425 µg, about 200 µg to about 450 µg, about 200 µg to about 475 µg, about 200 µg to about 500 µg, about 200 µg to about 525 µg, about 200 µg to about 550 µg, about 200 µg to about 575 µg, about 200 µg to about 600 µg, about 200 µg to about 625 µg, about 200 µg to about 650 µg, about 200 µg to about 675 µg, about 200 µg to about 700 µg, about 200 µg to about 725 µg, about 200 µg to about 750 µg, about 200 µg to about 775 µg, about 200 µg to about 800 µg, about 200 µg to about 825 µg, about 200 µg to about 850 µg, about 200 µg to about 875 µg, about 200 µg to about 900 µg, about 200 µg to about 925 µg, about 200 µg to about 950 µg, about 200 µg to about 975 µg, about 200 µg to about 1,000 µg, about 250 µg to about 275 µg, about 250 µg to about 300 µg, about 250 µg to about 325 µg, about 250 µg to about 350 µg, about 250 µg to about 375 µg, about 250 µg to about 400 µg, about 250 µg to about 425 µg, about 250 µg to about 450 µg, about 250 µg to about 475 µg, about 250 µg to about 500 µg, about 250 µg to about 525 µg, about 250 µg to about 550 µg, about 250 µg to about 575 µg, about 250 µg to about 600 µg, about 250 µg to about 625 µg, about 250 µg to about 650 µg, about 250 µg to about 675 µg, about 250 µg to about 700 µg, about 250 µg to about 725 µg, about 250 µg to about 750 µg, about 250 µg to about 775 µg, about 250 µg to about 800 µg, about 250 µg to about 825 µg, about 250 µg to about 850 µg, about 250 µg to about 875 µg, about 250 µg to about 900 µg, about 250 µg to about 925 µg, about 250 µg to about 950 µg, about 250 µg to about 975 µg, about 250 µg to about 1,000 µg, about 300 µg to about 325 µg, about 300 µg to about 350 µg, about 300 µg to about 375 µg, about 300 µg to about 400 µg, about 300 µg to about 425 µg, about 300 µg to about 450 µg, about 300 µg to about 475 µg, about 300 µg to about 500 µg, about 300 µg to about 525 µg, about 300 µg to about 550 µg, about 300 µg to about 575 µg, about 300 µg to about 600 µg, about 300 µg to about 625 µg, about 300 µg to about 650 µg, about 300 µg to about 675 µg, about 300 µg to about 700 µg, about 300 µg to about 725 µg, about 300 µg to about 750 µg, about 300 µg to about 775 µg, about 300 µg to about 800 µg, about 300 µg to about 825 µg, about 300 µg to about 850 µg, about 300 µg to about 875 µg, about 300 µg to about 900 µg, about 300 µg to about 925 µg, about 300 µg to about 950 µg, about 300 µg to about 975 µg, about 300 µg to about 1,000 µg, about 400 µg to about 425 µg, about 400 µg to about 450 µg, about 400 µg to about 475 µg, about 400 µg to about 500 µg, about 400 µg to about 525 µg, about 400 µg to about 550 µg, about 400 µg to about 575 µg, about 400 µg to about 600 µg, about 400 µg to about 625 µg, about 400 µg to about 650 µg, about 400 µg to about 675 µg, about 400 µg to about 700 µg, about 400 µg to about 725 µg, about 400 µg to about 750 µg, about 400 µg to about 775 µg, about 400 µg to about 800 µg, about 400 µg to about 825 µg, about 400 µg to about 850 µg, about 400 µg to about 875 µg, about 400 µg to about 900 µg, about 400 µg to about 925 µg, about 400 µg to about 950 µg, about 400 µg to about 975 µg, about 400 µg to about 1,000 µg, about 500 µg to about 525 µg, about 500 µg to about 550 µg, about 500 µg to about 575 µg, about 500 µg to about 600 µg, about 500 µg to about 625 µg, about 500 µg to about 650 µg, about 500 µg to about 675 µg, about 500 µg to about 700 µg, about 500 µg to about 725 µg, about 500 µg to about 750 µg, about 500 µg to about 775 µg, about 500 µg to about 800 µg, about 500 µg to about 825 µg, about 500 µg to about 850 µg, about 500 µg to about 875 µg, about 500 µg to about 900 µg, about 500 µg to about 925 µg, about 500 µg to about 950 µg, about 500 µg to about 975 µg, about 500 µg to about 1,000 µg, about 600 µg to about 625 µg, about 600 µg to about 650 µg, about 600 µg to about 675 µg, about 600 µg to about 700 µg, about 600 µg to about 725 µg, about 600 µg to about 750 µg, about 600 µg to about 775 µg, about 600 µg to about 800 µg, about 600 µg to about 825 µg, about 600 µg to about 850 µg, about 600 µg to about 875 µg, about 600 µg to about 900 µg, about 600 µg to about 925 µg, about 600 µg to about 950 µg, about 600 µg to about 975 µg, about 600 µg to about 1,000 µg, about 700 µg to about 725 µg, about 700 µg to about 750 µg, about 700 µg to about 775 µg, about 700 µg to about 800 µg, about 700 µg to about 825 µg, about 700 µg to about 850 µg, about 700 µg to about 875 µg, about 700 µg to about 900 µg, about 700 µg to about 925 µg, about 700 µg to about 950 µg, about 700 µg to about 975 µg, about 700 µg to about 1,000 µg, about 800 µg to about 825 µg, about 800 µg to about 850 µg, about 800 µg to about 875 µg, about 800 µg to about 900 µg, about 800 µg to about 925 µg, about 800 µg to about 950 µg, about 800 µg to about 975 µg, or about 800 µg to about 1,000 µg.

102. The pharmaceutical composition of embodiment 99, wherein the one or more compounds are in an amount of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, 260 mg, about 270 mg, about 280 mg, about 290 mg, about 300 mg, about 310 mg, about 320 mg, about 330 mg, about 340 mg, about 350 mg, 360 mg, about 370 mg, about 380 mg, about 390 mg, about 400 mg, about 410 mg, about 420 mg, about 430 mg, about 440 mg, about 450 mg, 460 mg, about 470 mg, about 480 mg, about 490 mg, about 500 mg, about 510 mg, about 520 mg, about 530 mg, about 540 mg, about 550 mg, 560 mg, about 570 mg, about 580 mg, about 590 mg, about 600 mg, about 610 mg, about 620 mg, about 630 mg, about 640 mg, about 650 mg, 660 mg, about 670 mg, about 680 mg, about 690 mg, about 700 mg, about 710 mg, about 720 mg, about 730 mg, about 740 mg, about 750 mg, 760 mg, about 770 mg, about 780 mg, about 790 mg, about 800 mg, about 810 mg, about 820 mg, about 830 mg, about 840 mg, about 850 mg, 860 mg, about 870 mg, about 880 mg, about 890 mg, about 900 mg, about 910 mg, about 920 mg, about 930 mg, about 940 mg, about 950 mg, 960 mg, about 970 mg, about 980 mg, about 990 mg, or about 1,000 mg, or in an amount of at least 1 mg, at least 2 mg, at least 3 mg, at least 4 mg, at least 5 mg, at least 6 mg, at least 7 mg, at least 8 mg, at least 9 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, at least 100 mg, at least 110 mg, at least 120 mg, at least 130 mg, at least 140 mg, at least 150 mg, at least 160 mg, at least 170 mg, at least 180 mg, at least 190 mg, at least 200 mg, at least 210 mg, at least 220 mg, at least 230 mg, at least 240 mg, at least 250 mg, 260 mg, at least 270 mg, at least 280 mg, at least 290 mg, at least 300 mg, at least 310 mg, at least 320 mg, at least 330 mg, at least 340 mg, at least 350 mg, 360 mg, at least 370 mg, at least 380 mg, at least 390 mg, at least 400 mg, at least 410 mg, at least 420 mg, at least 430 mg, at least 440 mg, at least 450 mg, 460 mg, at least 470 mg, at least 480 mg, at least 490 mg, at least 500 mg, at least 510 mg, at least 520 mg, at least 530 mg, at least 540 mg, at least 550 mg, 560 mg, at least 570 mg, at least 580 mg, at least 590 mg, at least 600 mg, at least 610 mg, at least 620 mg, at least 630 mg, at least 640 mg, at least 650 mg, 660 mg, at least 670 mg, at least 680 mg, at least 690 mg, at least 700 mg, at least 710 mg, at least 720 mg, at least 730 mg, at least 740 mg, at least 750 mg, 760 mg, at least 770 mg, at least 780 mg, at least 790 mg, at least 800 mg, at least 810 mg, at least 820 mg, at least 830 mg, at least 840 mg, at least 850 mg, 860 mg, at least 870 mg, at least 880 mg, at least 890 mg, at least 900 mg, at least 910 mg, at least 920 mg, at least 930 mg, at least 940 mg, at least 950 mg, 960 mg, at least 970 mg, at least 980 mg, at least 990 mg, or at least 1,000 mg, or in an amount of at most 1 mg, at most 2 mg, at most 3 mg, at most 4 mg, at most 5 mg, at most 6 mg, at most 7 mg, at most 8 mg, at most 9 mg, at most 10 mg, at most 15 mg, at most 20 mg, at most 25 mg, at most 30 mg, at most 35 mg, at most 40 mg, at most 45 mg, at most 50 mg, at most 55 mg, at most 60 mg, at most 65 mg, at most 70 mg, at most 75 mg, at most 80 mg, at most 85 mg, at most 90 mg, at most 95 mg, at most 100 mg, at most 110 mg, at most 120 mg, at most 130 mg, at most 140 mg, at most 150 mg, at most 160 mg, at most 170 mg, at most 180 mg, at most 190 mg, at most 200 mg, at most 210 mg, at most 220 mg, at most 230 mg, at most 240 mg, at most 250 mg, 260 mg, at most 270 mg, at most 280 mg, at most 290 mg, at most 300 mg, at most 310 mg, at most 320 mg, at most 330 mg, at most 340 mg, at most 350 mg, 360 mg, at most 370 mg, at most 380 mg, at most 390 mg, at most 400 mg, at most 410 mg, at most 420 mg, at most 430 mg, at most 440 mg, at most 450 mg, 460 mg, at most 470 mg, at most 480 mg, at most 490 mg, at most 500 mg, at most 510 mg, at most 520 mg, at most 530 mg, at most 540 mg, at most 550 mg, 560 mg, at most 570 mg, at most 580 mg, at most 590 mg, at most 600 mg, at most 610 mg, at most 620 mg, at most 630 mg, at most 640 mg, at most 650 mg, 660 mg, at most 670 mg, at most 680 mg, at most 690 mg, at most 700 mg, at most 710 mg, at most 720 mg, at most 730 mg, at most 740 mg, at most 750 mg, 760 mg, at most 770 mg, at most 780 mg, at most 790 mg, at most 800 mg, at most 810 mg, at most 820 mg, at most 830 mg, at most 840 mg, at most 850 mg, 860 mg, at most 870 mg, at most 880 mg, at most 890 mg, at most 900 mg, at most 910 mg, at most 920 mg, at most 930 mg, at most 940 mg, at most 950 mg, 960 mg, at most 970 mg, at most 980 mg, at most 990 mg, or at most 1,000 mg.

103. The pharmaceutical composition of embodiment 99, wherein the one or more compounds are in an amount of about 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, about 1 mg to about 90 mg, about 1 mg to about 100 mg, about 1 mg to about 110 mg, about 1 mg to about 120 mg, about 1 mg to about 130 mg, about 1 mg to about 140 mg, about 1 mg to about 150 mg, about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, about 5 mg to about 90 mg, about 5 mg to about 100 mg, about 5 mg to about 110 mg, about 5 mg to about 120 mg, about 5 mg to about 130 mg, about 5 mg to about 140 mg, about 5 mg to about 150 mg, about 10 mg to about 20 mg, about 10 mg to about 30 mg, about 10 mg to about 40 mg, about 10 mg to about 50 mg, about 10 mg to about 60 mg, about 10 mg to about 70 mg, about 10 mg to about 80 mg, about 10 mg to about 90 mg, about 10 mg to about 100 mg, about 10 mg to about 110 mg, about 10 mg to about 120 mg, about 10 mg to about 130 mg, about 10 mg to about 140 mg, about 10 mg to about 150 mg, about 10 mg to about 175 mg, about 10 mg to about 200 mg, about 10 mg to about 225 mg, about 10 mg to about 250 mg, about 25 mg to about 50 mg, about 25 mg to about 75 mg, about 25 mg to about 100 mg, about 25 mg to about 125 mg, about 25 mg to about 150 mg, about 25 mg to about 175 mg, about 25 mg to about 200 mg, about 25 mg to about 225 mg, about 25 mg to about 250 mg, about 50 mg to about 75 mg, about 50 mg to about 100 mg, about 50 mg to about 125 mg, about 50 mg to about 150 mg, about 50 mg to about 175 mg, about 50 mg to about 200 mg, about 50 mg to about 225 mg, about 50 mg to about 250 mg, about 75 mg to about 100 mg, about 75 mg to about 125 mg, about 75 mg to about 150 mg, about 75 mg to about 175 mg, about 75 mg to about 200 mg, about 75 mg to about 225 mg, about 75 mg to about 250 mg, about 100 mg to about 125 mg, about 100 mg to about 150 mg, about 100 mg to about 175 mg, about 100 mg to about 200 mg, about 100 mg to about 225 mg, about 100 mg to about 250 mg, about 100 mg to about 275 mg, about 100 mg to about 300 mg, about 100 mg to about 325 mg, about 100 mg to about 350 mg, about 100 mg to about 375 mg, about 100 mg to about 400 mg, about 100 mg to about 425 mg, about 100 mg to about 450 mg, about 100 mg to about 475 mg, about 100 mg to about 500 mg, about 100 mg to about 525 mg, about 100 mg to about 550 mg, about 100 mg to about 575 mg, about 100 mg to about 600 mg, about 125 mg to about 150 mg, about 125 mg to about 175 mg, about 125 mg to about 200 mg, about 125 mg to about 225 mg, about 125 mg to about 250 mg, about 125 mg to about 275 mg, about 125 mg to about 300 mg, about 125 mg to about 325 mg, about 125 mg to about 350 mg, about 125 mg to about 375 mg, about 125 mg to about 400 mg, about 125 mg to about 425 mg, about 125 mg to about 450 mg, about 125 mg to about 475 mg, about 125 mg to about 500 mg, about 125 mg to about 525 mg, about 125 mg to about 550 mg, about 125 mg to about 575 mg, about 125 mg to about 600 mg, about 150 mg to about 175 mg, about 150 mg to about 200 mg, about 150 mg to about 225 mg, about 150 mg to about 250 mg, about 150 mg to about 275 mg, about 150 mg to about 300 mg, about 150 mg to about 325 mg, about 150 mg to about 350 mg, about 150 mg to about 375 mg, about 150 mg to about 400 mg, about 150 mg to about 425 mg, about 150 mg to about 450 mg, about 150 mg to about 475 mg, about 150 mg to about 500 mg, about 150 mg to about 525 mg, about 150 mg to about 550 mg, about 150 mg to about 575 mg, about 150 mg to about 600 mg, about 200 mg to about 225 mg, about 200 mg to about 250 mg, about 200 mg to about 275 mg, about 200 mg to about 300 mg, about 200 mg to about 325 mg, about 200 mg to about 350 mg, about 200 mg to about 375 mg, about 200 mg to about 400 mg, about 200 mg to about 425 mg, about 200 mg to about 450 mg, about 200 mg to about 475 mg, about 200 mg to about 500 mg, about 200 mg to about 525 mg, about 200 mg to about 550 mg, about 200 mg to about 575 mg, about 200 mg to about 600 mg, about 200 mg to about 625 mg, about 200 mg to about 650 mg, about 200 mg to about 675 mg, about 200 mg to about 700 mg, about 200 mg to about 725 mg, about 200 mg to about 750 mg, about 200 mg to about 775 mg, about 200 mg to about 800 mg, about 200 mg to about 825 mg, about 200 mg to about 850 mg, about 200 mg to about 875 mg, about 200 mg to about 900 mg, about 200 mg to about 925 mg, about 200 mg to about 950 mg, about 200 mg to about 975 mg, about 200 mg to about 1,000 mg, about 250 mg to about 275 mg, about 250 mg to about 300 mg, about 250 mg to about 325 mg, about 250 mg to about 350 mg, about 250 mg to about 375 mg, about 250 mg to about 400 mg, about 250 mg to about 425 mg, about 250 mg to about 450 mg, about 250 mg to about 475 mg, about 250 mg to about 500 mg, about 250 mg to about 525 mg, about 250 mg to about 550 mg, about 250 mg to about 575 mg, about 250 mg to about 600 mg, about 250 mg to about 625 mg, about 250 mg to about 650 mg, about 250 mg to about 675 mg, about 250 mg to about 700 mg, about 250 mg to about 725 mg, about 250 mg to about 750 mg, about 250 mg to about 775 mg, about 250 mg to about 800 mg, about 250 mg to about 825 mg, about 250 mg to about 850 mg, about 250 mg to about 875 mg, about 250 mg to about 900 mg, about 250 mg to about 925 mg, about 250 mg to about 950 mg, about 250 mg to about 975 mg, about 250 mg to about 1,000 mg, about 300 mg to about 325 mg, about 300 mg to about 350 mg, about 300 mg to about 375 mg, about 300 mg to about 400 mg, about 300 mg to about 425 mg, about 300 mg to about 450 mg, about 300 mg to about 475 mg, about 300 mg to about 500 mg, about 300 mg to about 525 mg, about 300 mg to about 550 mg, about 300 mg to about 575 mg, about 300 mg to about 600 mg, about 300 mg to about 625 mg, about 300 mg to about 650 mg, about 300 mg to about 675 mg, about 300 mg to about 700 mg, about 300 mg to about 725 mg, about 300 mg to about 750 mg, about 300 mg to about 775 mg, about 300 mg to about 800 mg, about 300 mg to about 825 mg, about 300 mg to about 850 mg, about 300 mg to about 875 mg, about 300 mg to about 900 mg, about 300 mg to about 925 mg, about 300 mg to about 950 mg, about 300 mg to about 975 mg, about 300 mg to about 1,000 mg, about 400 mg to about 425 mg, about 400 mg to about 450 mg, about 400 mg to about 475 mg, about 400 mg to about 500 mg, about 400 mg to about 525 mg, about 400 mg to about 550 mg, about 400 mg to about 575 mg, about 400 mg to about 600 mg, about 400 mg to about 625 mg, about 400 mg to about 650 mg, about 400 mg to about 675 mg, about 400 mg to about 700 mg, about 400 mg to about 725 mg, about 400 mg to about 750 mg, about 400 mg to about 775 mg, about 400 mg to about 800 mg, about 400 mg to about 825 mg, about 400 mg to about 850 mg, about 400 mg to about 875 mg, about 400 mg to about 900 mg, about 400 mg to about 925 mg, about 400 mg to about 950 mg, about 400 mg to about 975 mg, about 400 mg to about 1,000 mg, about 500 mg to about 525 mg, about 500 mg to about 550 mg, about 500 mg to about 575 mg, about 500 mg to about 600 mg, about 500 mg to about 625 mg, about 500 mg to about 650 mg, about 500 mg to about 675 mg, about 500 mg to about 700 mg, about 500 mg to about 725 mg, about 500 mg to about 750 mg, about 500 mg to about 775 mg, about 500 mg to about 800 mg, about 500 mg to about 825 mg, about 500 mg to about 850 mg, about 500 mg to about 875 mg, about 500 mg to about 900 mg, about 500 mg to about 925 mg, about 500 mg to about 950 mg, about 500 mg to about 975 mg, about 500 mg to about 1,000 mg, about 600 mg to about 625 mg, about 600 mg to about 650 mg, about 600 mg to about 675 mg, about 600 mg to about 700 mg, about 600 mg to about 725 mg, about 600 mg to about 750 mg, about 600 mg to about 775 mg, about 600 mg to about 800 mg, about 600 mg to about 825 mg, about 600 mg to about 850 mg, about 600 mg to about 875 mg, about 600 mg to about 900 mg, about 600 mg to about 925 mg, about 600 mg to about 950 mg, about 600 mg to about 975 mg, about 600 mg to about 1,000 mg, about 700 mg to about 725 mg, about 700 mg to about 750 mg, about 700 mg to about 775 mg, about 700 mg to about 800 mg, about 700 mg to about 825 mg, about 700 mg to about 850 mg, about 700 mg to about 875 mg, about 700 mg to about 900 mg, about 700 mg to about 925 mg, about 700 mg to about 950 mg, about 700 mg to about 975 mg, about 700 mg to about 1,000 mg, about 800 mg to about 825 mg, about 800 mg to about 850 mg, about 800 mg to about 875 mg, about 800 mg to about 900 mg, about 800 mg to about 925 mg, about 800 mg to about 950 mg, about 800 mg to about 975 mg, or about 800 mg to about 1,000 mg.

104. The pharmaceutical composition of any one of embodiments 99-103, wherein the one or more compounds are in an amount of 0.01%, 0.025%, 0.05%, 0.075%, 0.1%, 0.2%, 0.25%, 0.3%, 0.4%, 0.5%, 0.6%, 0.7%, 0.75%, 0.8%, 0.9%, 1%, 2%, 3%, 4%, 5%, 6%, 7%, 8%. 9%, 10%, 15%, 20%, 25%, 30%, 35%, 40%, 45% or 50% by weight of the composition, or at least 0.01%, at least 0.025%, at least 0.05%, at least 0.075%, at least 0.1%, at least 0.25%, at least 0.5%, at least 0.75%, at least 1%, at least 2%, at least 3%, at least 4%, at least 5%, at least 6%, at least 7%, at least 8%, at least 9%, least 10%, least 15%, least 20%, least 25%, least 30%, least 35%, least 40%, at least 45%, or at least 50% by weight of the composition, or at most 0.01%, at most 0.025%, at most 0.05%, at most 0.075%, at most 0.1%, at most 0.25%, at most 0.5%, at most 0.75%, at most 1%, at most 2%, at most 3%, at most 4%, at most 5%, at most 6%, at most 7%, at most 8%, at most 9%, at most 10%, at most 15%, at most 20%, at most 25%, at most 30%, at most 35%, at most 40%, at most 45%, or at most 50% by weight of the composition.

105. The pharmaceutical composition of any one of embodiments 99-103, wherein the one or more compounds are in an amount of 0.01% to about 0.05%, 0.01% to about 0.075%, 0.01% to about 0.1%, about 0.1% to about 0.5%, about 0.1% to about 0.75%, about 0.1% to about 1%, about 0.1% to about 2%, about 0.1% to about 3%, about 0.1% to about 4%, about 0.1% to about 5%, about 0.1% to about 6%, about 0.1% to about 7%, about 0.1% to about 8%, about 0.1% to about 9%, about 0.1% to about 10%, about 0.1% to about 15%, about 0.1% to about 20%, about 0.1% to about 25%, about 0.1% to about 30%, about 0.1% to about 35%, about 0.1% to about 40%, about 0.25% to about 0.5%, about 0.25% to about 0.75%, about 0.25% to about 1%, about 0.25% to about 2%, about 0.25% to about 3%, about 0.25% to about 4%, about 0.25% to about 5%, about 0.25% to about 6%, about 0.25% to about 7%, about 0.25% to about 8%, about 0.25% to about 9%, about 0.25% to about 10%, about 0.25% to about 15%, about 0.25% to about 20%, about 0.25% to about 25%, about 0.25% to about 30%, about 0.25% to about 35%, about 0.25% to about 40%, about 0.5% to about 0.75%, about 0.5% to about 1%, about 0.5% to about 2%, about 0.5% to about 3%, about 0.5% to about 4%, about 0.5% to about 5%, about 0.5% to about 6%, about 0.5% to about 7%, about 0.5% to about 8%, about 0.5% to about 9%, about 0.5% to about 10%, about 0.5% to about 15%, about 0.5% to about 20%, about 0.5% to about 25%, about 0.5% to about 30%, about 0.5% to about 35%, about 0.5% to about 40%, about 0.75% to about 1%, about 0.75% to about 2%, about 0.75% to about 3%, about 0.75% to about 4%, about 0.75% to about 5%, about 0.75% to about 6%, about 0.75% to about 7%, about 0.75% to about 8%, about 0.75% to about 9%, about 0.75% to about 10%, about 0.75% to about 15%, about 0.75% to about 20%, about 0.75% to about 25%, about 0.75% to about 30%, about 0.75% to about 35%, about 0.75% to about 40%, about 1% to about 2%, about 1% to about 3%, about 1% to about 4%, about 1% to about 5%, about 1% to about 6%, about 1% to about 7%, about 1% to about 8%, about 1% to about 9%, about 1% to about 10%, about 1% to about 15%, about 1% to about 20%, about 1% to about 25%, about 1% to about 30%, about 1% to about 35%, about 1% to about 40%, about 2% to about 3%, about 2% to about 4%, about 2% to about 5%, about 2% to about 6%, about 2% to about 7%, about 2% to about 8%, about 2% to about 9%, about 2% to about 10%, about 2% to about 15%, about 2% to about 20%, about 2% to about 25%, about 2% to about 30%, about 2% to about 35%, about 2% to about 40%, about 3% to about 4%, about 3% to about 5%, about 3% to about 6%, about 3% to about 7%, about 3% to about 8%, about 3% to about 9%, about 3% to about 10%, about 3% to about 15%, about 3% to about 20%, about 3% to about 25%, about 3% to about 30%, about 3% to about 35%, about 3% to about 40%, about 4% to about 5%, about 4% to about 6%, about 4% to about 7%, about 4% to about 8%, about 4% to about 9%, about 4% to about 10%, about 4% to about 15%, about 4% to about 20%, about 4% to about 25%, about 4% to about 30%, about 4% to about 35%, about 4% to about 40%, about 5% to about 6%, about 5% to about 7%, about 5% to about 8%, about 5% to about 9%, about 5% to about 10%, about 5% to about 15%, about 5% to about 20%, about 5% to about 25%, about 5% to about 30%, about 5% to about 35%, about 5% to about 40%, about 6% to about 7%, about 6% to about 8%, about 6% to about 9%, about 6% to about 10%, about 6% to about 15%, about 6% to about 20%, about 6% to about 25%, about 6% to about 30%, about 6% to about 35%, about 6% to about 40%, about 7% to about 8%, about 7% to about 9%, about 7% to about 10%, about 7% to about 15%, about 7% to about 20%, about 7% to about 25%, about 7% to about 30%, about 7% to about 35%, about 7% to about 40%, about 8% to about 9%, about 8% to about 10%, about 8% to about 15%, about 8% to about 20%, about 8% to about 25%, about 8% to about 30%, about 8% to about 35%, about 8% to about 40%, about 9% to about 10%, about 9% to about 15%, about 9% to about 20%, about 9% to about 25%, about 9% to about 30%, about 9% to about 35%, about 9% to about 40%, about 10% to about 15%, about 10% to about 20%, about 10% to about 25%, about 10% to about 30%, about 10% to about 35%, about 10% to about 40%, about 10% to about 45%, about 10% to about 50%, about 15% to about 20%, about 15% to about 25%, about 15% to about 30%, about 15% to about 35%, about 15% to about 40%, about 15% to about 45%, about 15% to about 50%, about 20% to about 25%, about 20% to about 30%, about 20% to about 35%, about 20% to about 40%, about 20% to about 45%, about 20% to about 50%, about 25% to about 30%, about 25% to about 35%, about 25% to about 40%, about 25% to about 45%, about 30% to about 25%, about 30% to about 35%, about 30% to about 40%, about 30% to about 45%, about 30% to about 50%, about 35% to about 40%, about 35% to about 45%, about 35% to about 50%, about 40% to about 45%, about 40% to about 50%, or about 45% to about 50%, by weight of the composition.

106. The pharmaceutical composition of any one of embodiments 99-105, further comprising one or more pharmaceutically acceptable carriers.

107. The pharmaceutical composition of embodiment 106, wherein the one or more pharmaceutically acceptable carriers are in an amount of at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98% or at least 99% by weight of the composition, or at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98% or at most 99% by weight of the composition, or about 25% to about 50%, about 25% to about 75%, about 25% to about 90%, about 25% to about 95%, about 25% to about 96%, about 25% to about 97%, about 25% to about 98%, about 25% to about 99%, about 50% to about 75%, about 50% to about 90%, about 50% to about 95%, about 50% to about 96%, about 50% to about 97%, about 50% to about 98%, about 50% to about 99%, about 75% to about 80%, about 75% to about 85%, about 75% to about 90%, about 75% to about 95%, about 75% to about 96%, about 75% to about 97%, about 75% to about 98%, about 75% to about 99%, about 80% to about 85%, about 80% to about 90%, about 80% to about 95%, about 80% to about 96%, about 80% to about 97%, about 80% to about 98%, about 80% to about 99%, about 85% to about 90%, about 85% to about 95%, about 85% to about 96%, about 85% to about 97%, about 85% to about 98%, about 85% to about 99%, about 90% to about 95%, about 90% to about 96%, about 90% to about 97%, about 90% to about 98%, about 90% to about 99%, or about 95% to about 99%, by weight of the composition.

108. The pharmaceutical composition of any one of embodiments 99-107, further comprising one or more pharmaceutically acceptable components.

109. The pharmaceutical composition of embodiment 108, wherein the one or more pharmaceutically acceptable components include one or more buffers, one or more preservatives, one or more tonicity adjusters, one or more salts, one or more antioxidants, one or more osmolality adjusting agents, one or more physiological substances, one or more pharmacological substances, one or more bulking agents, one or more viscosity agents, one or more surfactants, one or more emulsifying agents, one or more wetting agents, one or more sweetening or flavoring agents.
110. The pharmaceutical composition of any one of embodiments 99-109, formulated as a topical formulation.
111. The pharmaceutical composition of embodiment 110, wherein the topical formulation is a single-phase formulation or a biphasic formulation.
112. The pharmaceutical composition of embodiment 110, wherein the topical formulation is a liquid composition, a colloidal composition, a semi-solid composition, or a solid composition.
113. The pharmaceutical composition of embodiment 110, wherein the topical formulation is a liquid aerosol, a foam, an emulsion, a gel, a sol, or a solid sol.
114. The pharmaceutical composition of embodiment 110, wherein the topical formulation is a spray, a liquid aerosol, a wash, an aftershave, a perfume, a lotion, a cream, a salve, a waxing composition, a mousse, a shampoo, a conditioner, an ointment, a liniment, a paste, a jelly, a soap, a suspension, or an emollient.
115. A kit comprising a pharmaceutical composition as defined in any one of Clams 99-114.
116. The kit of embodiment 115, further comprising a delivery system.
117. A method of treating hair loss in an individual comprising the step of administering a therapeutically effective amount of a compound as defined in any one of embodiments 1-98 or a pharmaceutical composition as defined in any one of embodiments 99-114 to the individual.
118. A method of treating hair thinning in an individual comprising the step of administering a therapeutically effective amount of a compound as defined in any one of embodiments 1-98 or a pharmaceutical composition as defined in any one of embodiments 99-114 to the individual.
119. A method of treating hair color loss in an individual comprising the step of administering a therapeutically effective amount of a compound as defined in any one of embodiments 1-98 or a pharmaceutical composition as defined in any one of embodiments 99-114 to the individual.
120. A method of treating a condition associated with a degenerative hair follicle disorder in an individual comprising the step of administering a therapeutically effective amount of a compound as defined in any one of embodiments 1-98 or a pharmaceutical composition as defined in any one of embodiments 99-114 to the individual.
121. The method of embodiment 120, wherein the degenerative hair follicle disorder is associated with hair loss, hair thinning, hair color loss, no new hair shaft growth, reduced rate of hair shaft growth, reduced hair shaft diameter (thickness), reduced hair shaft length, reduced hair density, reduced keratinization of the hair shaft, increased fragility, reduced hair pigmentation, reduced hair shaft luster, reduced hair health, reduced time a hair follicle spends in anagen phase, reduced time a hair follicle spends in catagen phase, reduced time a hair follicle spends in telogen phase, premature release of hair shaft from hair follicle, premature initiation of apoptosis in hair follicle, premature conversion of a terminal hair into a vellus hair.
122. The method of embodiment 120, wherein the degenerative hair follicle disorder is associated with a scarring alopecias or a non-scarring alopecia.
123. The method of embodiment 122, wherein the scarring alopecia includes bullous diseases, chemical alopecia, discoid lupus erythematosus, severre folliculitis, lichen planopilaris, dissecting cellulitis, central centrifugal cicatricial alopecia, postmenopausal frontal fibrosing alopecia, a tumor or a skin outgrowth.
124. The method of embodiment 122, wherein the non-scarring alopecia includes anagen effluvium, alopecia adnata, alopecia androgenetica, alopecian AREata, alopecia congenitalis, alopecia *diffusa*, alopecia disseminate, alopecia follicularis, alopecia leprotica, alopecia *marginalis*, alopecia medicamentosa, alopecia mucinosa, alopecia neurotica, alopecia pityrodes, alopecia presenili, alopecia *senilis*, alopecia symptomatica, alopecia syphilitica, alopecia totalis, alopecia toxica, alopecia *triangularis*, alopecia *triangularis* congenitalis, alopecia universalis, folliculitis, olliculitis decalvans, traction alopecia, trichotillomania, telogen effluvium, or inherited disorders of the hair shaft.
125. A method of improving hair appearance in an individual comprising the step of administering a therapeutically effective amount of a compound as defined in any one of embodiments 1-98 or a pharmaceutical composition as defined in any one of embodiments 99-114 to the individual.
126. A method of treating a skin condition in an individual comprising the step of administering a therapeutically effective amount of a compound as defined in any one of embodiments 1-98 or a pharmaceutical composition as defined in any one of embodiments 99-114 to the individual.
127. The method of embodiment 126, wherein the skin condition includes an acne, an excessive sebum production, a post-wound scar formation, or a dermatological issue associated with polycystic ovary disease.
128. A method according to any one of embodiments 117-127, wherein the therapeutically effective amount of a compound is at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day or at most 0.001 mg/kg/day, at most 0.01 mg/kg/day, at most 0.1 mg/kg/day, at most 1.0 mg/kg/day, at most 5.0 mg/kg/day, at most 10 mg/kg/day, at most 15 mg/kg/day, at most 20 mg/kg/day, at most 25 mg/kg/day, at most 30 mg/kg/day, at most 35 mg/kg/day, at most 40 mg/kg/day, at most 45 mg/kg/day, or at most 50 mg/kg/day, or about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of an ARE disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/ day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In still other aspects of this embodiment, an effective amount of an ARE disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, about 0.1 mg/kg/day to about 100 mg/kg/day, about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In yet other aspects of this embodiment, an effective amount of an ARE disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

129. A method according to any one of embodiments 117-127, wherein the therapeutically effective amount of a compound is at least 0.001 mg/day, at least 0.01 mg/day, at least 0.1 mg/day, at least 1.0 mg/day, at least 5.0 mg/day, at least 10 mg/day, at least 15 mg/day, at least 20 mg/day, at least 25 mg/day, at least 30 mg/day, at least 35 mg/day, at least 40 mg/day, at least 45 mg/day, or at least 50 mg/day, or at most 0.001 mg/day, at most 0.01 mg/day, at most 0.1 mg/day, at most 1.0 mg/day, at most 5.0 mg/day, at most 10 mg/day, at most 15 mg/day, at most 20 mg/day, at most 25 mg/day, at most 30 mg/day, at most 35 mg/day, at most 40 mg/day, at most 45 mg/day, or at most 50 mg/day, or about 0.001 mg/day to about 10 mg/day, about 0.001 mg/day to about 15 mg/day, about 0.001 mg/day to about 20 mg/day, about 0.001 mg/day to about 25 mg/day, about 0.001 mg/day to about 30 mg/day, about 0.001 mg/day to about 35 mg/day, about 0.001 mg/day to about 40 mg/day, about 0.001 mg/day to about 45 mg/day, about 0.001 mg/day to about 50 mg/day, about 0.001 mg/day to about 75 mg/day, or about 0.001 mg/day to about 100 mg/day. In yet other aspects of this embodiment, an effective amount of an ARE disclosed herein may be in the range of, e.g., about 0.01 mg/day to about 10 mg/day, about 0.01 mg/day to about 15 mg/day, about 0.01 mg/day to about 20 mg/day, about 0.01 mg/day to about 25 mg/day, about 0.01 mg/day to about 30 mg/day, about 0.01 mg/day to about 35 mg/day, about 0.01 mg/day to about 40 mg/day, about 0.01 mg/day to about 45 mg/day, about 0.01 mg/day to about 50 mg/day, about 0.01 mg/day to about 75 mg/day, or about 0.01 mg/day to about 100 mg/day. In still other aspects of this embodiment, an effective amount of an ARE disclosed herein may be in the range of, e.g., about 0.1 mg/day to about 10 mg/day, about 0.1 mg/day to about 15 mg/day, about 0.1 mg/day to about 20 mg/day, about 0.1 mg/day to about 25 mg/day, about 0.1 mg/day to about 30 mg/day, about 0.1 mg/day to about 35 mg/day, about 0.1 mg/day to about 40 mg/day, about 0.1 mg/day to about 45 mg/day, about 0.1 mg/day to about 50 mg/day, about 0.1 mg/day to about 75 mg/day, about 0.1 mg/day to about 100 mg/day, about 1 mg/day to about 10 mg/day, about 1 mg/day to about 15 mg/day, about 1 mg/day to about 20 mg/day, about 1 mg/day to about 25 mg/day, about 1 mg/day to about 30 mg/day, about 1 mg/day to about 35 mg/day, about 1 mg/day to about 40 mg/day, about 1 mg/day to about 45 mg/day, about 1 mg/day to about 50 mg/day, about 1 mg/day to about 75 mg/day, or about 1 mg/day to about 100 mg/day. In yet other aspects of this embodiment, an effective amount of an ARE disclosed herein may be in the range of, e.g., about 5 mg/day to about 10 mg/day, about 5 mg/day to about 15 mg/day, about 5 mg/day to about 20 mg/day, about 5 mg/day to about 25 mg/day, about 5 mg/day to about 30 mg/day, about 5 mg/day to about 35 mg/day, about 5 mg/day to about 40 mg/day, about 5 mg/day to about 45 mg/day, about 5 mg/day to about 50 mg/day, about 5 mg/day to about 75 mg/day, or about 5 mg/day to about 100 mg/day.

130. A method according to any one of embodiments 117-129, wherein administration is a one-time administration or multiple administrations.

131. A method according to any one of embodiments 117-129, wherein the compound or the pharmaceutical composition is administered daily, every other day, every third of day, once a week, multiple times per week, once a month, multiple times per month, once a year or multiple times per year.

132. A method according to any one of embodiments 117-129 or 131, wherein the compound or the pharmaceutical composition is administered multiple times per day.

133. A compound as defined in any one of embodiments 1-98 or a pharmaceutical composition as defined in any one of embodiments 99-114 for use in the treatment of hair loss.

134. A compound as defined in any one of embodiments 1-98 or a pharmaceutical composition as defined in any one of embodiments 99-114 for use in the treatment of hair thinning.

135. A compound as defined in any one of embodiments 1-98 or a pharmaceutical composition as defined in any one of embodiments 99-114 for use in the treatment of hair color loss.

136. A compound as defined in any one of embodiments 1-98 or a pharmaceutical composition as defined in any one of embodiments 99-114 for use in the treatment of a condition associated with a degenerative hair follicle disorder.

137. A compound as defined in any one of embodiments 1-98 or a pharmaceutical composition as defined in any one of embodiments 99-114 for use in improving hair appearance.

138. A compound as defined in any one of embodiments 1-98 or a pharmaceutical composition as defined in any one of embodiments 99-114 for use in the treatment of a skin condition.
139. Use of a compound as defined in any one of embodiments 1-98 or a pharmaceutical composition as defined in any one of embodiments 99-114 for the treatment of hair loss.
140. Use of a compound as defined in any one of embodiments 1-98 or a pharmaceutical composition as defined in any one of embodiments 99-114 for the treatment of hair thinning.
141. Use of a compound as defined in any one of embodiments 1-98 or a pharmaceutical composition as defined in any one of embodiments 99-114 for the treatment of hair color loss.
142. Use of a compound as defined in any one of embodiments 1-98 or a pharmaceutical composition as defined in any one of embodiments 99-114 for the treatment of a condition associated with a degenerative hair follicle disorder.
143. Use of a compound as defined in any one of embodiments 1-98 or a pharmaceutical composition as defined in any one of embodiments 99-114 for improving hair appearance.
144. Use of a compound as defined in any one of embodiments 1-98 or a pharmaceutical composition as defined in any one of embodiments 99-114 for the treatment of a skin condition.
145. Use of a compound as defined in any one of embodiments 1-98 or a pharmaceutical composition as defined in any one of embodiments 99-114 in the manufacture of a medicament for the treatment of hair loss.
146. Use of a compound as defined in any one of embodiments 1-98 or a pharmaceutical composition as defined in any one of embodiments 99-114 in the manufacture of a medicament for the treatment of hair thinning.
147. Use of a compound as defined in any one of embodiments 1-98 or a pharmaceutical composition as defined in any one of embodiments 99-114 in the manufacture of a medicament for the treatment of hair color loss.
148. Use of a compound as defined in any one of embodiments 1-98 or a pharmaceutical composition as defined in any one of embodiments 99-114 in the manufacture of a medicament for the treatment of a condition associated with a degenerative hair follicle disorder.
149. Use of a compound as defined in any one of embodiments 1-98 or a pharmaceutical composition as defined in any one of embodiments 99-114 in the manufacture of a medicament for improving hair appearance.
150. Use of a compound as defined in any one of embodiments 1-98 or a pharmaceutical composition as defined in any one of embodiments 99-114 in the manufacture of a medicament for the treatment of a skin condition.

EXAMPLES

The following non-limiting examples are provided for illustrative purposes only in order to facilitate a more complete understanding of representative embodiments now contemplated. These examples should not be construed to limit any of the embodiments described in the present specification, including those pertaining to the compounds, pharmaceutical compositions, or methods and uses disclosed herein.

Example 1

Preparation of Adamantane Precursor

This example illustrates how to prepare Adamantane precursors for subsequent attachment to a linker molecule disclosed herein.

Scheme 1. Adamantane acetic acid (1.6 g, 8.2 mmol) was dissolved in 20 mL dichloromethane and treated with dimethylformamide (2 drops) and oxalyl chloride (2.1 mL, 24.7 mmol) dropwise. The reaction was stirred at ambient temperature for 18 hours, concentrated in vacuo, and placed under hard vacuum overnight to yield the product as an oil (quant.).

Scheme 1

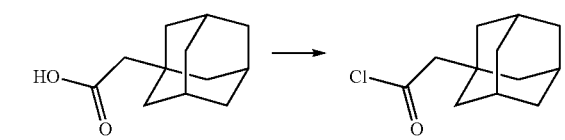

Scheme 2. Adamantane-OH (1.6 g, 8.2 mmol) was dissolved in 20 mL dichloromethane and treated with dimethylformamide (2 drops) and oxalyl chloride (2.1 mL, 24.7 mmol) dropwise. The reaction was stirred at ambient temperature for 18 hours, concentrated in vacuo, and placed under hard vacuum overnight to yield the product as an oil (quant.).

Scheme 2

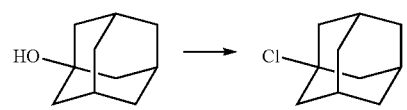

Example 2

Preparation of Adamantane-Linker Conjugate

Scheme 3. Adamantane precursor from scheme 1 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 3, where n is from 0 to 10.

Scheme 3

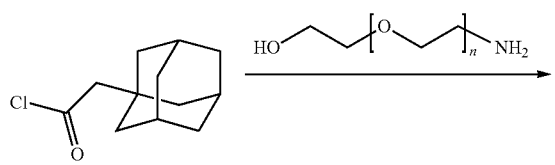

-continued

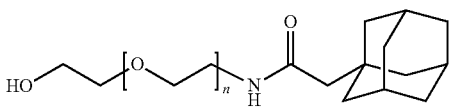

Using Scheme 3, the following Adamantane-linker conjugate compounds are produced:

Compound 1

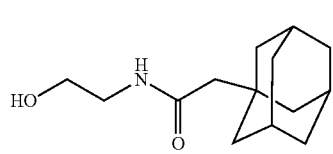

Compound 2

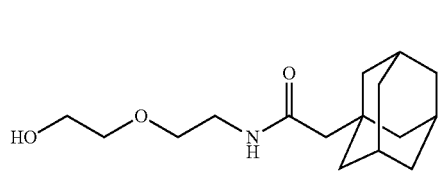

Compound 3

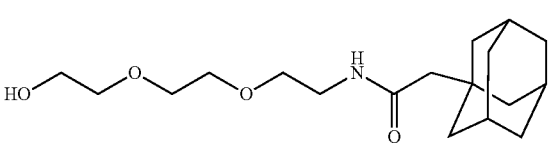

Compound 4

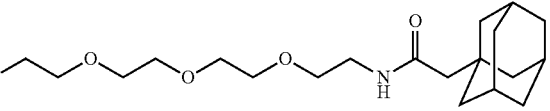

Scheme 4. Adamantane precursor from scheme 1 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 4, where n is from 0 to 10.

Scheme 4

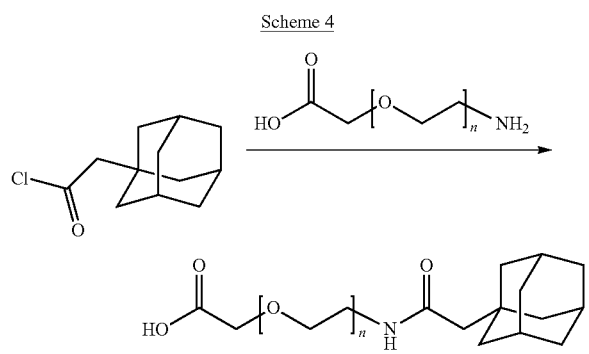

Using Scheme 4, the following Adamantane-linker conjugate compounds are produced:

Compound 5

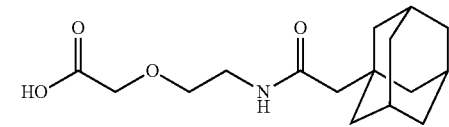

Compound 6

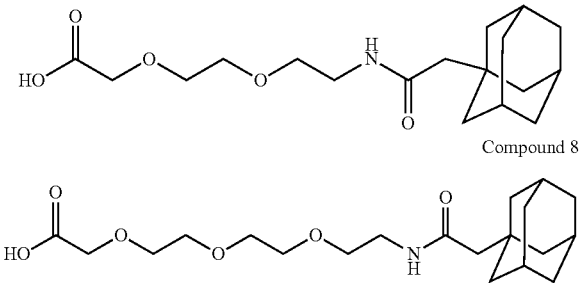

Compound 7

Compound 8

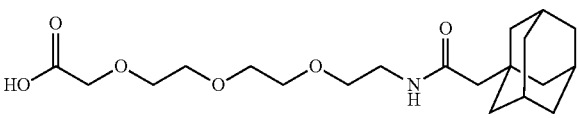

Scheme 5. Adamantane precursor from scheme 2 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 5, where n is from 0 to 10.

Scheme 5

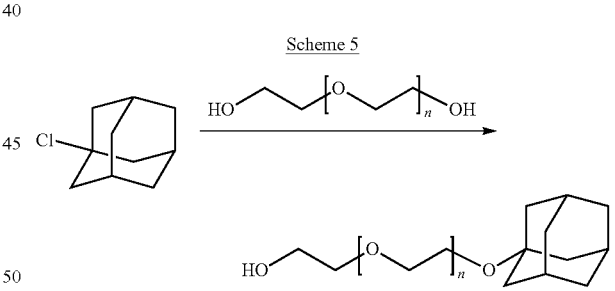

Using Scheme 5, the following Adamantane-linker conjugate compounds are produced:

Compound 9

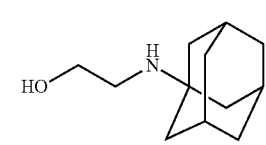

Compound 10

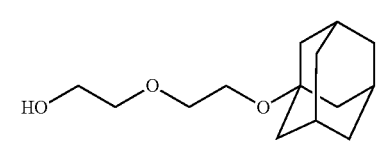

Compound 11

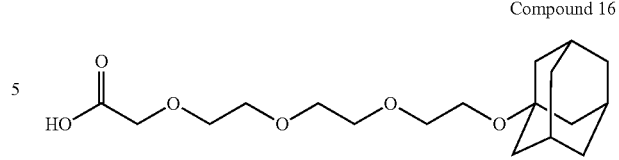

Compound 12

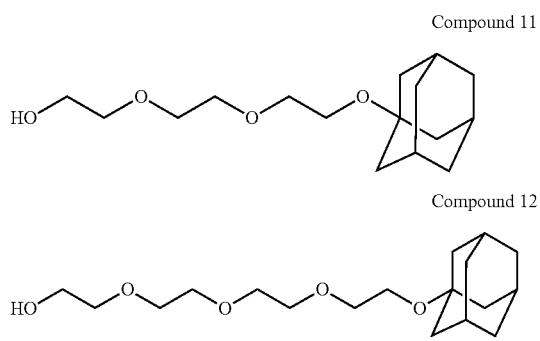

Scheme 6. Adamantane precursor from scheme 2 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 6, where n is from 0 to 10.

Scheme 6

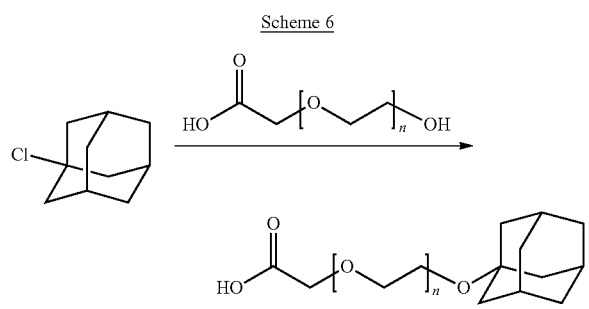

Using Scheme 6, the following Adamantane-linker conjugate compounds are produced:

Compound 13

Compound 14

Compound 15

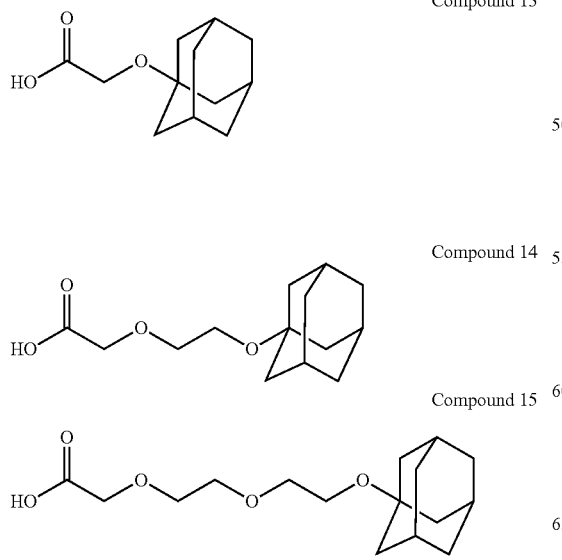

Compound 16

Scheme 7. Adamantane precursor from scheme 2 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 7, where n is from 0 to 10.

Scheme 7

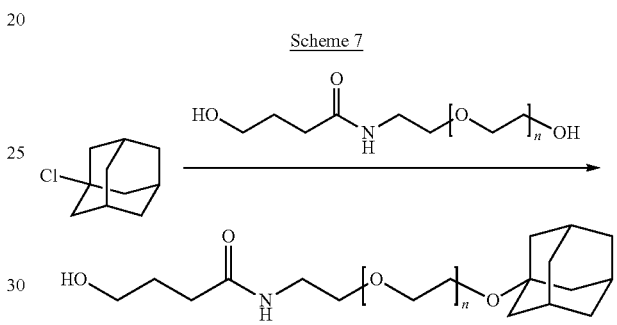

Using Scheme 7, the following Adamantane-linker conjugate compounds are produced:

Compound 17

Compound 18

Compound 19

Compound 20

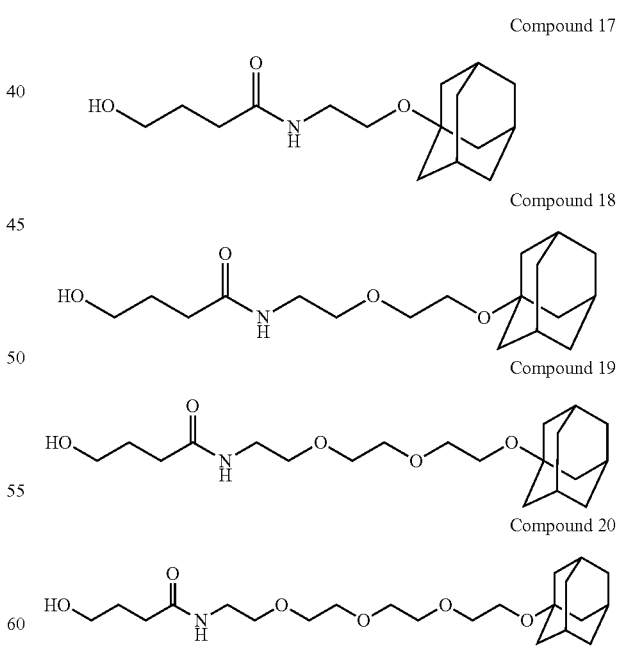

Scheme 8. Adamantane precursor from scheme 2 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 8, where n is from 0 to 10.

Scheme 8

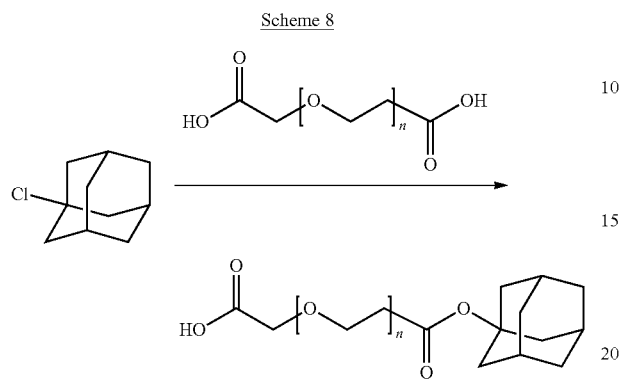

Using Scheme 8, the following Adamantane-linker conjugate compounds are produced:

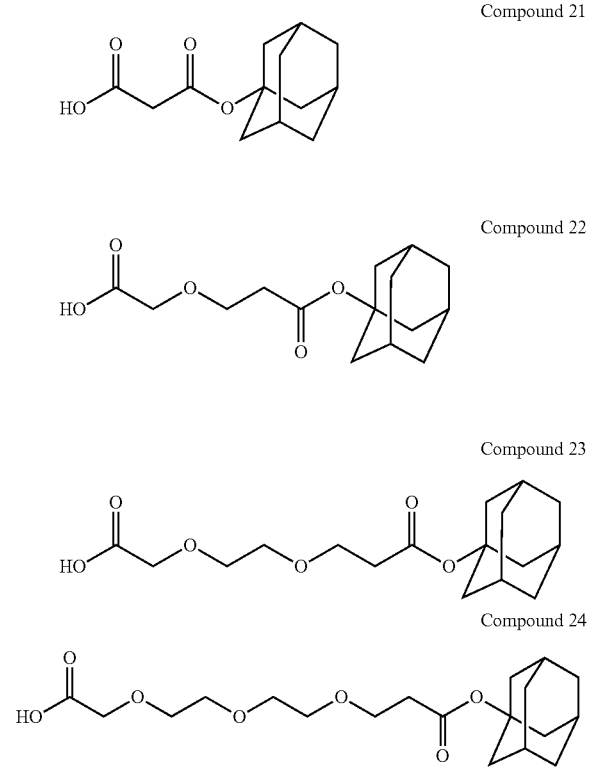

Compound 21

Compound 22

Compound 23

Compound 24

Scheme 9. Adamantane precursor from scheme 2 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 9, where n is from 0 to 10.

Scheme 9

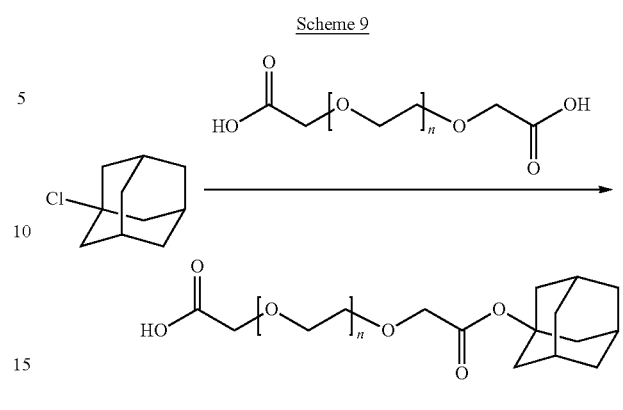

Using Scheme 9, the following Adamantane-linker conjugate compounds were produced:

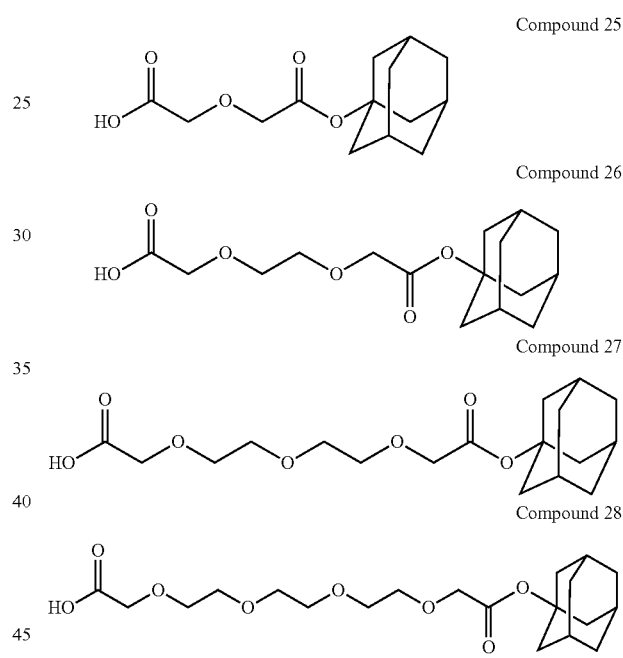

Compound 25

Compound 26

Compound 27

Compound 28

Scheme 10. Adamantane precursor from scheme 2 and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting Adamantane-linker conjugate compounds are shown below in scheme 10, where n is from 0 to 10.

Scheme 10

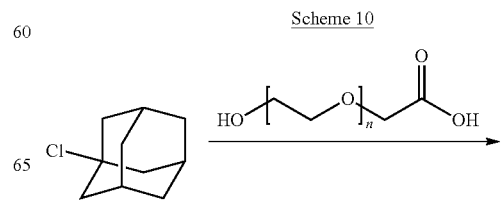

85

-continued

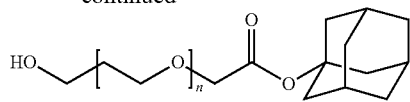

Using Scheme 10, the following Adamantane-linker conjugate compounds were produced:

Compound 29

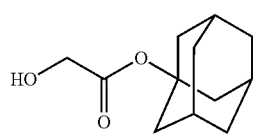

Compound 30

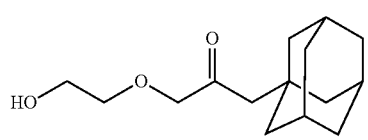

Compound 31

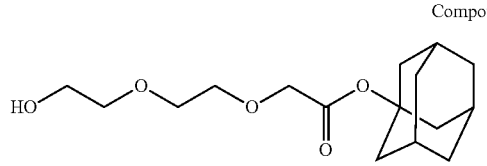

86

-continued

Compound 32

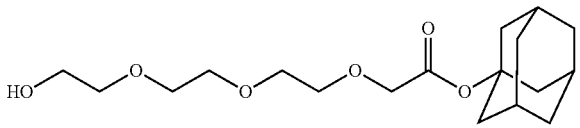

Reaction schemes similar to schemes 3-10 can be performed except that a HIF-1α can be substituted for the Adamantane precursor from scheme 1 or 2.

Example 3

Preparation of HIF-1α-Linker Conjugate

Scheme 11. HIF-1α and linker were suspended in acetonitrile and treated with 3 equivalents of triethanolamine followed by addition of 1 equivalent of acid chloride. The reaction was stirred for 3 hours, diluted with ethyl acetate and washed with 1 N hydrochloric acid and brine, dried over sodium sulfate, concentrated, and placed under high vacuum overnight. The resulting HIF-1α-linker conjugate compounds are shown below in scheme 11, where n is from 0 to 10.

Scheme 11

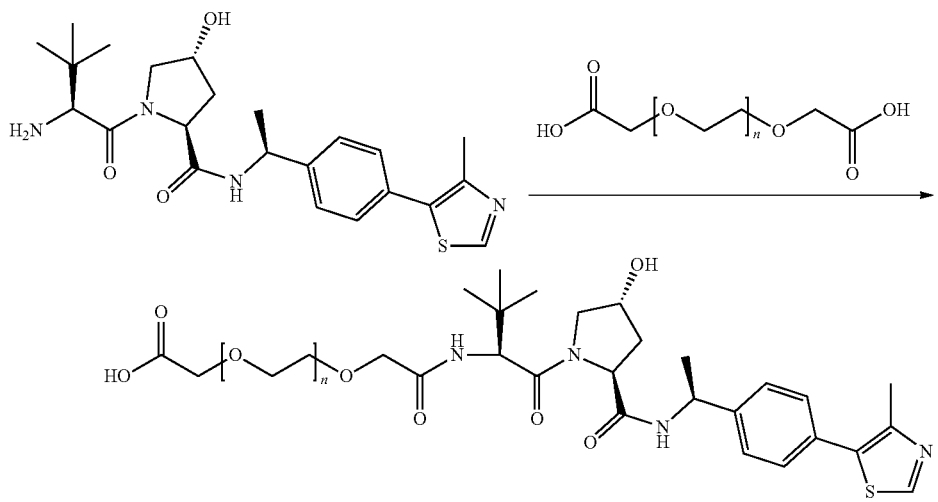

Using Scheme 11, the following HIF-1α-linker conjugate compounds were produced:

Compound 33

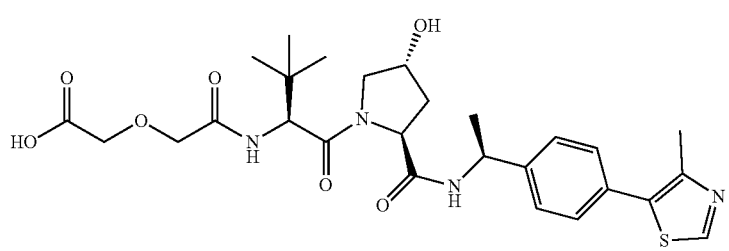

Compound 34

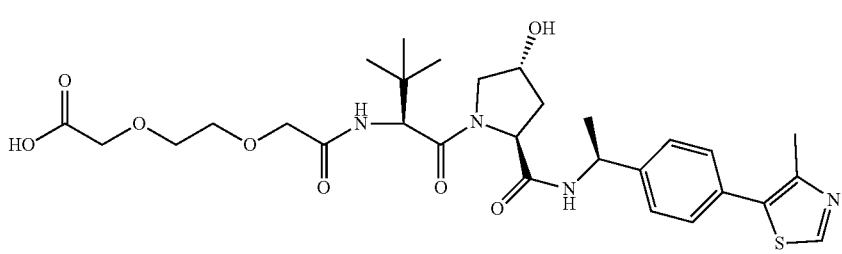

Compound 35

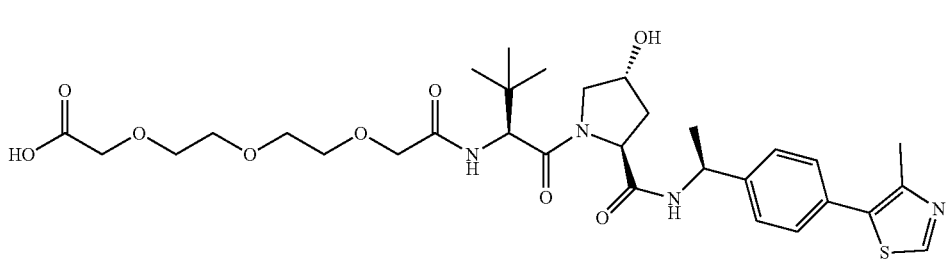

Compound 36

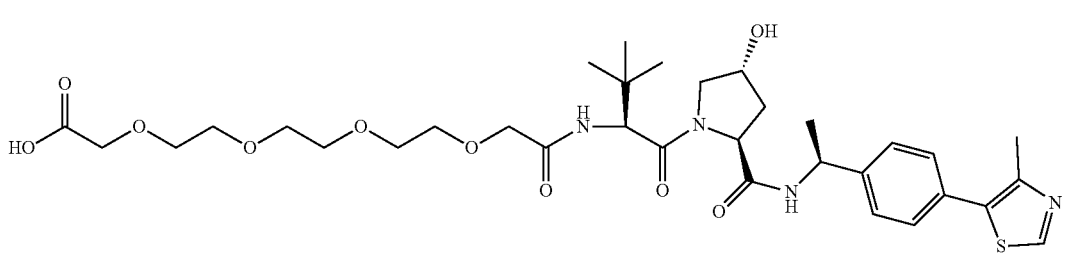

Reaction schemes similar to scheme 11 can be performed except that any one of the other linkers from schemes 3-8 or 10 can be used.

Example 4

Preparation of Androgen Receptor Antagonist Precursor

This example illustrates how to prepare an AR antagonist disclosed herein for subsequent attachment to a linker molecule disclosed herein.

Scheme 12 show the production of a reactive Spironolactone precursor. Methanol (50 mL) was sparged with nitrogen for 15 minutes, treated with spironolactone (5 g, 12 mmol), chilled over ice and treated dropwise with 5.4 M sodium methoxide/methanol (5 mL, 27 mmol). The ice bath was removed and the reaction was stirred for 40 minutes. The reaction was placed in an ice bath and neutralized with acetic acid (1.5 mL) to form a precipitate. More methanol was added and the mixture was sonicated and filtered. A second crop was filtered. The solid was dried under high vacuum overnight and stored in the freezer.

Scheme 12

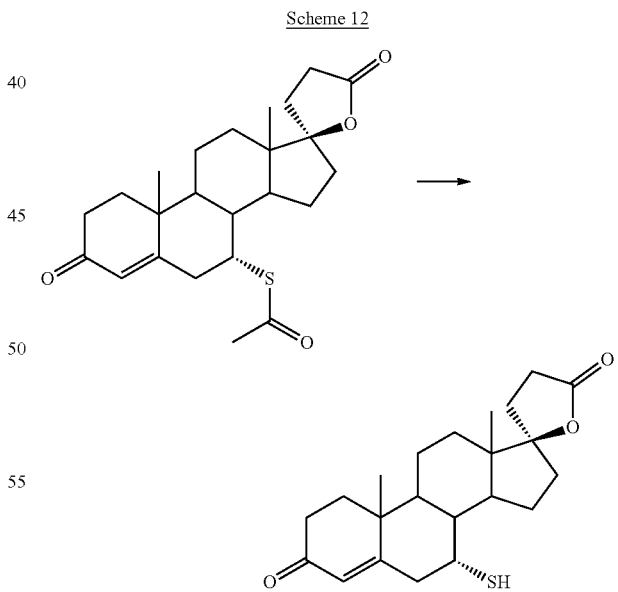

Scheme 13 show the production of a reactive Ketoconazole precursor. Ketoconazole (800 mg) and 20% sodium hydroxide (2 mL) was heated at reflux in methanol (20 mL) overnight. The solution was cooled to ambient temperature and water was added. The resulting precipitate was filtered, washed with water, and dried under high vacuum overnight to give 700 mg.

Scheme 13

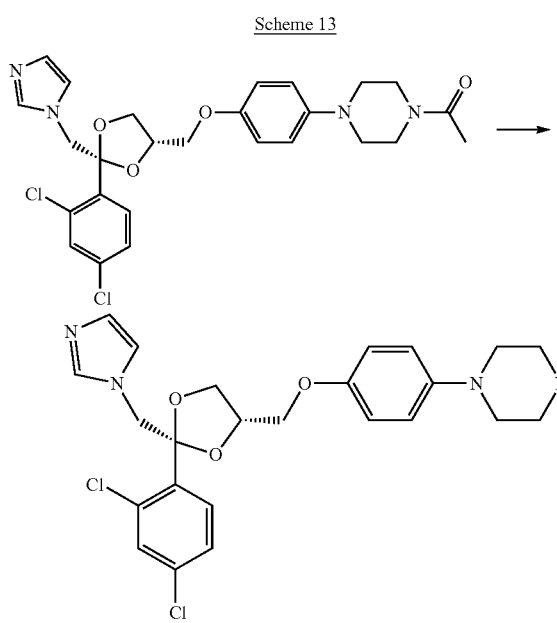

Example 5

Preparation of AR Antagonist-Adamantane-Linker Conjugate

Scheme 14. The reactive Spironolactone precursor (70 mg, 0.18 mg) from scheme 12 and Adamantane precursor from scheme 1 were dissolved in acetonitrile and treated with N,N-Diisopropylethylamine (78 µL, 0.45 mmol). Acid chloride (47 mg, 0.22 mmol) was added and the reaction was stirred for 8 hours. The reaction was diluted with ethyl acetate and washed with 1N hydrochloric acid and brine, dried over sodium sulfate and concentrated. Residue was crystallized from ethyl acetate. The following AR Antagonist-Adamantane-Linker conjugate compound was produced.

Compound 37

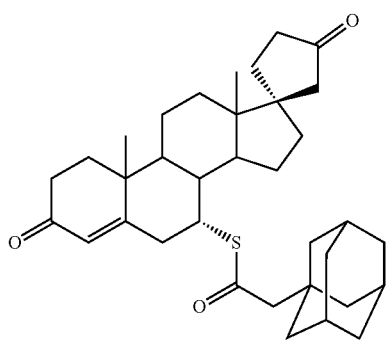

Scheme 15. The reactive Spironolactone precursor (55 mg, 0.15 mmol) from scheme 12 and Adamantane-linker conjugate (55 mg, 0.16 mmol) from scheme 4 were dissolved in dichloromethane (4 mL) and treated with triethanolamine (63 µL, 0.45 mmol) and bis(2-oxo-3-oxazolidinyl) phosphinic chloride (41 mg, 0.16 mmol). Reaction was stirred 2 hours. Minimal product had formed. 4-dimethylaminopyridine was added and stirring was continued overnight. Reaction was diluted with ethyl acetate and washed with citric acid saturated sodium bicarbonate and brine. Purified by Si Gel chromatography using ethyl acetate. The following AR Antagonist-Adamantane-Linker conjugate compounds are produced, where n is from 0 to 10.

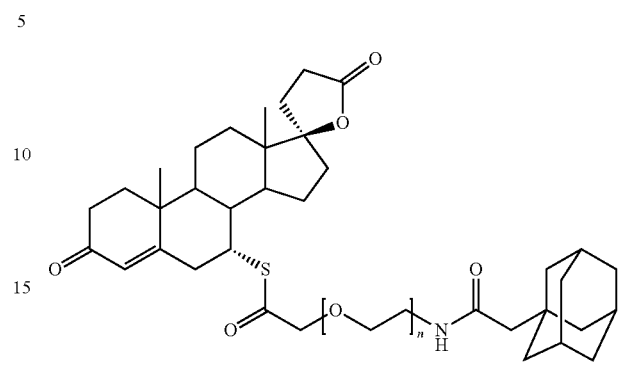

Using Scheme 15, the following AR Antagonist-Adamantane-Linker conjugate compounds were produced:

Compound 38

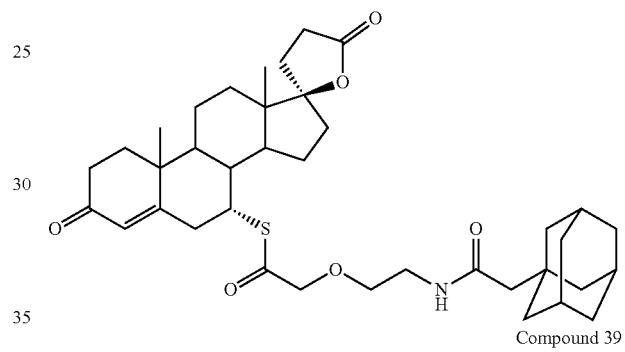

Compound 39

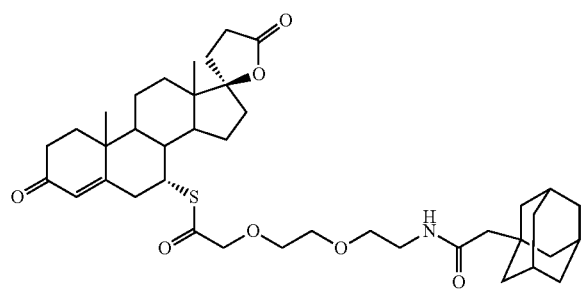

Reaction schemes similar to scheme 15 can be performed except that instead of Adamantane precursor from scheme 4, any one of the other Adamantane precursors from schemes 3 or 5-10 can be used.

Example 6

Preparation of AR Antagonist-Adamantane-Linker Conjugate

Scheme 16. The reactive Ketoconazole precursor (70 mg, 0.18 mg) from scheme 13 and Adamantane precursor from scheme 1 were dissolved in acetonitrile and treated with N,N-Diisopropylethylamine (78 µL, 0.45 mmol). Acid chloride (47 mg, 0.22 mmol) was added and the reaction was stirred for 8 hours. The reaction was diluted with ethyl acetate and washed with 1N hydrochloric acid and brine, dried over sodium sulfate and concentrated. Residue was crystallized from ethyl acetate. The following AR Antagonist-Adamantane-Linker conjugate compound was produced.

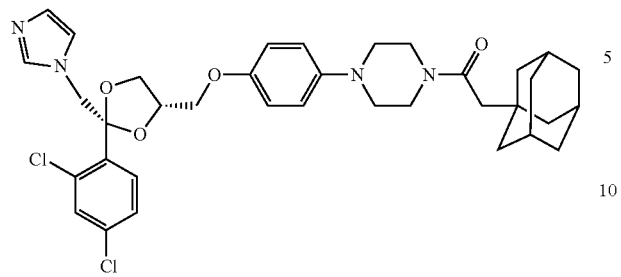

Compound 40

Scheme 17. The reactive Ketoconazole precursor (55 mg, 0.15 mmol) from scheme 13 and Adamantane-linker conjugate (55 mg, 0.16 mmol) from scheme 4 were dissolved in dichloromethane (4 mL) and treated with 3 equivalents of triethanolamine and 1.2 equivalents of bis(2-oxo-3-oxazolidinyl)phosphinic chloride. Reaction was stirred 2 hours. Reaction was diluted with ethyl acetate and washed with sodium bicarbonate and brine. Purified by Si Gel chromatography using ethyl acetate. The following AR Antagonist-Adamantane-Linker conjugate compounds are produced, where n is from 0 to 10.

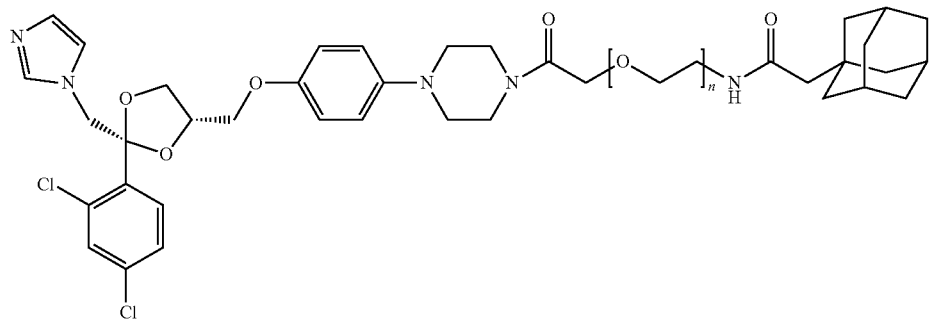

Using Scheme 17, the following AR Antagonist-Adamantane-Linker conjugate compounds were produced:

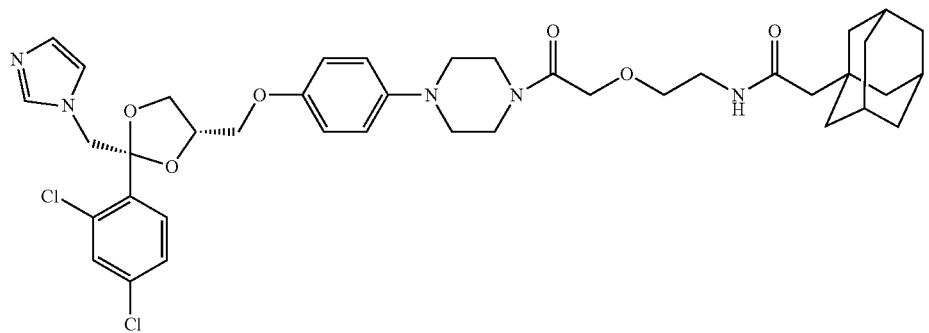

Compound 41

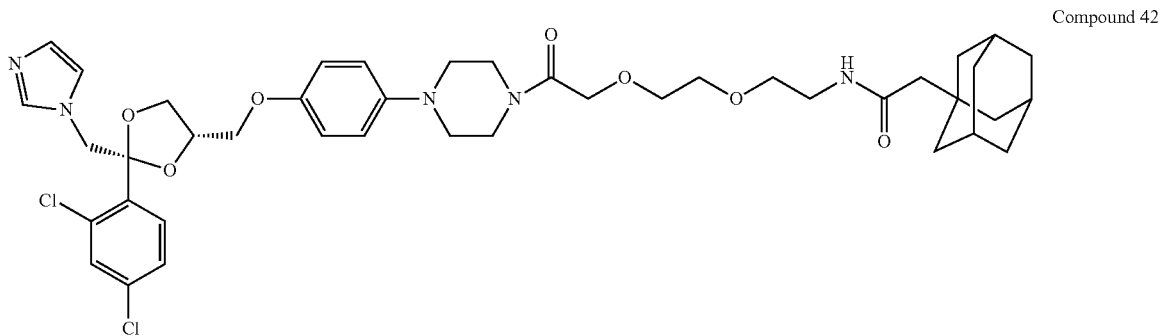

Compound 42

Reaction schemes similar to scheme 17 can be performed except that instead of Adamantane precursor from scheme 4, any one of the other Adamantane precursors from schemes 3 or 5-10 can be used.

Example 7

Preparation of AR Antagonist-HIF-1α-Linker Conjugate

Scheme 18. The reactive Spironolactone precursor (55 mg, 0.15 mmol) from scheme 12 and HIF-1α-linker conjugate (55 mg, 0.16 mmol) from scheme 11 were dissolved in dichloromethane (4 mL) and treated with triethanolamine (63 μL, 0.45 mmol) and bis(2-oxo-3-oxazolidinyl)phosphinic chloride (41 mg, 0.16 mmol). Reaction was stirred 2 hours. Minimal product had formed. 4-dimethylaminopyridine was added and stirring was continued overnight. Reaction was diluted with ethyl acetate and washed with citric acid saturated sodium bicarbonate and brine. Purified by Si Gel chromatography using ethyl acetate. The following AR Antagonist-HIF-1α-Linker conjugate compounds are produced, where n is from 0 to 10.

Scheme 18

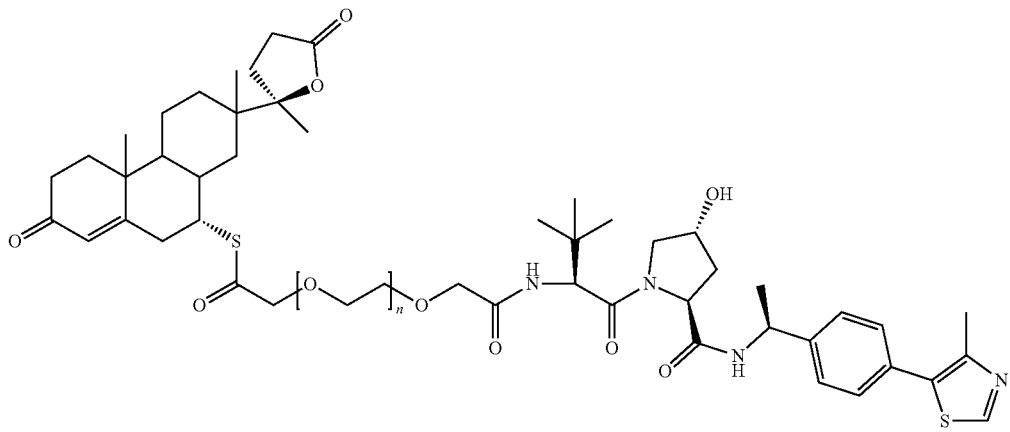

Using Scheme 18, the following AR Antagonist-HIF-1α-Linker conjugate compounds were produced:
Compound 43
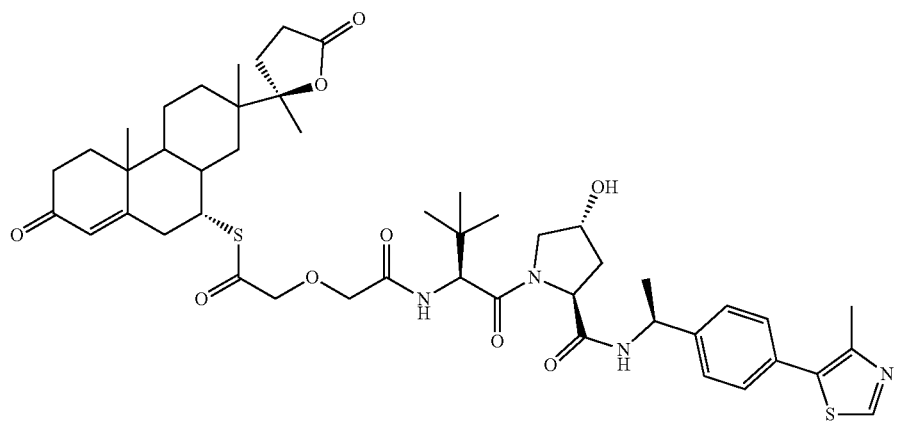
Compound 44
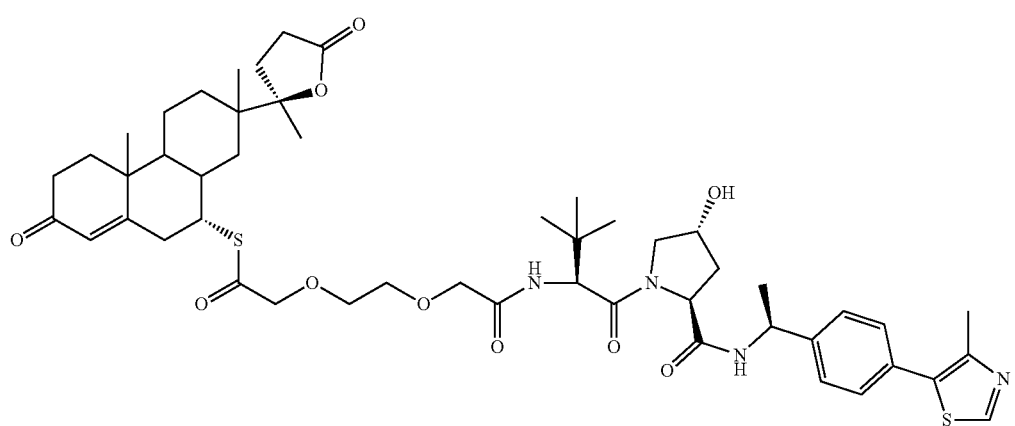
Compound 45
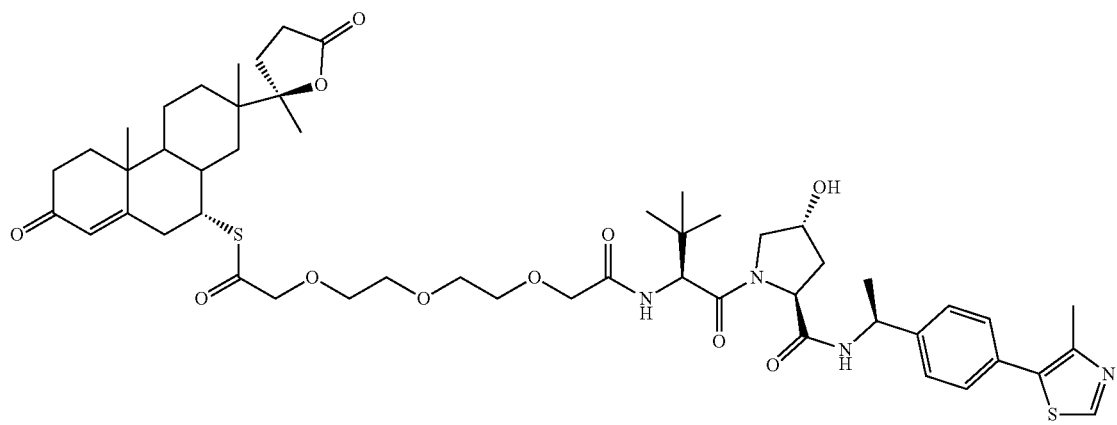

Compound 46

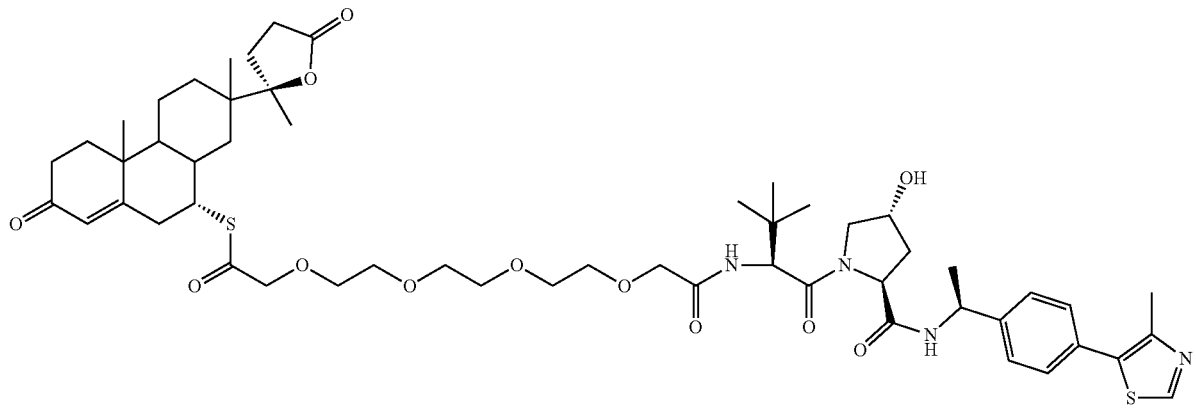

Reaction schemes similar to scheme 18 can be performed except that HIF-1α attached to any one of the other linkers from schemes 3-8 or 10 can be used.

Example 8

Preparation of AR Antagonist-HIF-1α-Linker Conjugate

Scheme 19. The reactive Ketoconazole precursor (55 mg, 0.15 mmol) from scheme 13 and HIF-1α-linker conjugate (55 mg, 0.16 mmol) from scheme 11 were dissolved in dichloromethane (4 mL) and treated with 3 equivalents of triethanolamine and 1.2 equivalents of bis(2-oxo-3-oxazolidinyl)phosphinic chloride. Reaction was stirred 2 hours. Reaction was diluted with ethyl acetate and washed with sodium bicarbonate and brine. Purified by Si Gel chromatography using ethyl acetate. The following AR Antagonist-HIF-1α-Linker conjugate compounds are produced, where n is from 0 to 10.

Scheme 19

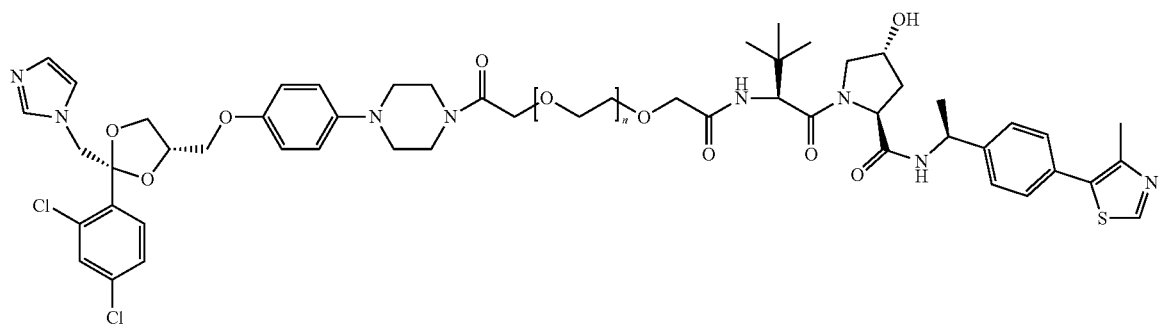

Using Scheme 19, the following AR Antagonist-HIF-1α-Linker conjugate compounds were produced:
Compound 47
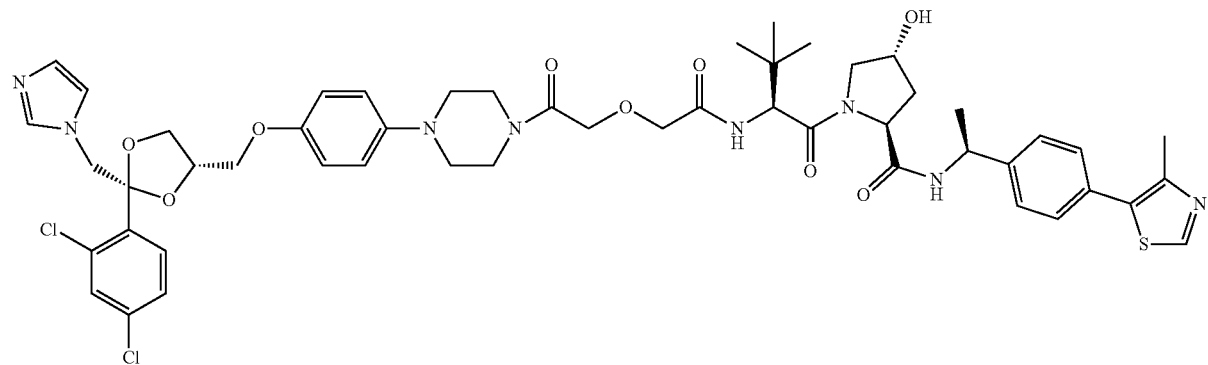
Compound 48
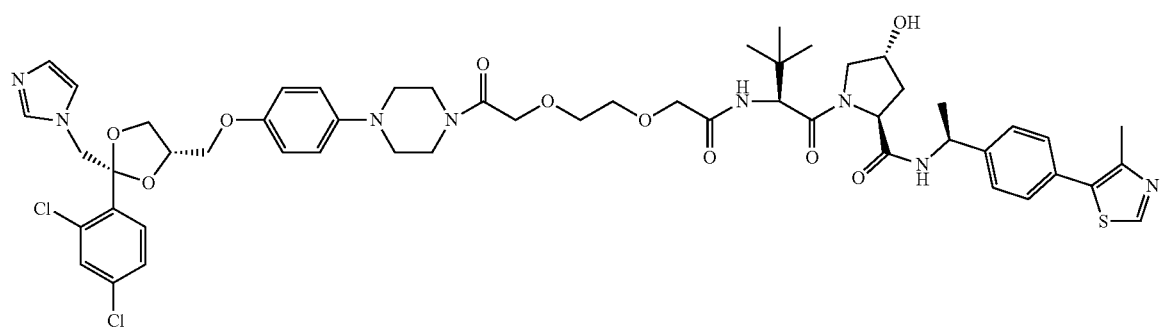
Compound 49
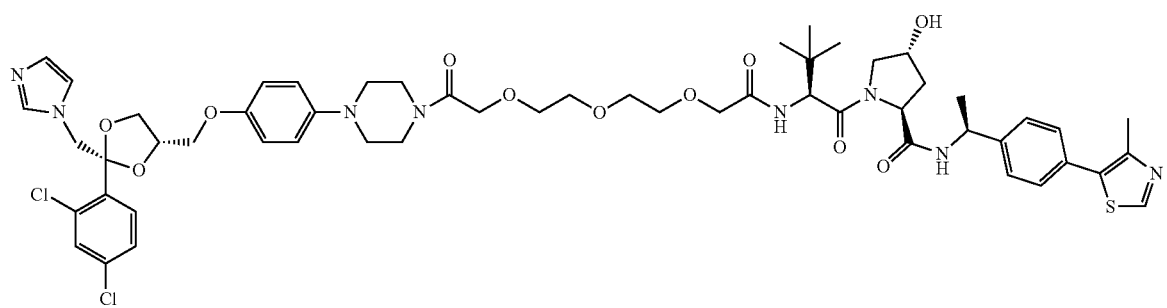
Compound 50
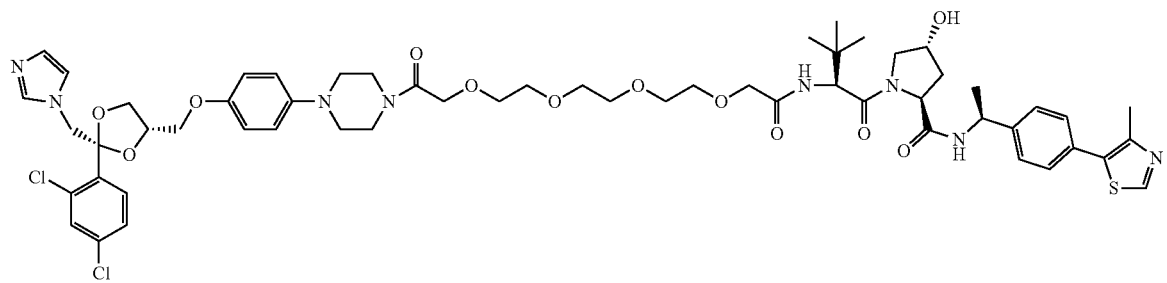

Reaction schemes similar to scheme 19 can be performed except that HIF-1α attached to any one of the other linkers from schemes 3-8 or 10 can be used.
Example 9
Preparation of Additional AREs
Using the procedures described in Examples 4-8 the following additional AREs comprising methoxybenzyl lactam are produced:
Compound 51
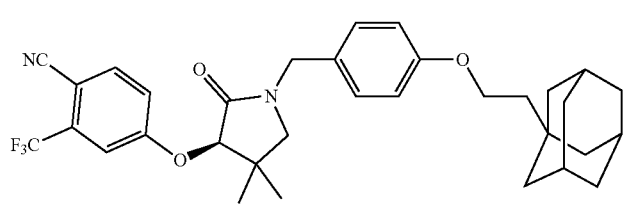
Compound 52
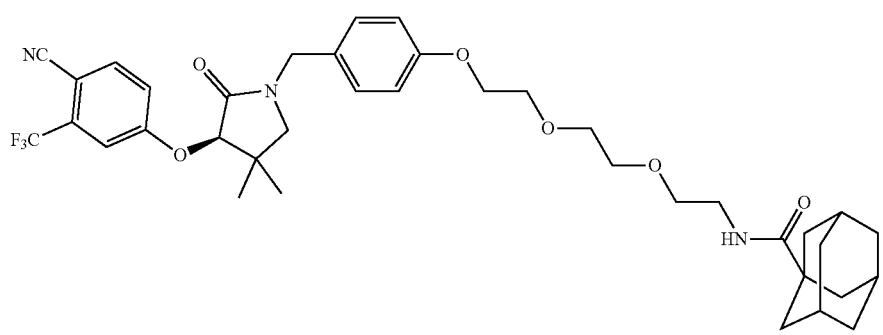
Compound 53
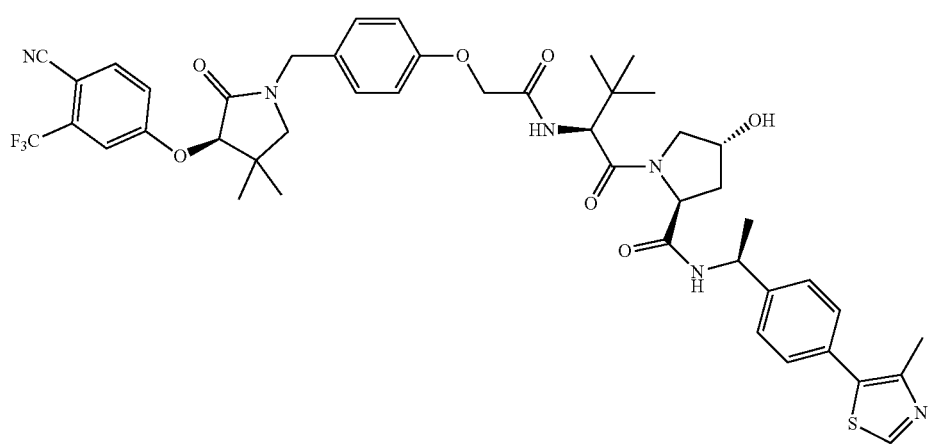
Compound 54
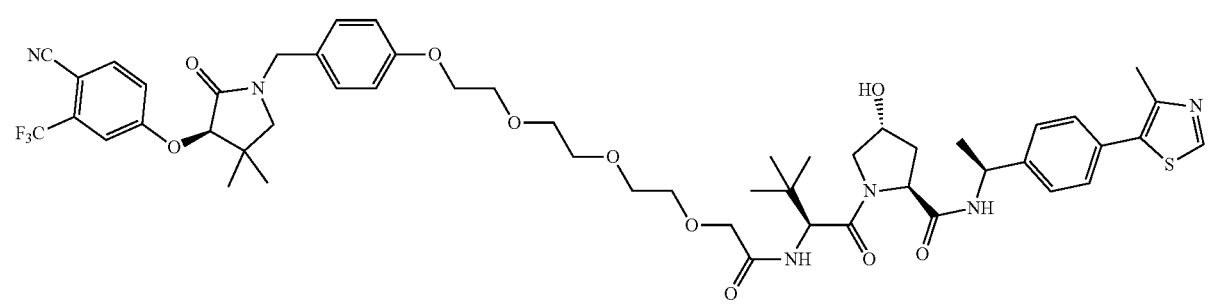

Reaction schemes similar to those described in Examples 4-8 can be performed except that adamantane or HIF-1α attached to any one of the other linkers from schemes 3-9 can be used.

Example 10

Inhibition Assay

This example illustrates how to determine the inhibitory activity of an ARE disclosed herein using a cell-based androgen receptor transcriptional reporter assay using an engineered cell line.

For the MDA-kb2 assay, MDA-kb2 mammary gland breast cancer cell line was maintained in L-15 media (Gibco) supplemented with 10% FBS, 100 U/mL penicillin, 100 μg/mL streptomycin, and 0.25 μg/mL amphotericin B at 37° C., without $CO_2$. For experiments, cells were plated at $1.0 \times 10^4$ cells (50% confluence) per well in 100 μL of medium in 96-well plates. When cells were attached (after 6 hours), medium was removed and replaced with dosing medium containing 10% charcoal stripped FBS.

For the Keratinocyte assay, normal Human Adult Primary Epidermal Keratinocyte cell line (ATCC PCS-200-011) was maintained in EPIUFE® Medium, with 60 μM calcium (Thermo MEPISOOCA) supplemented with Human Keratinocyte Growth Supplement, 100 U/mL penicillin, and 100 μg/mL streptomycin at 37° C. with 5% $C_{O2}$. For experiments, cells were seeded at 70% confluence per well in 100 μL of medium in 96-well plates. Reverse transfection was done on the cells using Lipofectamine 3000 (Life Technologies) with plasmids according to manufacturer's instructions. Briefly, 0.3 μL transfection reagent per 100 ng DNA were incubated with P3000 reagent and Opti-Mem prior to addition of cells. After 16 hours, medium was removed and replaced with dosing medium.

A 5α-Androstan-17β-ol-3-one (DHT) stock solution was prepared at 1,000× in ethanol. Each ARE tested was prepared in DMSO. Dosing medium was prepared at the time of treatment by serial diluting stock solution into medium. Ethanol concentrations in media never exceeded 0.1%. SPG-001 is Spironolactone; SPG-002 is Ketoconazole; SPG-003 is Spironolactone-Adamantane ARE (Compound 37); SPG-004 is Spironolactone-Adamantane ARE (Compound 39); SPG-005 is Ketoconazole-Adamantane ARE (Compound 42); and SPG-006 is Ketoconazole-Adamantane ARE (Compound 40). Negative control wells contained 100 μL medium/well with 1 μL of ethanol/mL of medium and an appropriate amount of DMSO. Each plate also contained 1.0 nM DHT with an ARE or without an ARE as a positive control. Cells were incubated 24 hours at 37° C. without $CO_2$.

To assess for cell viability, cells were first visually examined under a phase-contrast microscope to record cell confluence, morphological changes, and presence of drug crystallization as well as to observe signs of cytotoxicity such as, e.g., detachment, vacuolization, membrane degradation, or lack of phase brightness. After microscopic inspection, a Trypan Blue exclusion assay was performed to assess cell viability and cell number for each well. Each well was washed with 0.5 mL volume of PBS. 30 UL of Trypan Blue was added to each well for 5-10 minutes. Total cell number and total viable cell number will be counted from 1 number of fields per well, in triplicate.

To assess ARE-mediated inhibition, an AR luciferase assay was performed. After washing cells with 1×PBS, 20 μL lysis buffer (25 mM Tris/phosphate, 4 mM EGTA, 1% Triton, 10% glycerol, 2 mM DTT) was added per well, incubated for 5 minutes with gentle shaking and store at −80° C. On the day of assay, the plates were thawed to ambient temperature and 80 μL of assay buffer (25 mM glycylglycine, 15 mM $MgCl_2$, 5 mM ATP, 0.1 mg/ml BSA) was added to each well. Plates are then processed on a microplate reader (POLARstar Omega) by injecting 100 μL of 1 mM D-luciferin per well, followed by chemiluminescence measurement of 3 seconds at onset of injection. Luciferase activity was determined, measured, and normalized to Relative Light Units (RLU). AR reporter gene activity reduction values were calculated as follows: AR reporter gene activity=1−(average signal (treatment group)/average signal (treatment group without drug).

To assess levels of AR, an ELISA was performed.

The results of two independent MDA-kb2 assays are shown in Table 1. A dose-dependent inhibition of AR reporter gene activity was observed for all compounds tested. In addition, the addition of an AR elimination promoter or elimination enhancer element significantly increased the degree of inhibition observed. For example, Spironolactone demonstrated 41% reduction in AR reporter gene activity at 10 μM, while SPG-003 exhibited 90% reduction in AR reporter gene activity at 10 μM (Table 1). Similarly, Ketoconazole demonstrated 43% reduction in AR reporter gene activity at 10 μM, while SPG-005 exhibited 80% reduction in AR reporter gene activity at 10 μM (Table 1). A dose-dependent reduction in AR protein levels were also observed for all compounds tested. In addition, the addition of an AR elimination promoter or elimination enhancer element significantly increased the degree of inhibition observed. For example, Spironolactone demonstrated 35% reduction in AR protein level at 10 μM, while SPG-003 exhibited 71% reduction in AR protein level at 10 μM (Table 1). Similarly, Ketoconazole demonstrated 10% reduction in AR protein level at 10 μM, while SPG-005 exhibited 54% reduction in AR protein level at 10 μM (Table 1).

TABLE 1

MDA-KB2 AR Reporter Gene Assay

| Treatment | Cell Viability | Gene Activity Reduction | AR Reduction |
|---|---|---|---|
| Negative Control | 99% | 0% | 0% |
| Positive Control | 99% | 80% * | 43% * |
| 0.1 μM SPG-001 | 99% | 12% * | — |
| 1.0 μM SPG-001 | 98% | 28% * | — |
| 3.0 μM SPG-001 | 98% | 39% * | 31% * |
| 10 μM SPG-001 | 98% | 41% * | 35% * |
| 0.1 μM SPG-002 | 97% | 4% * | — |
| 1.0 μM SPG-002 | 98% | 7% * | — |
| 3.0 μM SPG-002 | 98% | 16% * | 4% * |
| 10 μM SPG-002 | 98% | 43% * | 10% * |
| 0.1 μM SPG-003 | 98% | 8% * | — |
| 1.0 μM SPG-003 | 99% | 20% * | — |
| 3.0 μM SPG-003 | 98% | 40% * | 25% * |
| 10 μM SPG-003 | 98% | 90% * | 71% * |

TABLE 1-continued

MDA-KB2 AR Reporter Gene Assay

| Treatment | Cell Viability | Gene Activity Reduction | AR Reduction |
|---|---|---|---|
| 0.1 μM SPG-004 | 97% | 11% * | — |
| 1.0 μM SPG-004 | 98% | 22% * | — |
| 3.0 μM SPG-004 | 99% | 36% * | 29% * |
| 10 μM SPG-004 | 98% | 42% * | 50% * |
| 0.1 μM SPG-005 | 98% | 9% * | — |
| 1.0 μM SPG-005 | 98% | 14% * | — |
| 3.0 μM SPG-005 | 98% | 18% * | 8% * |
| 10 μM SPG-005 | 98% | 80% * | 54% * |
| 0.1 μM SPG-006 | — | — | — |
| 1.0 μM SPG-006 | — | — | — |
| 3.0 μM SPG-006 | — | — | — |
| 10 μM SPG-006 | — | — | — |

* p-value < 0.05 (T-test) compared to respective control and has inhibitory effect.

The results of a Keratinocyte assays are shown in Table 2. A dose-dependent inhibition of AR reporter gene activity was observed for all compounds tested. In addition, the addition of an AR elimination promoter or elimination enhancer element significantly increased the degree of inhibition observed. For example, Spironolactone demonstrated 59% reduction in AR reporter gene activity at 10 μM, while SPG-003 exhibited 93% reduction in AR reporter gene activity at 10 μM (Table 2). Similarly, Ketoconazole demonstrated 56% reduction in AR reporter gene activity at 10 μM, while SPG-005 exhibited 90% reduction in AR reporter gene activity at 10 μM (Table 2). A dose-dependent reduction in AR protein levels were also observed for all compounds tested. In addition, the addition of an AR elimination promoter or elimination enhancer element significantly increased the degree of inhibition observed. For example, Spironolactone demonstrated 51% reduction in AR protein level at 10 μM, while SPG-003 exhibited 65% reduction in AR protein level at 10 μM (Table 2). Similarly, Ketoconazole demonstrated 20% reduction in AR protein level at 10 μM, while SPG-005 exhibited 65% reduction in AR protein level at 10 μM (Table 2).

TABLE 2

Keratinocyte AR Reporter Gene Assay

| Treatment | Cell Viability | Gene Activity Reduction | AR Reduction |
|---|---|---|---|
| Negative Control | 94% | 0% | 0% |
| Positive Control | 95% | 90% * | 52% * |
| 0.1 μM SPG-001 | 92% | 21% * | 12% * |
| 1.0 μM SPG-001 | 94% | 37% * | 30% * |
| 3.0 μM SPG-001 | 92% | 54% * | 42% * |
| 10 μM SPG-001 | 95% | 59% * | 51% * |
| 0.1 μM SPG-002 | 95% | 13% * | 2% |
| 1.0 μM SPG-002 | 93% | 18% * | 10% * |
| 3.0 μM SPG-002 | 94% | 30% * | 11% * |
| 10 μM SPG-002 | 95% | 56% * | 20% * |
| 0.1 μM SPG-003 | 93% | 21% * | 6% * |
| 1.0 μM SPG-003 | 93% | 31% * | 19% * |
| 3.0 μM SPG-003 | 94% | 50% * | 26% * |
| 10 μM SPG-003 | 93% | 93% * | 65% * |
| 0.1 μM SPG-004 | — | — | — |
| 1.0 μM SPG-004 | — | — | — |
| 3.0 μM SPG-004 | — | — | — |
| 10 μM SPG-004 | — | — | — |
| 0.1 μM SPG-005 | 94% | 21% * | 12% * |
| 1.0 μM SPG-005 | 92% | 29% * | 19% * |
| 3.0 μM SPG-005 | 93% | 31% * | 23% * |
| 10 μM SPG-005 | 94% | 90% * | 65% * |
| 0.1 μM SPG-006 | 93% | 8% * | 1% |
| 1.0 μM SPG-006 | 94% | 19% * | 5% * |
| 3.0 μM SPG-006 | 94% | 28% * | 20% * |
| 10 μM SPG-006 | 94% | 48% * | 37% * |

* p-value < 0.05 (T-test) compared to respective control and has inhibitory effect.

Example 11

Inhibition Assay

This example illustrates how to determine the inhibitory activity of an ARE disclosed herein using a cell-based androgen receptor transcriptional reporter assay using primary human keratinocytes.

For the Keratinocyte assay, normal Human Adult Primary Epidermal Keratinocyte cell line (ATCC PCS-200-011) was maintained in EPIUFE® Medium, with 60 μM calcium (Thermo MEPISOOCA) supplemented with Human Keratinocyte Growth Supplement, 100 U/mL penicillin, and 100 μg/mL streptomycin at 37° C. with 5% C02. For experiments, cells were seeded at 70% confluence per well in 100 μL of medium in 96-well plates. Reverse transfection was done on the cells using Lipofectamine 3000 (Life Technologies) with plasmids according to manufacturer's instructions. Briefly, 0.3 μL transfection reagent per 100 ng DNA were incubated with P3000 reagent and Opti-Mem prior to addition of cells. After 16 hours, medium was removed and replaced with dosing medium.

To assess ARE-mediated inhibition, an AR luciferase assay was performed as described in Example 10. To assess levels of AR, an ELISA was performed as described in Example 10.

A Niclosamide stock solution was prepared at 1,000× in ethanol. Each ARE tested was prepared in DMSO. Dosing medium was prepared at the time of treatment by serial diluting stock solution into medium. Ethanol concentrations in media never exceeded 0.1%. SPG-001 is Spironolactone; SPG-002 is Ketoconazole; SPG-003 is Spironolactone-Adamantane ARE (Compound 37); and SPG-005 is Ketoconazole-Adamantane ARE (Compound 42). Negative control wells contained 100 L medium/well with 1 μL of ethanol/mL of medium and an appropriate amount of DMSO. Each ARE was applied to keratinocytes in concentrations up to 50 M. Each plate also contained 1.0 nM Niclosamide with an ARE or without an ARE as a positive control. Cells were incubated 72 hours at 37° C. without $CO_2$.

The results are shown in Table 3. $IC_{50}$ values were calculated as follows: SPG-001:50 μM; SPG-002:11 μM; SPG-003: about 50 M; SPG-005:2 μM; and Niclosamide: <0.2 μM. The results showed that both SPG-001 and SPG-003 had essentially the same cytotoxic effects with equivalent $IC_{50}$ values when 50 μM of each was applied to keratinocytes. Niclosamide, a drug previously shown to be cytotoxic to these cells had an $IC_{50}$ of below 0.2 μM. These results indicate that SPG-003 had comparable cytotoxicity in skin cells to its parent, the AR antagonist Spironolactone (Table 3).

TABLE 3

Cell Viability Assay

| Concentration (μM) | SPG-001 | SPG-002 | SPG-003 | SPG-005 | Niclosamide |
|---|---|---|---|---|---|
| 50 | 58.33 ± 2.39 | 7.29 ± 12.16 | 38.67 ± 2.25 | 0.09 ± 6.41 | 0.20 ± 6.09 |
| 16.67 | 82.73 ± 1.34 | 41.59 ± 1.76 | 55.11 ± 0.16 | 0.11 ± 1.77 | 15.93 ± 7.45 |
| 5.56 | 99.27 ± 1.50 | 71.22 ± 0.88 | 66.12 ± 3.09 | 1.98 ± 8.39 | 25.07 ± 3.81 |
| 1.85 | 108.09 ± 1.79 | 90.96 ± 2.34 | 73.46 ± 1.11 | 62.57 ± 2.06 | 30.65 ± 5.98 |
| 0.62 | 113.05 ± 1.09 | 93.61 ± 3.38 | 92.16 ± 1.30 | 77.01 ± 0.64 | 34.13 ± 2.99 |
| 0.21 | 116.28 ± 2.79 | 110.17 ± 0.78 | 115.90 ± 0.49 | 93.72 ± 1.69 | 45.57 ± 4.55 |
| 0 | 100 ± 0.79 | 100 ± 0.79 | 100 ± 0.79 | 100 ± 0.79 | 100 ± 0.79 |

Example 12

Inhibition Assay

This example illustrates how to determine the inhibitory activity of an ARE disclosed herein using a cell-based androgen receptor transcriptional reporter assay using primary human keratinocytes.

To assess ARE-mediated inhibition, an AR luciferase assay was performed as described in Example 10 to examine the effects of SPG-001 (Spironolactone), SPG-002 (Ketoconazole), SPG-003 (a Spironolactone-Adamantane ARE, Compound 37), SPG-007 (a Ketoconazole-HIF-1α ARE, Compound 47), SPG-008 (a Ketoconazole-HIF-1α ARE, Compound 49), and SPG-009 (a Spironolactone-HIF-1α ARE, Compound 43) after continuous exposure for 24 and 72 hours. To assess levels of AR, an ELISA was performed as described in Example 10. Results were analyzed for $IC_{50}$ and $IC_{90}$ values in GraphPad Prism using a four-parameter logistic curve equation. Bottom constraints were set to 1 (level of uninduced control). All reported values had an R-square value greater than 0.96.

At both time points in this experiment, SPG-003 was superior to SPG-001 (Table 4). For example, the maximum observed inhibition of reporter gene activity was 65% for SPG-001 and 91% for SPG-003 after 24 hours of treatment. The $IC_{50}$ for SPG-003 for the 24-hr treatment was 3.7 μM and the $IC_{90}$ was 7 μM. Neither parameter could be calculated for SPG-001 in this experiment. SPG-003 was the best performing compound of the group tested in this study.

As was seen in the 24-hour treatment, SPG-003 was superior to SPG-001 in both $IC_{50}$ and $IC_{90}$ as well as maximum observed inhibition of reporter gene activity after the 72-hour treatment. Interestingly, the calculated $IC_{50}$ of SPG-003 was reduced from 3.7 μM to 2.5 μM (Table 4). The calculated $IC_{90}$ of SPG-003 was also reduced from 7 μM to 5.7 μM (Table 4). This suggests that extended treatment with SPG-003 results in better inhibition of the target AR reporter gene. A dose-dependent inhibition of AR reporter gene activity was observed for SPG-003. SPG-003 had increased potency and inhibition of AR reporter gene activity with extended treatment while cell cytotoxicity was minimal in human keratinocytes.

TABLE 4

Keratinocyte AR Reporter Gene Assay

| | 24-hr Treatment | | | 72-hr Treatment | | |
|---|---|---|---|---|---|---|
| Compound | $IC_{50}$ (M) | $IC_{90}$ (M) | Maximum Inhibition | $IC_{50}$ (M) | $IC_{90}$ (M) | Maximum Inhibition |
| SPG-001 | No S-curve | No S-curve | 65% | $4.51 \times 10^{-6}$ | $1.66 \times 10^{-6}$ | 85% |
| SPG-002 | $5.45 \times 10^{-6}$ | $9.67 \times 10^{-5}$ | 59% | $2.39 \times 10^{-6}$ | $1.84 \times 10^{-5}$ | 83% |
| SPG-003 | $3.68 \times 10^{-6}$ | $6.96 \times 10^{-6}$ | 91% | $2.57 \times 10^{-6}$ | $5.68 \times 10^{-6}$ | 93% |
| SPG-007 | $4.58 \times 10^{-6}$ | $7.38 \times 10^{-5}$ | 67% | $1.50 \times 10^{-6}$ | $2.22 \times 10^{-5}$ | 80% |
| SPG-008 | $3.31 \times 10^{-6}$ | $8.40 \times 10^{-6}$ | 94% | $2.38 \times 10^{-6}$ | $7.86 \times 10^{-6}$ | 94% |
| SPG-009 | $4.58 \times 10^{-6}$ | $1.12 \times 10^{-5}$ | 90% | $3.05 \times 10^{-6}$ | $8.17 \times 10^{-6}$ | 92% |

The sustained effects of SPG-001 versus SPG-003 was also examined in human keratinocytes transfected with an AR luciferase reporter gene. Cells were transfected with the reporter gene and then treated with 7 µM SPG-001 or 7 µM SPG-003 for 24 hours. After 24 hours, the cells were washed and media was replaced with new media that did not contain any AR antagonist. Reporter gene activity was measured following two days or three days of additional cell culture in the absence of AR antagonists. AR reporter gene activity reduction was calculated as follows: 1−(average signal (treatment group)/(average signal (treatment group, without drug, same washout period).

The results of that experiment showed that SPG-003 had sustained inhibition of reporter gene activity over three days that was significantly better than what was observed with cells treated with SPG-001. For example, as seen in Table 5, three days after the removal of SPG-003, reporter gene activity was suppressed by 48% in SPG-003 treated cells. However, cells treated with SPG-001 at that same concentration only showed 24% inhibition of the reporter gene. These data again highlight the superiority of SPG-003 as an AR antagonist in comparison to its parent SPG-001 (spironolactone). Cell viability was between 90% and 100% for both compounds over the duration of this study.

TABLE 5

Keratinocyte AR Reporter Gene Assay

| Washout Period | Niclosamide (0.5 µM) | SPG-001 (7.0 µM) | SPG-003 (7.0 µM) |
| --- | --- | --- | --- |
| 0 days | 90 ± 0.2%* | 67 ± 1.1%* | 89 ± 1.0%* |
| 2 days | 70 ± 0.9%* | 40 ± 2.5%* | 64 ± 0.3%* |
| 3 days | 58 ± 2.6%* | 24 ± 2.3%* | 48 ± 2.4%* |

* p-value < 0.05 (T-test) compared to respective control and has inhibitory effect.

Example 13

Inhibition Assay

This example illustrates how to determine the inhibitory activity of an ARE disclosed herein using a cell-based androgen receptor transcriptional reporter assay using primary human keratinocytes.

To determine efficacy of a compound, a MDA-kb2 assay was performed as described in Example 10. The cells were treated with compounds for 24 hours prior to measurements of reporter gene activity. The $IC_{50}$ and $IC_{90}$ of SPG-001 and SPG-003 was determined in MDA-kb2 cells treated with 0.1 nM DHT for 24 hours. AR luciferase assay results were analyzed using GraphPad Prism using a four-parameter logistic curve equation. Bottom constraints were set at 1 (level of uninduced control.)

Even though hormone levels were reduced to better model the parameters of female human skin, reporter gene activity was still quite significant with a 12-fold induction relative to control cells not exposed to DHT. In this experiment, SPG-001 had no apparent ability to inhibit reporter gene activity. Cyproterone acetate, an approved AR antagonist actually demonstrated AR agonist activity at concentrations above 3.3 µM with limited antagonistic activity at concentrations below 1 µM. SPG-003 showed a maximum inhibition of reporter gene activity of 95%, an $IC_{50}$ of 789 nM, an $IC_{90}$ of 2.71 µM. MDA-kb2 breast cancer cell viability started to decline from 80% to 50% upon treatment with 6 µM to 10 µM of SPG-003 though this phenomenon was not previously seen in similar experiments with this cell line and should be investigated more carefully. These experiments demonstrated a dose-dependent inhibition of AR reporter gene activity for SPG-003. This dose-dependent inhibition was not observed for SPG-001 or Cyproterone acetate under conditions of reduced (10-fold relativity previous experiments) DHT levels.

TABLE 6

MDA-kb2 Assay

| Compound | $IC_{50}$ (M) | $IC_{90}$ (M) | Maximum Inhibition |
| --- | --- | --- | --- |
| SPG-001 | — | — | 0% |
| SPG-003 | $7.89 \times 10^{-7}$ | $2.71 \times 10^{-6}$ | 95% |
| Cyproterone acetate | — | — | 24% |

* p-value < 0.05 (T-test) compared to respective control and has inhibitory effect.

Example 14

Formulation Studies

A study was conducted to develop an experimental formulation for the topical delivery of SPG-003 to human and mouse skin. The results of those studies identified experimental formulations which were then applied to both human and mouse skin using standard FDC chambers. A formulation consisting of IPM/Ethanol/Transcutol/49.8/30/20 w/w/w was identified from these formulation studies as optimal. These studies demonstrated significant permeation into the dermis and epidermis of SPG-003 and suggested that these formulations could be used to effectively inhibit the AR in vivo when applied topically.

Solubility screening tests were performed in 8 solvent systems: (1) Transcutol: Ethanol: Isopropyl myristate (IPM) 2:3:5 (v:v); (2) Transcutol: Ethanol 3:7 (v:v); (3) Ethanol: Propylene Glycol 1:1 (v:v); (4) Ethanol:H2O 7:3 (v:v); (5) IPM; (6) Ethanol:Tween 80: Cetyl Alcohol 90:5:5 (w:w); (7) CCT: Tween 80: Cetyl Alcohol 90:5:5 (w:w); and (8) CCT: Isopropanol 1:1 (v: v). These solvent systems were selected from FDA Inactive Ingredients Database (IIG). One objective was to identify solvent systems for solution formulation at targeted API concentration of 1% by weight. Another objective was to identify solvents that are potentially good penetration enhancers and yet clinically viable. Since cetyl alcohol is solid, the solvent systems with them were prepared in weight ratios.

For solvent systems (3), (4), (5) and (7), SPG-003 was not soluble after extensive sonication. For solvent (1), (2), (6) and (8), SPG-003 had good solubility in those solvent systems. Transcutol: Ethanol:IPM 2:3:5 (v:v) was picked as solution formulation since it has a good penetration enhancer (transcutol) and a lipid IPM (clinically viable).

To examine the penetration ability of SPG-003 formulation, two different assays were conducted. The SPG-003 formulation was prepared by adding SPG-003 (final concentration 1.0% by weight) to a mixture comprising 30% denatured alcohol. 49% IPM, 20% Transcutol and sonicaing this mixture until the compound was dissolved.

Human cadaver skin tissue was purchased from a tissue bank in the U.S. Two lots of the dermatomed skin tissue were used. Donor demographics: tissue 08033 (average thickness: 397 µm): sex=male, age=58, race=Caucasian, and anatomical site=abdomen; tissue 08696 (average thickness; 1,040 µm): sex=male, age=50, race=Caucasian, and anatomical site=abdomen. The thickness was measured using a digital snap gage. Duplicate for each donor (N=2). The tissue was received in dry ice packaging. It was stored at −20° C. until use.

After passing initial visual inspection, barrier integrity of the skin tissue was evaluated using transepidermal electrical resistance measurement (TEER measurement). Measurement was conducted using a LCR meter at a frequency of 100 Hz at room temperature. The measurement medium was 0.9% NaCl solution, using a pair of stainless steel electrodes. Prior to the skin absorption and penetration study, electrical resistance value for each lot of human skin tissue was evaluated. Due to potential lot-to-lot variation in donor age, sex, race, and anatomical site, objective of the measurement was to establish threshold value for intact cadaver tissue for each lot to be used in the present skin absorption and penetration study. Six (6) tissue samples from selected spots from each lot were taken. Transepidermal electrical resistance value (TEER measurement, Z value) was measured. All reported TEER values are net values after subtraction of the measurement medium blank (about 1.3 KOhms). It was determined that the threshold TEER value was 6.0 KOhms for donor 08033 and 10 KOhms for donor 08696. For those tissues with visible defects, the TEER value was found in the range of 0.1 KOhms to 0.5 KOhms.

The formulation screening study was carried out in a High-Throughput Screening (HTS) station. The skin tissue samples (after washed with 1×PBS, pH 7.4) were mounted on diffusion cells in HTS station. A total of 4 cells were used in the study. Each cell in the station has a diffusion area of 0.503 cm$^2$ (8 mm in diameter). Each individual cell is static Franz-Cell type. The receptor chamber was filled with 3.0 mL of 4% BSA in water, supplemented with 0.01% gentamicin sulfate, which was vigorously and continuously mixed. The temperature was set at 32±0.1° C. The tissue samples in the HTS cells were equilibrated at 32±0.1° C. for 1 hour before dosing. The applied SPG-003 formulation dose for each sample was 5.0 μL and each sample was run in two replicates.

The data collection time point was 8 hours. At end of the time interval, the skin tissues were removed from the cells. The tissue surface was carefully wiped with Q-tip wetted with distilled water, followed by wiping with dry Q-tip one time; then, wiped with Q-tip wetted with distilled water, followed by wiping with dry Q-tip one more time. Then, two cycles of tape-stripping were performed to remove residual formulation left on the skin surface (un-absorbed/un-penetrated). Then, the standard tape-stripping method was used to remove the SC layer. Scotch tape was used in tape-stripping process. The tape-stripping cycle was repeated for a total of 15 times. It has been established in our laboratory that 15-stripping-cycle is sufficient to completely remove the SC layer from human cadaver skin. The collected tape strips were discarded. After removal of the SC layer, epidermis and dermis layer were cut into pieces and extracted with 7.0 ml of DMSO/ACN=1:1 v/v for overnight at room temperature using an orbit shaker. The extracts were collected and ready for analysis. The receptor fluid was collected and prepared for analysis. A liquid chromatography-tandem mass spectrometry (LC-MS/MS) method was developed for the quantitation of SPG-003 in BSA and human skin soaked in DMSO/ACN=1:1 v/v matrix samples. The concentration range of the SPG-003 calibration was 1 ng/ml to 120 ng/ml for BSA matrix and 10 ng/ml to 1000 ng/ml for human ear skin soaked in DMSO/ACN=1:1 v/v matrix samples.

TABLE 7

Human Skin Penetration Assays

| Assay | Donor 08033 | | Donor 08696 | |
|---|---|---|---|---|
| | Run 1 | Run 2 | Run 1 | Run 2 |
| Receptor - 8 hr | 1.4 ng | 0.9 ng | 1.2 ng | 1.0 ng |
| Epidermis/Dermis - 8 hr | 931.0 ng | 471.8 ng | 3311.0 ng | 1897.0 ng |
| Epidermis/Dermis - 8 hr | 89.1 μM | 45.1 μM | 117.1 μM | 67.1 μM |

Compound SPG-003 shows limited amount of skin penetration, but good amount of skin retention in epidermis and dermis after 8 hours of exposure.

Based on the results above, a similar skin penetration study was performed using hamster skin model. Both SPG-003 and Spironolactone were formulated with Transcutol: Ethanol: IPM 2:3:5 (v: v) as described above. The applied formulation dose for each sample was 10.0 μL and each sample was run in four replicates. The samples were evaluated at the 8-hour time point for compound absorption in epidermal and dermal layers and penetration into receptor medium.

TABLE 8

Hamster Skin Penetration Assays

| Assay | SPG-003 Formulation | | | |
|---|---|---|---|---|
| | Run 1 | Run 2 | Run 3 | Run 4 |
| Receptor - 8 hr | 2.46 | 5.28 | 3.69 | 5.70 |
| Epidermis/Dermis - 8 hr | 12840 | 9120 | 11960 | 4200 |
| Receptor - 8 hr | 4230 | 2997 | 2781 | 3690 |
| Epidermis/Dermis - 8 hr | 6240 | 6760 | 5600 | 13360 |

Compound SPG-003 has limited amount of skin penetration, but it has good amount of skin absorption. In other words, it mainly retained in epidermis/dermis layer. Compound Spironolactone has good amount of skin penetration and absorption.

Example 15

In Vivo Androgenetic Alopecia Studies

These experiments tested stability of the SPG-003 formulation in a solution was well as mouse skin homogenate.

To test formulation stability in solution, about 100 mg of the SPG-003 formulation was weighted in a 4 mL vial and 3 mL of ethanol was added to fully dissolve the formulation. Then 300 μL of ethanol solution was added into 700 μL of acetonitrile/H$_2$O (70/30 v/v) to make 1 mL of final solution and mixed well for HPLC analysis. The solution formulations of SPG-003 were stored at room temperature (20° C.) and 4° C. up to 21 days and the potency was tested at T0 and 21 days.

TABLE 9

SPG-003 Formulation Stability in Solution

| Incubation Conditions | Run 1 | Run 2 | Run 3 | Mean |
|---|---|---|---|---|
| Before Incubation | 0.19% | 0.19% | 0.19% | 0.19% |
| 4° C. Incubation - 21 days | 0.19% | 0.18% | 0.19% | 0.19% |
| 20° C. Incubation - 21 days | 0.19% | 0.19% | 0.19% | 0.19% |

To test formulation stability in a tissue homogenate, the SPG-003 formulation was incubated in mouse skin homogenate at 32° C. for 24 hours. After this incubation period, 10 times volume of acetonitrile was added into the homogenate samples to quench the reaction and precipitate the protein. Then the samples were centrifuged and the clear supernatant was analyzed by HPLC.

TABLE 10

SPG-003 Formulation Stability in Solution

| Incubation Conditions | Run 1 | Run 2 | Run 3 | Mean |
|---|---|---|---|---|
| Before Incubation | 95.29 µg/mL | 96.85 µg/mL | 98.63 µg/mL | 96.90 µg/mL |
| After Incubation - 21 days | 83.74 µg/mL | 99.10 µg/mL | 90.25 µg/mL | 91.03 µg/mL |

These experiments indicate that the SPG-003 formulation shows the good stability in solution for at least up to 21 days storage both at room temperature and 4° C. In addition, this formulation is stable in mouse skin homogenate up to 24 hours of incubation at 32° C.

Example 16

In Vivo Androgenetic Alopecia Studies

A mouse model of androgenetic alopecia will be utilized to demonstrate the activity of an ARE disclosed herein. The backs of 7 week old male $C_{57}BL/6$ mice will be shaved and depilated at the start of the study and 100 µL of 1% testosterone will be applied to the back of each mouse on a daily basis to suppress hair regrowth. 10 µL of each ARE will also be applied topically on a daily basis to mice in the presence of 1% testosterone. Depilation will synchronize all the hair follicles into the growth or anagen phase of the hair cycle while the exogenous testosterone will act to suppress hair growth. In the absence of testosterone, complete hair regrowth typically occurs within 14 days. The presence of testosterone delays hair regrowth for about 7 days. Up the addition of an ARE, the delay in regrowth will be reversed, thereby demonstrating the ability of the compound to block the hair growth inhibitory effects of androgens in vivo. Each experimental treatment group of mice will consist of 8-10 animals.

Example 17

In Vivo Sebum Reduction Model

The Syrian hamster ear model will be used to demonstrate the ability of an ARE disclosed herein to suppress sebum production when topically applied. Each ARE will be applied for two weeks. At the completion of the study, animals will be sacrificed, the wax esters extracted and analyzed for lipid content as that has been shown to correlate very well with sebum production. In addition, sebaceous gland size will be evaluated histologically as an independent measurement of sebum production. It has been shown that oral AR antagonists such as spironolactone and cyproterone acetate are effective at reducing both sebum production and acne severity in females.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular compound, composition, article, apparatus, methodology, protocol, and/or reagent, etc., described herein, unless expressly stated as such. In addition, those of ordinary skill in the art will recognize that certain changes, modifications, permutations, alterations, additions, subtractions and sub-combinations thereof can be made in accordance with the teachings herein without departing from the spirit of the present specification. It is therefore intended that the following appended claims and claims hereafter introduced are interpreted to include all such changes, modifications, permutations, alterations, additions, subtractions and sub-combinations as are within their true spirit and scope.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. For instance, as mass spectrometry instruments can vary slightly in determining the mass of a given analyte, the term "about" in the context of the mass of an ion or the mass/charge ratio of an ion refers to +/−0.50 atomic mass unit. At the very least, and not as an attempt to limit the application of the doctrine of equivalents to the scope of the claims, each numerical indication should at least be construed in light of the number of reported significant digits and by applying ordinary rounding techniques.

Use of the terms "may" or "can" in reference to an embodiment or aspect of an embodiment also carries with it the alternative meaning of "may not" or "cannot." As such, if the present specification discloses that an embodiment or an aspect of an embodiment may be or can be included as part of the inventive subject matter, then the negative limitation or exclusionary proviso is also explicitly meant, meaning that an embodiment or an aspect of an embodiment may not be or cannot be included as part of the inventive subject matter. In a similar manner, use of the term "optionally" in reference to an embodiment or aspect of an embodiment means that such embodiment or aspect of the embodiment may be included as part of the inventive subject matter or may not be included as part of the inventive subject matter. Whether such a negative limitation or exclusionary proviso applies will be based on whether the negative limitation or exclusionary proviso is recited in the claimed subject matter.

Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar references used in the context of describing the present invention (especially in the context of the following claims) are to be construed to cover both the singular and the plural, unless otherwise indicated herein or clearly contradicted by context. Further, ordinal indicators—such as "first," "second," "third," etc.— for identified elements are used to distinguish between the elements, and do not indicate or imply a required or limited number of such elements, and do not indicate a particular position or order of such elements unless otherwise specifically stated. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

When used in the claims, whether as filed or added per amendment, the open-ended transitional term "comprising" (and equivalent open-ended transitional phrases thereof like including, containing and having) encompasses all the expressly recited elements, limitations, steps and/or features alone or in combination with unrecited subject matter; the named elements, limitations and/or features are essential, but other unnamed elements, limitations and/or features may be added and still form a construct within the scope of the claim. Specific embodiments disclosed herein may be further limited in the claims using the closed-ended transitional phrases "consisting of" or "consisting essentially of" in lieu of or as an amended for "comprising." When used in the claims, whether as filed or added per amendment, the closed-ended transitional phrase "consisting of" excludes any element, limitation, step, or feature not expressly recited in the claims. The closed-ended transitional phrase "consisting essentially of" limits the scope of a claim to the expressly recited elements, limitations, steps and/or features and any other elements, limitations, steps and/or features that do not materially affect the basic and novel characteristic(s) of the claimed subject matter. Thus, the meaning of the open-ended transitional phrase "comprising" is being defined as encompassing all the specifically recited elements, limitations, steps and/or features as well as any optional, additional unspecified ones. The meaning of the closed-ended transitional phrase "consisting of" is being defined as only including those elements, limitations, steps and/or features specifically recited in the claim whereas the meaning of the closed-ended transitional phrase "consisting essentially of" is being defined as only including those elements, limitations, steps and/or features specifically recited in the claim and those elements, limitations, steps and/or features that do not materially affect the basic and novel characteristic(s) of the claimed subject matter. Therefore, the open-ended transitional phrase "comprising" (and equivalent open-ended transitional phrases thereof) includes within its meaning, as a limiting case, claimed subject matter specified by the closed-ended transitional phrases "consisting of" or "consisting essentially of." As such embodiments described herein or so claimed with the phrase "comprising" are expressly or inherently unambiguously described, enabled and supported herein for the phrases "consisting essentially of" and "consisting of."

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Lastly, the terminology used herein is for the purpose of describing particular embodiments only, and is not intended to limit the scope of the present invention, which is defined solely by the claims. Accordingly, the present invention is not limited to that precisely as shown and described.

The invention claimed is:

1. A compound of formula (I),

ARA-L-EE     (I)

wherein

ARA is an androgen receptor (AR) antagonist that is spironolactone having the following structure:

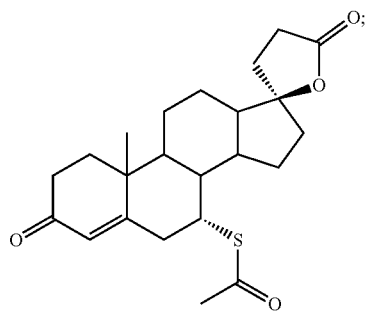 [SMILES: CC(=O)S[C@@H]1CC2=CC(=O)CCC2(C)C2CCC3C(CC[C@@]34CCC(=O)O4)C21]

L is a linker molecule of formula (III), (IV), (V), (VI), (VII), (VIII), (IX) or (X):

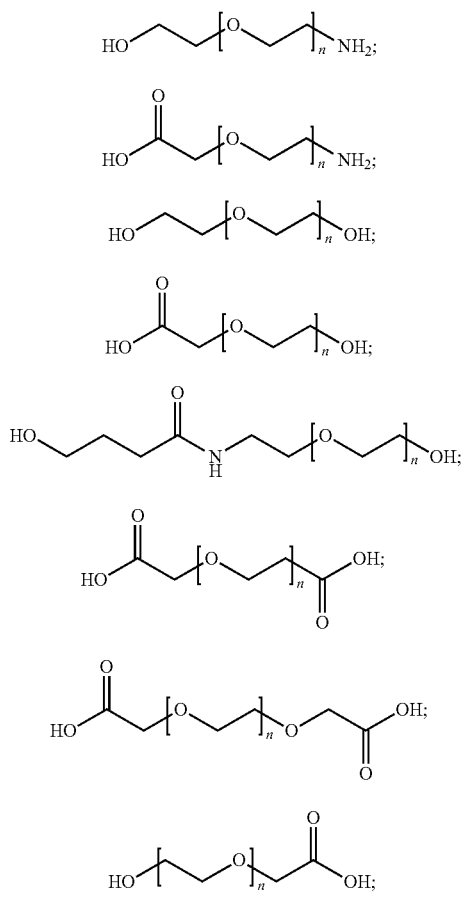

wherein each n is independently any integer from 0 to 10; and

EE is an E3 ligase-recruiting moiety selected from the group consisting of a nutlin moiety, a bestatin moiety, a phthalimide moiety, and a moiety according to formula (XII):

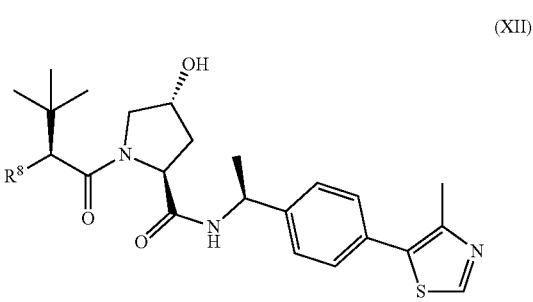

wherein $R^8$ is OH, COOH, $NH_2$, a halogen, $R^9$OH, $R^9$COOH, ROC(O) $NH_2$ or $R^6$C(O) $R^{10}$, wherein $R^9$ is $C_{1-10}$ alkyl, $C_{2-10}$ alkenyl, or $C_{2-10}$ alkynyl, and $R^{10}$ is a halogen;

wherein ARA is conjugated to EE via the linker molecule, and wherein the linker molecule is covalently attached to each of ARA and EE.

2. The compound of claim 1, wherein the E3-ligase recruiting moiety is the moiety according to formula (XII).

3. The compound of claim 2, wherein $R^8$ is $NH_2$.

4. The compound of claim 1, wherein L is a linker molecule according to formula (IX):

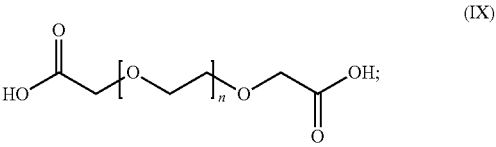

wherein n is any integer from 0 to 10.

5. The compound of claim 1, wherein L is a linker molecule according to formula (X):

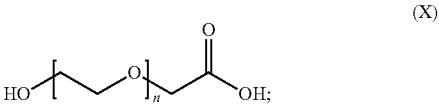

wherein n is any integer from 0 to 10.

6. The compound of claim 1, wherein the compound is according to formula (XXII):
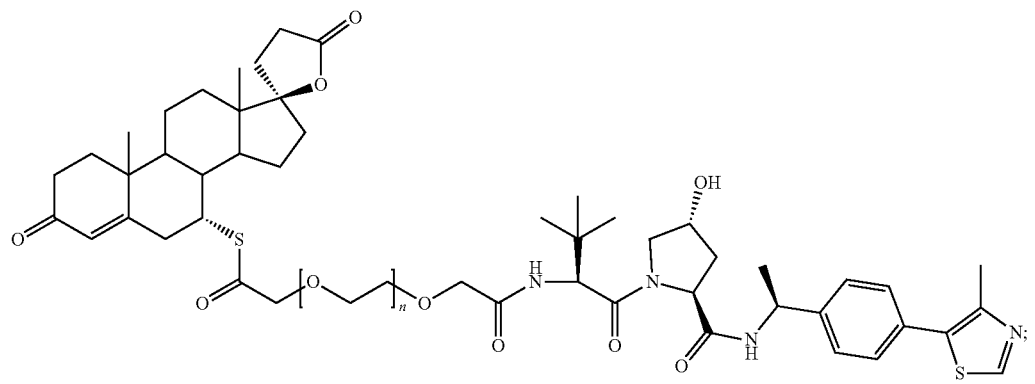
(XXII)
wherein n is any integer from 0 to 10.
7. The compound of claim 1, wherein the compound is selected from the group consisting of:
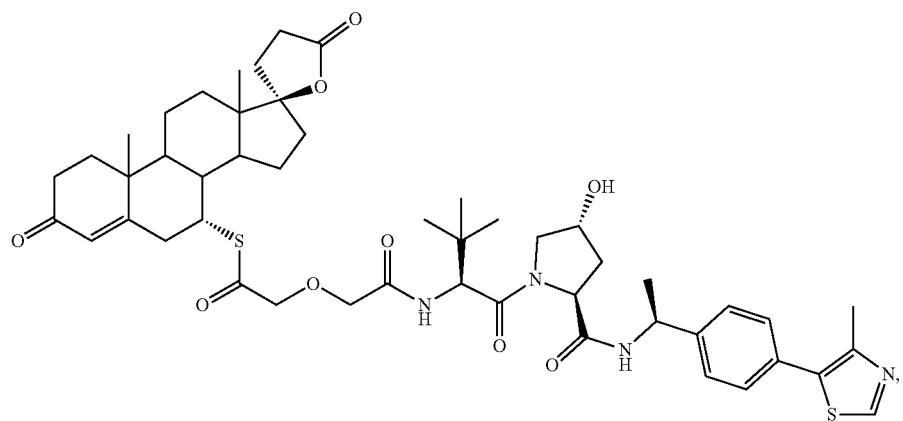
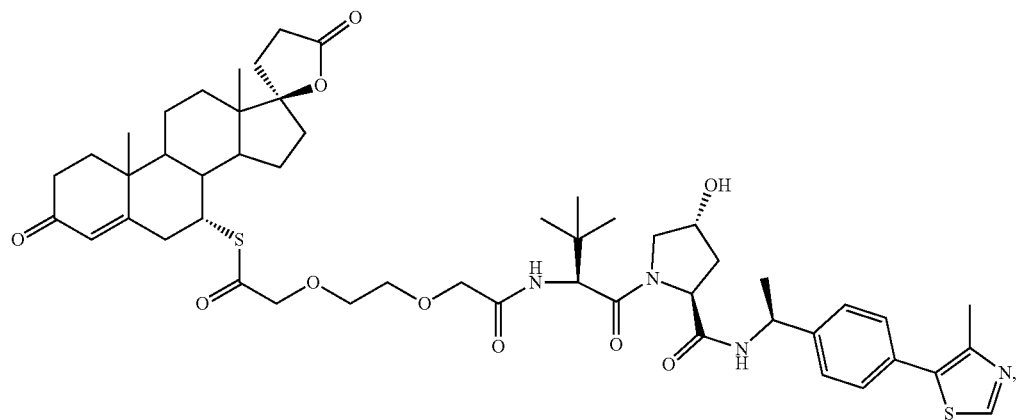

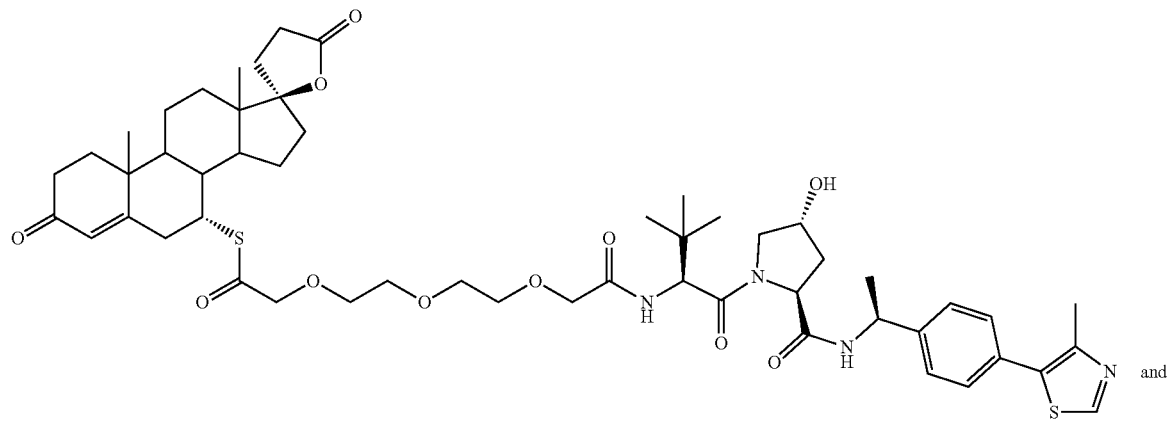

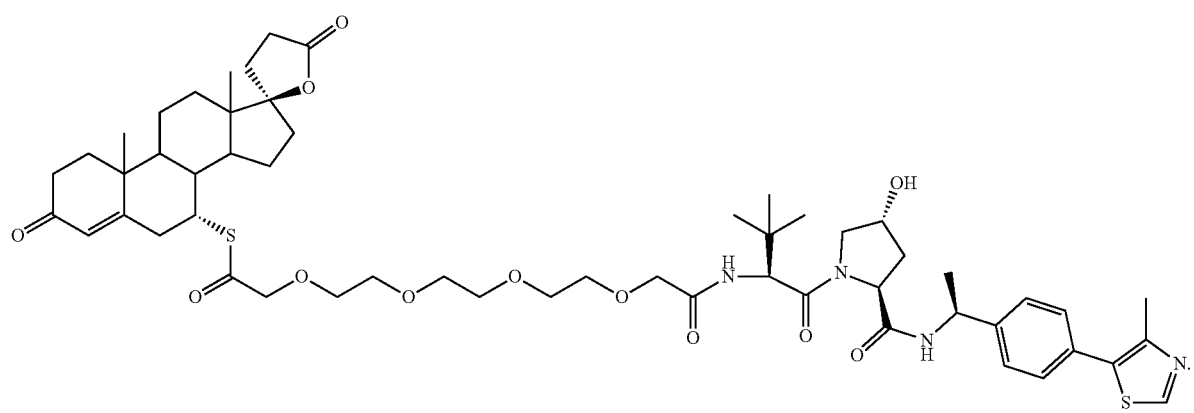

8. A pharmaceutical composition comprising 0.1% to 10% by weight of a compound as defined in claim 1, one or more pharmaceutically acceptable carriers and/or one or more pharmaceutically acceptable components.

9. The pharmaceutical composition according to claim 8, wherein the one or more pharmaceutically acceptable carriers comprise 20% to 40% by weight of denatured alcohol, 40% to 60% by weight of isopropyl myristate, and 10% to 30% by weight of diethylene glycol monoethyl ether.

10. The pharmaceutical composition according to claim 8, wherein the one or more pharmaceutically acceptable carriers comprise 25% to 35% by weight of denatured alcohol, 45% to 55% by weight of isopropyl myristate, and 15% to 25% by weight of diethylene glycol monoethyl ether.

11. A compound of formula (I),

ARA-L-EE    (I)

wherein

ARA is an androgen receptor (AR) antagonist that is ketoconazole having the following structure:

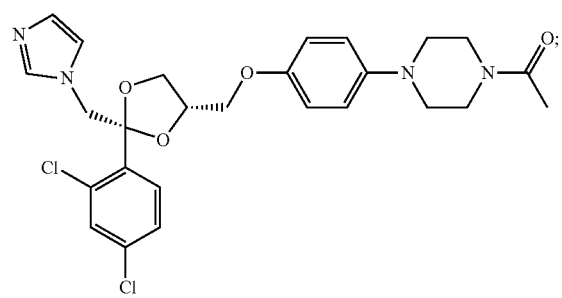 [SMILES: CC(=O)N1CCN(c2ccc(OC[C@H]3CO[C@](Cn4ccnc4)(c4ccc(Cl)cc4Cl)O3)cc2)CC1]

L is a linker molecule of formula (III), (IV), (V), (VI), (VII), (VIII), (IX) or (X):

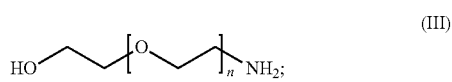    (III)

    (IV)

-continued

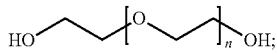 (V)

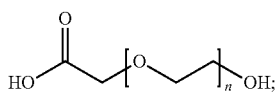 (VI)

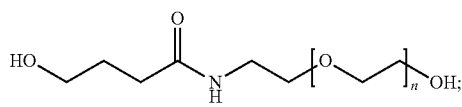 (VII)

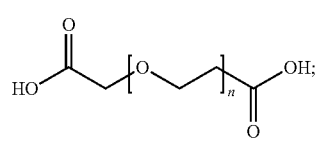 (VIII)

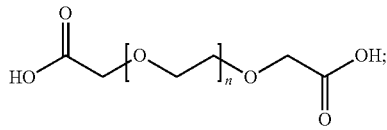 (IX)

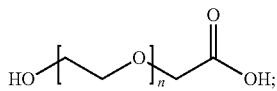 (X)

wherein each n is independently any integer from 0 to 10; and

EE is an E3 ligase-recruiting moiety selected from the group consisting of a nutlin moiety, a bestatin moiety, a phthalimide moiety, and a moiety according to formula (XII):

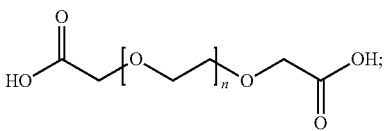 (XII)

wherein $R^8$ is OH, COOH, $NH_2$, a halogen, $R^9OH$, $R^9COOH$, $R^6C(O)NH_2$ or $R^6C(O)R^{10}$, wherein $R^9$ is $C_{1-10}$ alkyl, $C_{2-10}$ alkenyl, or $C_{2-10}$ alkynyl, and $R^{10}$ is a halogen;

wherein ARA is conjugated to EE via the linker molecule, and wherein the linker molecule is covalently attached to each of ARA and EE.

12. The compound of claim 11, wherein the E3-ligase recruiting moiety is the moiety according to formula (XII).

13. The compound of claim 12, wherein $R^8$ is $NH_2$.

14. The compound of claim 11, wherein L is a linker molecule according to formula (IX):

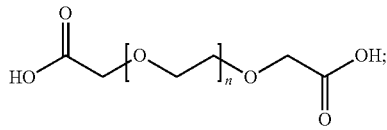 (IX)

wherein n is any integer from 0 to 10.

15. The compound of claim 1, wherein the compound has the following structure:

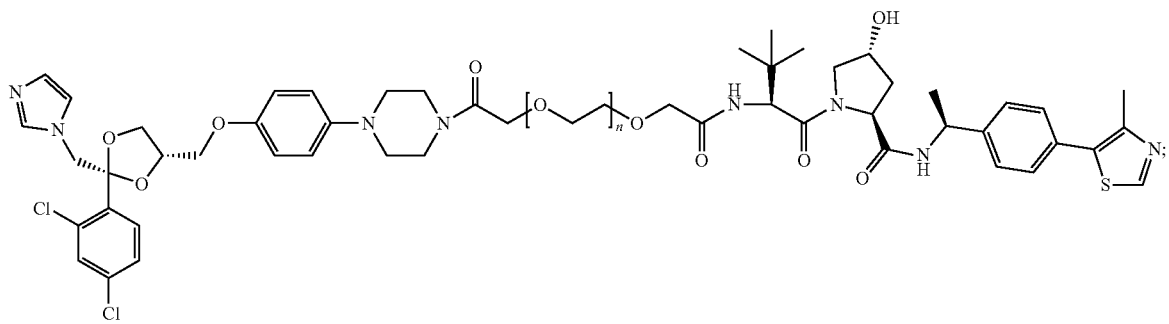

wherein n is any integer from 0 to 10.

16. The compound of claim 15, wherein the compound is selected from the group consisting of:

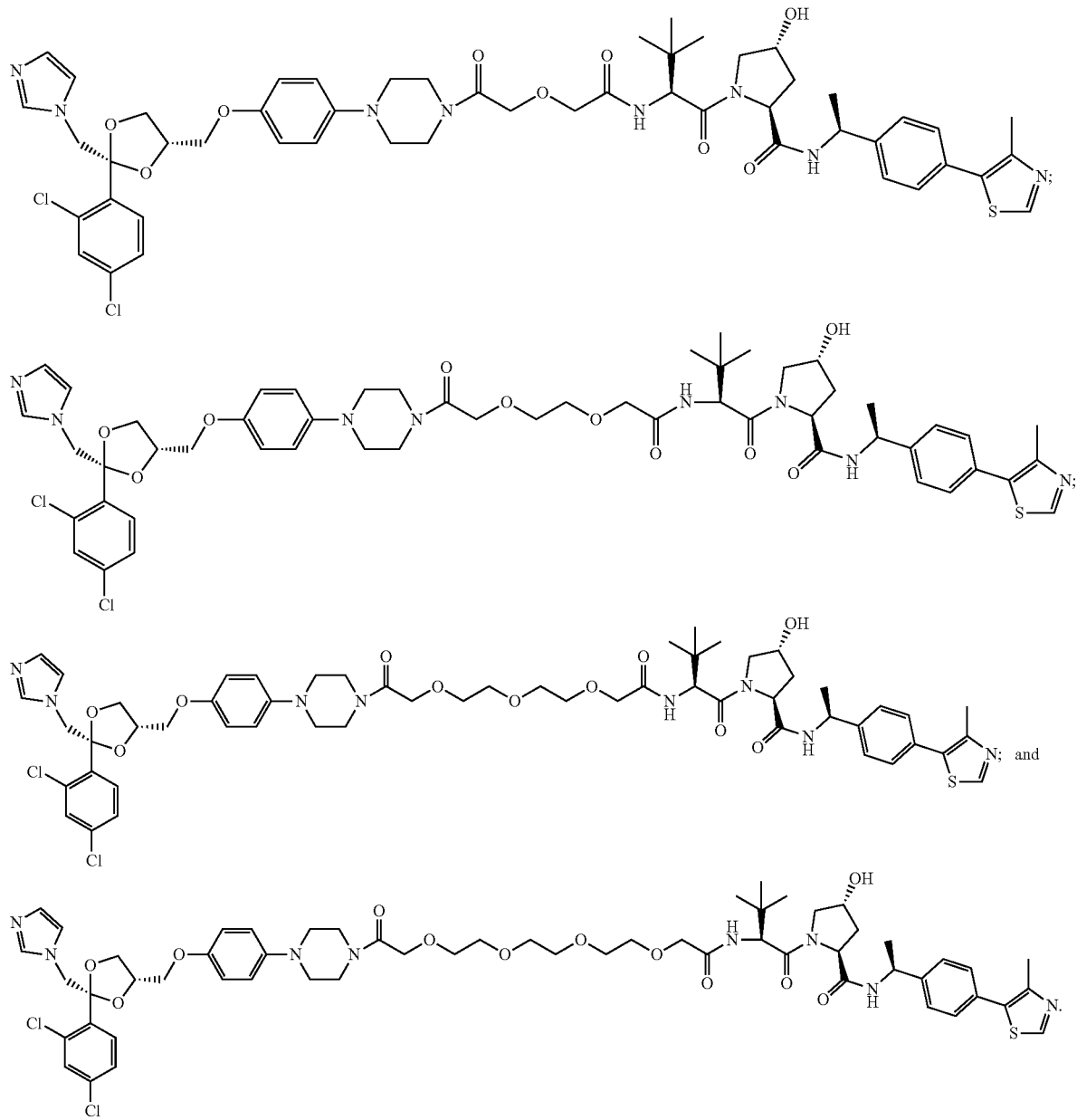

17. A pharmaceutical composition comprising 0.1% to 10% by weight of a compound as defined in claim 11, one or more pharmaceutically acceptable carriers and/or one or more pharmaceutically acceptable components.

18. The pharmaceutical composition according to claim 17, wherein the one or more pharmaceutically acceptable carriers comprise 20% to 40% by weight of denatured alcohol, 40% to 60% by weight of isopropyl myristate, and 10% to 30% by weight of diethylene glycol monoethyl ether.

19. The pharmaceutical composition according to claim 17, wherein the one or more pharmaceutically acceptable carriers comprise 25% to 35% by weight of denatured alcohol, 45% to 55% by weight of isopropyl myristate, and 15% to 25% by weight of diethylene glycol monoethyl ether.

* * * * *